(12) United States Patent
Sano et al.

(10) Patent No.: US 10,377,754 B2
(45) Date of Patent: Aug. 13, 2019

(54) HYDRAZONYL GROUP-CONTAINING CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Yusuke Sano, Osaka (JP); Ikki Yonemura, Osaka (JP); Shunpei Fujie, Osaka (JP); Akiyuki Suwa, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 16/327,236

(22) PCT Filed: Aug. 31, 2017

(86) PCT No.: PCT/JP2017/031454
§ 371 (c)(1),
(2) Date: Feb. 21, 2019

(87) PCT Pub. No.: WO2018/043675
PCT Pub. Date: Mar. 8, 2018

(65) Prior Publication Data
US 2019/0177319 A1    Jun. 13, 2019

(30) Foreign Application Priority Data

Sep. 1, 2016 (JP) .................... 2016-170988

(51) Int. Cl.
| | | |
|---|---|---|
| *C07D 401/14* | (2006.01) | |
| *A61K 31/437* | (2006.01) | |
| *C07D 471/04* | (2006.01) | |
| *A01N 43/90* | (2006.01) | |
| *A01N 47/12* | (2006.01) | |
| *A01N 47/24* | (2006.01) | |
| *A01N 47/34* | (2006.01) | |
| *A01N 51/00* | (2006.01) | |
| *A61K 31/4439* | (2006.01) | |
| *A61K 31/444* | (2006.01) | |

(Continued)

(52) U.S. Cl.
CPC ........... *C07D 471/04* (2013.01); *A01N 43/90* (2013.01); *A01N 47/12* (2013.01); *A01N 47/24* (2013.01); *A01N 47/34* (2013.01); *A01N 51/00* (2013.01); *A61K 31/444* (2013.01); *A61K 31/4439* (2013.01); *A61P 33/00* (2018.01); *C07D 413/04* (2013.01)

(58) Field of Classification Search
CPC .......................... C07D 401/14; A61K 31/437
USPC ................... 546/119, 271.7; 514/303
See application file for complete search history.

(56) References Cited

U.S. PATENT DOCUMENTS

| 5,965,491 A | 10/1999 | Wu et al. |
| 2005/0203149 A1 | 9/2005 | Kawata et al. |

(Continued)

FOREIGN PATENT DOCUMENTS

| EP | 3372595 A1 | 9/2018 |
| JP | 2001-518936 A | 10/2001 |

(Continued)

OTHER PUBLICATIONS

International Search Report for PCT/JP2017/031454 dated Nov. 14, 2017.

(Continued)

*Primary Examiner* — Niloofar Rahmani
(74) *Attorney, Agent, or Firm* — Knobbe Martens Olson & Bear LLP

(57) ABSTRACT

An object of the present invention is to develop and provide a novel agricultural and horticultural insecticide in view of the still immense damage caused by insect pests etc. and the emergence of insect pests resistant to existing insecticides in crop production in the fields of agriculture, horticulture and the like.

Provided is a hydrazonyl group-containing condensed heterocyclic compound or a salt thereof, preferably a condensed heterocyclic compound represented by the general formula (1):

[Chem. 1]

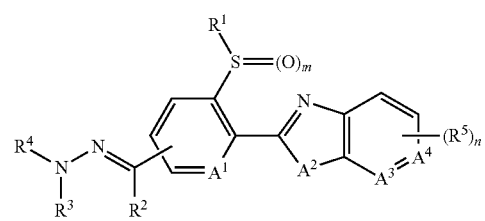

{wherein $R^1$ represents, for example, an alkyl group, $R^2$ represents, for example, a hydrogen atom, $R^3$ and $R^4$ each represent, for example, an alkyl group, a haloalkyl group or an acyl group, $A^1$ represents, for example, a nitrogen atom, $A^2$ represents, for example, N-Me or an oxygen atom, $A^3$ represents, for example, a carbon atom or a nitrogen atom, $A^4$ represents, for example, C—H, m represents, for example, 2, and n represents, for example, 1}, or a salt thereof; an agricultural and horticultural insecticide comprising the compound or a salt thereof as an active ingredient; and a method for using the insecticide.

10 Claims, No Drawings

(51) Int. Cl.
  *C07D 413/04* (2006.01)
  *A61P 33/00* (2006.01)

(56) References Cited

U.S. PATENT DOCUMENTS

| | | |
|---|---|---|
| 2011/0039843 A1 | 2/2011 | Iwakoshi et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1 | 9/2013 | Takahashi et al. |
| 2014/0018373 A1 | 1/2014 | Takyo et al. |
| 2014/0194290 A1 | 7/2014 | Takahashi et al. |
| 2014/0364444 A1 | 12/2014 | Takyo et al. |
| 2015/0197532 A1 | 7/2015 | Takahashi et al. |
| 2016/0009715 A1 | 1/2016 | Takahashi et al. |
| 2016/0021886 A1 | 1/2016 | Yonemura et al. |
| 2016/0159743 A1 | 6/2016 | Takahashi et al. |
| 2016/0368915 A1 | 12/2016 | Tanabe et al. |
| 2017/0073342 A1 | 3/2017 | Fischer et al. |

FOREIGN PATENT DOCUMENTS

| | | | |
|---|---|---|---|
| JP | 2009-280574 A | | 12/2009 |
| JP | 2010-275301 A | | 12/2010 |
| JP | 2011-79774 A | | 4/2011 |
| JP | 2012-131780 A | | 7/2012 |
| JP | 2014-005263 A | | 1/2014 |
| WO | WO 03/059064 A1 | | 7/2003 |
| WO | WO 2012/086848 A1 | | 6/2012 |
| WO | 2014123206 | * | 8/2014 |
| WO | WO 2014/142292 A1 | | 9/2014 |
| WO | WO 2015/002211 A1 | | 1/2015 |
| WO | WO 2015/121136 A1 | | 8/2015 |
| WO | WO 2017/065183 A1 | | 4/2017 |

OTHER PUBLICATIONS

International Preliminary Report on Patentability for PCT/JP2017/031454 dated Mar. 5, 2019.

* cited by examiner

HYDRAZONYL GROUP-CONTAINING CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application Number PCT/JP2017/031454, filed on Aug. 31, 2017, designating the United States of America and published in the Japanese language, which is an International Application of and claims the benefit of priority to Japanese Patent Application No. 2016-170988, filed on Sep. 1, 2016. The disclosures of the above-referenced applications are hereby expressly incorporated by reference in their entireties.

TECHNICAL FIELD

The present invention relates to an agricultural and horticultural insecticide comprising a hydrazonyl group-containing condensed heterocyclic compound or a salt thereof as an active ingredient, and a method for using the insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 7). The literature, however, does not specifically disclose condensed heterocyclic compounds having a hydrazonyl group as a substituting group.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2014/142292
Patent literature 7: WO 2015/121136

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to develop a novel insecticide, particularly an agricultural and horticultural insecticide. As a result, the present inventors found that a heterocyclic compound represented by the general formula (1) which has a hydrazonyl group as a substituting group or a salt of the compound is highly effective as an insecticide. Based on this finding, the present inventors completed the present invention.

That is, the present invention includes the following.

[1] A compound represented by the general formula (1):

[Chem. 1]

{wherein
$R^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
$R^2$ represents
(b1) a hydrogen atom;
(b2) a ($C_1$-$C_6$) alkyl group;
(b3) a ($C_3$-$C_6$) cycloalkyl group; or
(b4) a halo ($C_1$-$C_6$) alkyl group,
$R^3$ and $R^4$ independently represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c14) a phenyl ($C_1$-$C_6$) alkyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group;
(c16) a ($C_3$-$C_6$) cycloalkylcarbonyl group;
(c17) a ($C_1$-$C_6$) alkoxycarbonyl group;

(c18) a halo ($C_1$-$C_6$) alkylcarbonyl group;
(c19) a ($C_1$-$C_6$) alkylthiocarbonyl group;
(c20) a ($C_3$-$C_6$) cycloalkylthiocarbonyl group;
(c21) a ($C_1$-$C_6$) alkoxythiocarbonyl group;
(c22) a halo ($C_1$-$C_6$) alkylthiocarbonyl group;
(c23) a mono-($C_1$-$C_6$) alkylaminothiocarbonyl group;
(c24) a di-($C_1$-$C_6$) alkylaminothiocarbonyl group;
(c25) a ($C_1$-$C_6$) alkylthio group;
(c26) a ($C_1$-$C_6$) alkylsulfinyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group,
  $R^5$ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
  $A^1$, $A^3$ and $A^4$ each represent CH or a nitrogen atom,
  $A^2$ represents an oxygen atom; a sulfur atom; or N—$R^6$ (wherein $R^6$ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
  m represents 0; 1; or 2, and
  n represents 0; 1; or 2}, or
a salt thereof.
[2] The compound or the salt according to the above [1], represented by the general formula (1A):

[Chem. 2]

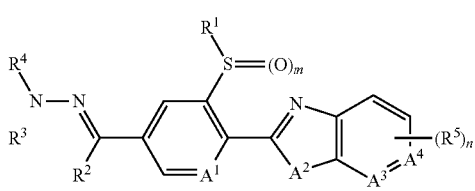

(1A)

{wherein
  $R^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
  $R^2$ represents
(b1) a hydrogen atom;
(b2) a ($C_1$-$C_6$) alkyl group;
(b3) a ($C_3$-$C_6$) cycloalkyl group; or
(b4) a halo ($C_1$-$C_6$) alkyl group,
  $R^3$ and $R^4$ independently represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c14) a phenyl ($C_1$-$C_6$) alkyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group;
(c16) a ($C_3$-$C_6$) cycloalkylcarbonyl group;
(c17) a ($C_1$-$C_6$) alkoxycarbonyl group;
(c18) a halo ($C_1$-$C_6$) alkylcarbonyl group;
(c19) a ($C_1$-$C_6$) alkylthiocarbonyl group;
(c20) a ($C_3$-$C_6$) cycloalkylthiocarbonyl group;
(c21) a ($C_1$-$C_6$) alkoxythiocarbonyl group;
(c22) a halo ($C_1$-$C_6$) alkylthiocarbonyl group;
(c23) a mono-($C_1$-$C_6$) alkylaminothiocarbonyl group;
(c24) a di-($C_1$-$C_6$) alkylaminothiocarbonyl group;
(c25) a ($C_1$-$C_6$) alkylthio group;
(c26) a ($C_1$-$C_6$) alkylsulfinyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group,
  $R^5$ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;

(d11) a halo $(C_2\text{-}C_6)$ alkynyloxy group;
(d12) a $(C_1\text{-}C_6)$ alkylthio group;
(d13) a $(C_1\text{-}C_6)$ alkylsulfinyl group;
(d14) a $(C_1\text{-}C_6)$ alkylsulfonyl group;
(d15) a halo $(C_1\text{-}C_6)$ alkylthio group;
(d16) a halo $(C_1\text{-}C_6)$ alkylsulfinyl group; or
(d17) a halo $(C_1\text{-}C_6)$ alkylsulfonyl group, $A^1$, $A^3$ and $A^4$ each represent CH or a nitrogen atom,
$A^2$ represents an oxygen atom; a sulfur atom; or N—$R^6$ (wherein $R^6$ represents (e1) a $(C_1\text{-}C_6)$ alkyl group; (e2) a $(C_3\text{-}C_6)$ cycloalkyl group; (e3) a $(C_2\text{-}C_6)$ alkenyl group; or (e4) a $(C_2\text{-}C_6)$ alkynyl group),
m represents 0; 1; or 2, and
n represents 0; 1; or 2}.

[3] The compound or the salt according to the above [2], wherein
$R^1$ is (a1) a $(C_1\text{-}C_6)$ alkyl group,
$R^2$ is (b1) a hydrogen atom,
$R^3$ and $R^4$ are independently
(c1) a hydrogen atom;
(c2) a $(C_1\text{-}C_6)$ alkyl group;
(c3) a $(C_2\text{-}C_6)$ alkenyl group;
(c4) a $(C_2\text{-}C_6)$ alkynyl group;
(c5) a $(C_3\text{-}C_6)$ cycloalkyl group;
(c7) a $(C_1\text{-}C_6)$ alkoxy $(C_1\text{-}C_6)$ alkyl group;
(c8) a halo $(C_1\text{-}C_6)$ alkyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a $(C_1\text{-}C_6)$ alkyl group, (f) a halo $(C_1\text{-}C_6)$ alkyl group, (g) a $(C_1\text{-}C_6)$ alkoxy group, (h) a halo $(C_1\text{-}C_6)$ alkoxy group, (i) a $(C_3\text{-}C_6)$ cycloalkyl $(C_1\text{-}C_6)$ alkoxy group, (j) a $(C_1\text{-}C_6)$ alkylthio group, (k) a halo $(C_1\text{-}C_6)$ alkylthio group, (l) a $(C_1\text{-}C_6)$ alkylsulfinyl group, (m) a halo $(C_1\text{-}C_6)$ alkylsulfinyl group, (n) a $(C_1\text{-}C_6)$ alkylsulfonyl group and (o) a halo $(C_1\text{-}C_6)$ alkylsulfonyl group;
(c13) a phenyl $(C_1\text{-}C_6)$ alkyl group;
(c15) a $(C_1\text{-}C_6)$ alkylcarbonyl group;
(c17) a $(C_1\text{-}C_6)$ alkoxycarbonyl group;
(c18) a halo $(C_1\text{-}C_6)$ alkylcarbonyl group;
(c21) a $(C_1\text{-}C_6)$ alkoxythiocarbonyl group;
(c23) a mono-$(C_1\text{-}C_6)$ alkylaminothiocarbonyl group;
(c24) a di-$(C_1\text{-}C_6)$ alkylaminothiocarbonyl group;
(c27) a $(C_1\text{-}C_6)$ alkylsulfonyl group;
(c28) a $(C_1\text{-}C_6)$ alkylthio $(C_1\text{-}C_6)$ alkyl group;
(c29) a $(C_1\text{-}C_6)$ alkylsulfinyl $(C_1\text{-}C_6)$ alkyl group;
(c30) a $(C_1\text{-}C_6)$ alkylsulfonyl $(C_1\text{-}C_6)$ alkyl group;
(c31) a halo $(C_1\text{-}C_6)$ alkylthio $(C_1\text{-}C_6)$ alkyl group;
(c32) a halo $(C_1\text{-}C_6)$ alkylsulfinyl $(C_1\text{-}C_6)$ alkyl group;
(c33) a halo $(C_1\text{-}C_6)$ alkylsulfonyl $(C_1\text{-}C_6)$ alkyl group; or
(c34) a cyano $(C_1\text{-}C_6)$ alkyl group,
$R^5$ is
(d8) a halo $(C_1\text{-}C_6)$ alkyl group;
(d15) a halo $(C_1\text{-}C_6)$ alkylthio group; or
(d17) a halo $(C_1\text{-}C_6)$ alkylsulfonyl group, $A^1$ is a nitrogen atom,
$A^3$ is CH or a nitrogen atom,
$A^4$ is CH,
$A^2$ is an oxygen atom or N—$R^6$ (wherein $R^6$ is (e1) a $(C_1\text{-}C_6)$ alkyl group),
m is 2, and
n is 1.

[4] The compound or the salt according to the above [2] or [3], wherein
$R^3$ and $R^4$ are independently
(c1) a hydrogen atom;
(c2) a $(C_1\text{-}C_6)$ alkyl group;
(c7) a $(C_1\text{-}C_6)$ alkoxy $(C_1\text{-}C_6)$ alkyl group;
(c8) a halo $(C_1\text{-}C_6)$ alkyl group;
(c12) a phenyl group having, on the ring, 1 to 5 substituting groups independently selected from the group consisting of (a) a halogen atom, (b) a cyano group, (c) a nitro group, (d) a formyl group, (e) a $(C_1\text{-}C_6)$ alkyl group, (f) a halo $(C_1\text{-}C_6)$ alkyl group, (g) a $(C_1\text{-}C_6)$ alkoxy group, (h) a halo $(C_1\text{-}C_6)$ alkoxy group, (i) a $(C_3\text{-}C_6)$ cycloalkyl $(C_1\text{-}C_6)$ alkoxy group, (j) a $(C_1\text{-}C_6)$ alkylthio group, (k) a halo $(C_1\text{-}C_6)$ alkylthio group, (l) a $(C_1\text{-}C_6)$ alkylsulfinyl group, (m) a halo $(C_1\text{-}C_6)$ alkylsulfinyl group, (n) a $(C_1\text{-}C_6)$ alkylsulfonyl group and (o) a halo $(C_1\text{-}C_6)$ alkylsulfonyl group;
(c15) a $(C_1\text{-}C_6)$ alkylcarbonyl group;
(c17) a $(C_1\text{-}C_6)$ alkoxycarbonyl group;
(c21) a $(C_1\text{-}C_6)$ alkoxythiocarbonyl group;
(c23) a mono-$(C_1\text{-}C_6)$ alkylaminothiocarbonyl group;
(c24) a di-$(C_1\text{-}C_6)$ alkylaminothiocarbonyl group;
(c27) a $(C_1\text{-}C_6)$ alkylsulfonyl group; or
(c33) a halo $(C_1\text{-}C_6)$ alkylsulfonyl $(C_1\text{-}C_6)$ alkyl group.

[5] The compound or the salt according to the above [1], represented by the general formula (1B):

[Chem. 3]

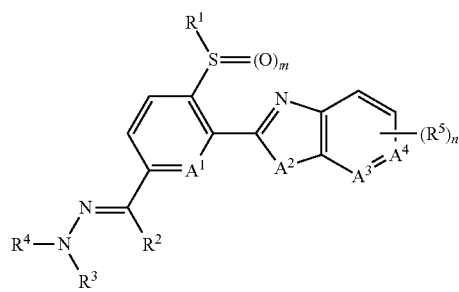

(1B)

{wherein
$R^1$ represents
(a1) a $(C_1\text{-}C_6)$ alkyl group;
(a2) a $(C_3\text{-}C_6)$ cycloalkyl group;
(a3) a $(C_2\text{-}C_6)$ alkenyl group; or
(a4) a $(C_2\text{-}C_6)$ alkynyl group,
$R^2$ represents
(b1) a hydrogen atom;
(b2) a $(C_1\text{-}C_6)$ alkyl group;
(b3) a $(C_3\text{-}C_6)$ cycloalkyl group; or
(b4) a halo $(C_1\text{-}C_6)$ alkyl group,
$R^3$ and $R^4$ independently represents
(c1) a hydrogen atom;
(c2) a $(C_1\text{-}C_6)$ alkyl group;
(c3) a $(C_2\text{-}C_6)$ alkenyl group;
(c4) a $(C_2\text{-}C_6)$ alkynyl group;
(c5) a $(C_3\text{-}C_6)$ cycloalkyl group;
(c6) a $(C_3\text{-}C_6)$ cycloalkyl $(C_1\text{-}C_6)$ alkyl group;
(c7) a $(C_1\text{-}C_6)$ alkoxy $(C_1\text{-}C_6)$ alkyl group;
(c8) a halo $(C_1\text{-}C_6)$ alkyl group;
(c9) a halo $(C_2\text{-}C_6)$ alkenyl group;
(c10) a halo $(C_2\text{-}C_6)$ alkynyl group;
(c11) a phenyl group;

(c12) a phenyl group having, on the ring, 1 to 5 substituting groups independently selected from the group consisting of (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group;
(c14) a phenyl $(C_1-C_6)$ alkyl group having, on the ring, 1 to 5 substituting groups independently selected from the group consisting of (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c15) a $(C_1-C_6)$ alkylcarbonyl group;
(c16) a $(C_3-C_6)$ cycloalkylcarbonyl group;
(c17) a $(C_1-C_6)$ alkoxycarbonyl group;
(c18) a halo $(C_1-C_6)$ alkylcarbonyl group;
(c19) a $(C_1-C_6)$ alkylthiocarbonyl group;
(c20) a $(C_3-C_6)$ cycloalkylthiocarbonyl group;
(c21) a $(C_1-C_6)$ alkoxythiocarbonyl group;
(c22) a halo $(C_1-C_6)$ alkylthiocarbonyl group;
(c23) a mono-$(C_1-C_6)$ alkylaminothiocarbonyl group;
(c24) a di-$(C_1-C_6)$ alkylaminothiocarbonyl group;
(c25) a $(C_1-C_6)$ alkylthio group;
(c26) a $(C_1-C_6)$ alkylsulfinyl group;
(c27) a $(C_1-C_6)$ alkylsulfonyl group;
(c28) a $(C_1-C_6)$ alkylthio $(C_1-C_6)$ alkyl group;
(c29) a $(C_1-C_6)$ alkylsulfinyl $(C_1-C_6)$ alkyl group;
(c30) a $(C_1-C_6)$ alkylsulfonyl $(C_1-C_6)$ alkyl group;
(c31) a halo $(C_1-C_6)$ alkylthio $(C_1-C_6)$ alkyl group;
(c32) a halo $(C_1-C_6)$ alkylsulfinyl $(C_1-C_6)$ alkyl group;
(c33) a halo $(C_1-C_6)$ alkylsulfonyl $(C_1-C_6)$ alkyl group; or
(c34) a cyano $(C_1-C_6)$ alkyl group,
$R^5$ represents
(d1) a halogen atom;
(d2) a cyano group;
(d3) a nitro group;
(d4) a $(C_1-C_6)$ alkyl group;
(d5) a $(C_1-C_6)$ alkoxy group;
(d6) a $(C_2-C_6)$ alkenyloxy group;
(d7) a $(C_2-C_6)$ alkynyloxy group;
(d8) a halo $(C_1-C_6)$ alkyl group;
(d9) a halo $(C_1-C_6)$ alkoxy group;
(d10) a halo $(C_2-C_6)$ alkenyloxy group;
(d11) a halo $(C_2-C_6)$ alkynyloxy group;
(d12) a $(C_1-C_6)$ alkylthio group;
(d13) a $(C_1-C_6)$ alkylsulfinyl group;
(d14) a $(C_1-C_6)$ alkylsulfonyl group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
$A^1$, $A^3$ and $A^4$ each represent CH or a nitrogen atom,
$A^2$ represents an oxygen atom; a sulfur atom; or N—$R^6$ (wherein $R^6$ represents (e1) a $(C_1-C_6)$ alkyl group; (e2) a $(C_3-C_6)$ cycloalkyl group; (e3) a $(C_2-C_6)$ alkenyl group; or (e4) a $(C_2-C_6)$ alkynyl group),
m represents 0; 1; or 2, and
n represents 0; 1; or 2}.

[6] The compound or the salt according to the above [5], wherein
$R^1$ is (a1) a $(C_1-C_6)$ alkyl group,
$R^2$ is (b1) a hydrogen atom,
$R^3$ and $R^4$ are independently
(c1) a hydrogen atom;
(c2) a $(C_1-C_6)$ alkyl group;
(c3) a $(C_2-C_6)$ alkenyl group;
(c4) a $(C_2-C_6)$ alkynyl group;
(c5) a $(C_3-C_6)$ cycloalkyl group;
(c7) a $(C_1-C_6)$ alkoxy $(C_1-C_6)$ alkyl group;
(c8) a halo $(C_1-C_6)$ alkyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group;
(c15) a $(C_1-C_6)$ alkylcarbonyl group;
(c17) a $(C_1-C_6)$ alkoxycarbonyl group;
(c18) a halo $(C_1-C_6)$ alkylcarbonyl group;
(c21) a $(C_1-C_6)$ alkoxythiocarbonyl group;
(c23) a mono-$(C_1-C_6)$ alkylaminothiocarbonyl group;
(c24) a di-$(C_1-C_6)$ alkylaminothiocarbonyl group;
(c27) a $(C_1-C_6)$ alkylsulfonyl group;
(c28) a $(C_1-C_6)$ alkylthio $(C_1-C_6)$ alkyl group;
(c29) a $(C_1-C_6)$ alkylsulfinyl $(C_1-C_6)$ alkyl group;
(c30) a $(C_1-C_6)$ alkylsulfonyl $(C_1-C_6)$ alkyl group;
(c31) a halo $(C_1-C_6)$ alkylthio $(C_1-C_6)$ alkyl group;
(c32) a halo $(C_1-C_6)$ alkylsulfinyl $(C_1-C_6)$ alkyl group;
(c33) a halo $(C_1-C_6)$ alkylsulfonyl $(C_1-C_6)$ alkyl group; or
(c34) a cyano $(C_1-C_6)$ alkyl group,
$R^5$ is
(d8) a halo $(C_1-C_6)$ alkyl group;
(d15) a halo $(C_1-C_6)$ alkylthio group; or
(d17) a halo $(C_1-C_6)$ alkylsulfonyl group,
$A^1$ is a nitrogen atom,
$A^3$ is CH or a nitrogen atom,
$A^4$ is CH,
$A^2$ is an oxygen atom or N—$R^6$ (wherein $R^6$ is (e1) a $(C_1-C_6)$ alkyl group),
m is 2, and
n is 1.
[7] The compound or the salt according to the above [5] or [6], wherein
$R^3$ and $R^4$ are independently
(c1) a hydrogen atom;
(c2) a $(C_1-C_6)$ alkyl group;
(c7) a $(C_1-C_6)$ alkoxy $(C_1-C_6)$ alkyl group;
(c8) a halo $(C_1-C_6)$ alkyl group;
(c15) a $(C_1-C_6)$ alkylcarbonyl group;
(c17) a $(C_1-C_6)$ alkoxycarbonyl group;
(c18) a halo $(C_1-C_6)$ alkylcarbonyl group;
(c21) a $(C_1-C_6)$ alkoxythiocarbonyl group; or
(c33) a halo $(C_1-C_6)$ alkylsulfonyl $(C_1-C_6)$ alkyl group.
[8] An agricultural and horticultural insecticide comprising the compound or the salt according to any of the above [1] to [7] as an active ingredient.

[9] A method for using an agricultural and horticultural insecticide, comprising treating plants or soil with an effective amount of the agricultural and horticultural insecticide according to the above [8].

[10] Use of the compound or the salt according to any of the above [1] to [7] as an agricultural and horticultural insecticide.

[11] An animal ectoparasite control agent comprising an effective amount of the compound or the salt according to any of the above [1] to [7] as an active ingredient.

Advantageous Effects of Invention

The compound of the present invention or a salt thereof is not only highly effective as an agricultural and horticultural insecticide but also effective against pests which live on pets such as dogs and cats and domestic animals such as cattle and sheep, and against other harmful pests such as termites.

DESCRIPTION OF EMBODIMENTS

In the definitions of the general formula (1) representing the compound of the present invention or a salt thereof, "halo" refers to a "halogen atom" and represents a chlorine atom, a bromine atom, an iodine atom or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_2-C_6)$ alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "$(C_2-C_6)$ alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "$(C_1-C_6)$ alkyl group", "$(C_2-C_6)$ alkenyl group", "$(C_2-C_6)$ alkynyl group", "$(C_3-C_6)$ cycloalkyl group", "$(C_1-C_6)$ alkoxy group", "$(C_2-C_6)$ alkenyloxy group", "$(C_2-C_6)$ alkynyloxy group", "$(C_1-C_6)$ alkylthio group", "$(C_1-C_6)$ alkylsulfinyl group" or "$(C_1-C_6)$ alkylsulfonyl group" may be substituted with one or more halogen atoms at a substitutable position(s), and in the case where any of the above-listed groups is substituted with two or more halogen atoms, the halogen atoms may be the same or different.

The above-mentioned "group substituted with one or more halogen atoms" is expressed as a "halo $(C_1-C_6)$ alkyl group", a "halo $(C_2-C_6)$ alkenyl group", a "halo $(C_2-C_6)$ alkynyl group", a "halo $(C_3-C_6)$ cycloalkyl group", a "halo $(C_1-C_6)$ alkoxy group", a "halo $(C_2-C_6)$ alkenyloxy group", a "halo $(C_2-C_6)$ alkynyloxy group", a "halo $(C_1-C_6)$ alkylthio group", a "halo $(C_1-C_6)$ alkylsulfinyl group" or a "halo $(C_1-C_6)$ alkylsulfonyl group". The above definitions and examples of each group in the present invention are all obvious to those skilled in the art.

The expressions "$(C_1-C_6)$", "$(C_2-C_6)$", "$(C_3-C_6)$", etc. each refer to the range of the number of carbon atoms in each group. The same definition holds true for groups in which two or more of the above-mentioned groups are coupled together, and for example, the "$(C_1-C_6)$ alkoxy $(C_1-C_6)$ alkyl group" means that a straight-chain or branched-chain alkoxy group of 1 to 6 carbon atoms is bound to a straight-chain or branched-chain alkyl group of 1 to 6 carbon atoms.

Examples of the salt of the compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention. The compound represented by the general formula (1) of the present invention can exist as a syn isomer (Z isomer) and/or an anti isomer (E isomer) due to the presence of the hydrazonyl group. The compound of the present invention may be either of these isomers, or a mixture of the isomers at any ratio.

Preferable embodiments of the compound represented by the general formula (1) of the present invention or a salt thereof are described below.

$R^1$ is preferably (a1) a ($C_1$-$C_6$) alkyl group, $R^2$ is preferably (b1) a hydrogen atom, $R^3$ and $R^4$ are preferably independently (c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c7) a ($C_1$-$C_6$) alkoxy ($C_1$-$C_6$) alkyl group;
(c8) a halo ($C_1$-$C_6$) alkyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c15) a ($C_1$-$C_6$) alkylcarbonyl group;
(c17) a ($C_1$-$C_6$) alkoxycarbonyl group;
(c18) a halo ($C_1$-$C_6$) alkylcarbonyl group;
(c21) a ($C_1$-$C_6$) alkoxythiocarbonyl group;
(c23) a mono-($C_1$-$C_6$) alkylaminothiocarbonyl group;
(c24) a di-($C_1$-$C_6$) alkylaminothiocarbonyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group, and more preferably independently (c1) a hydrogen atom;
(c2) a ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group;
(c17) a ($C_1$-$C_6$) alkoxycarbonyl group;
(c21) a ($C_1$-$C_6$) alkoxythiocarbonyl group;
(c23) a mono-($C_1$-$C_6$) alkylaminothiocarbonyl group;
(c24) a di-($C_1$-$C_6$) alkylaminothiocarbonyl group;
(c27) a ($C_1$-$C_6$) alkylsulfonyl group; or
(c33) a halo ($C_1$-$C_6$) alkylsulfonyl ($C_1$-$C_6$) alkyl group, $R^5$ is preferably (d8) a halo ($C_1$-$C_6$) alkyl group;
(d15) a halo ($C_1$-$C_6$) alkylthio group; or
(d17) a halo ($C_1$-$C_6$) alkylsulfonyl group, $A^1$ is preferably a nitrogen atom, $A^3$ is preferably CH or a nitrogen atom, $A^4$ is preferably CH, $A^2$ is preferably an oxygen atom or N—$R^6$ (wherein $R^6$ is preferably (e1) a ($C_1$-$C_6$) alkyl group), m is preferably 2, and n is preferably 1.

The compound represented by the general formula (1) of the present invention or a salt thereof can be produced according to, for example, the production methods described below, but the present invention is not limited thereto. The starting compounds and intermediate compounds used in the present invention can be produced according to known methods found in the literature or modified methods thereof.

Production Method 1

[Chem. 4]

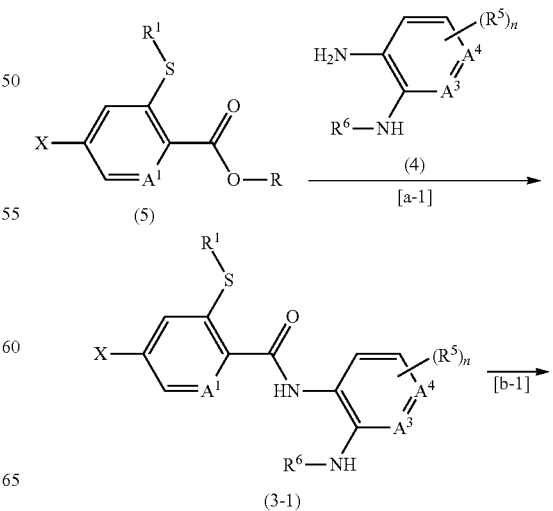

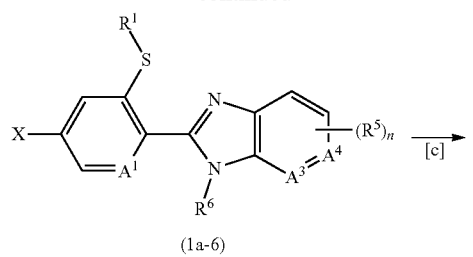

(1a-6)

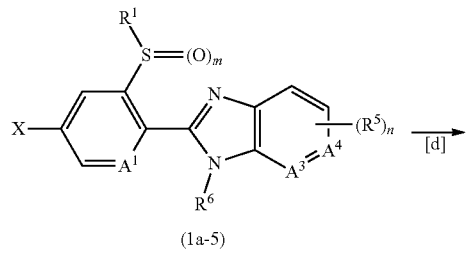

(1a-5)

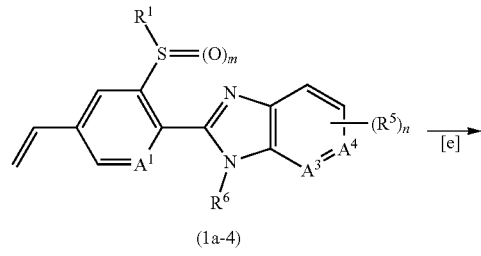

(1a-4)

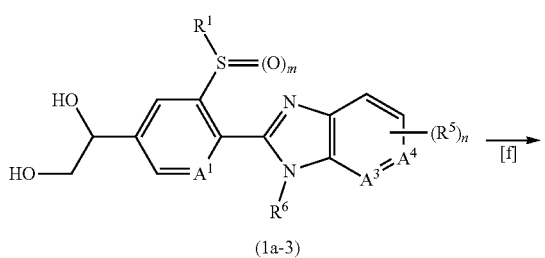

(1a-3)

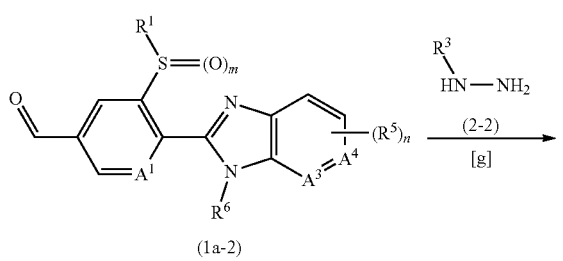

(1a-2)

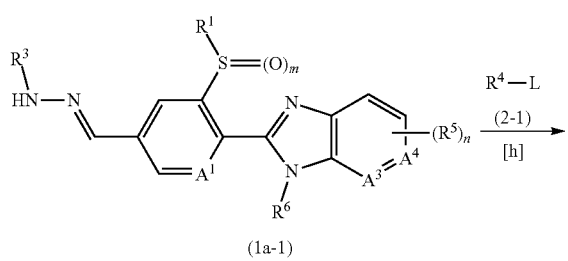

(1a-1)

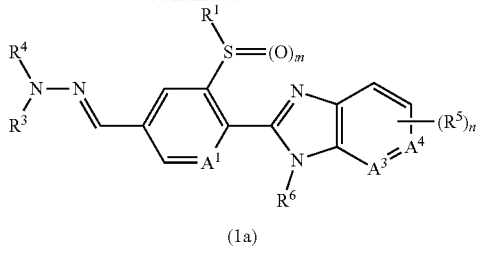

(1a)

{In the formula, $R^1$, $R^3$, $R^4$, $R^5$, $R^6$, $A^1$, $A^3$, $A^4$, m and n are as defined above; X represents a halogen atom such as a fluorine, chlorine, bromine or iodine atom (the same shall apply herein); L represents a leaving group such as a halogen atom, a methane sulfonyloxy group, a p-toluenesulfonyloxy group and a trifluoromethane sulfonyloxy group; and R represents a $C_1$-$C_3$ alkyl group such as a methyl group and an ethyl group.}

The compound represented by the general formula (1a) of the present invention can be produced through the steps [a-1], [b-1], [c], [d], [e], [f], [g] and [h] described below.

Step [a-1]

A step of amidating the compound represented by the general formula (5) by reaction with the compound represented by the general formula (4) to produce the compound represented by the general formula (3-1).

Step [b-1]

A step of intramolecularly cyclizing the compound represented by the general formula (3-1) to produce the compound represented by the general formula (1a-6).

Step [c]

A step of oxidizing the compound represented by the general formula (1a-6) to produce the compound represented by the general formula (1a-5).

Step [d]

A step of subjecting the compound represented by the general formula (1a-5) to cross-coupling with a vinyl compound to produce the compound represented by the general formula (1a-4).

Step [e]

A step of oxidizing the vinyl group of the compound represented by the general formula (1a-4) to a dihydroxylated vinyl group to produce the compound represented by the general formula (1a-3).

Step [f]

A step of oxidizing the compound represented by the general formula (1a-3) to produce the compound represented by the general formula (1a-2).

Step [g]

A step of subjecting the compound represented by the general formula (1a-2) to condensation with the compound represented by the general formula (2-2) to produce the compound represented by the general formula (1a-1).

Step [h]

A step of reacting the compound represented by the general formula (1a-1) with the compound represented by the general formula (2-1) to produce the compound represented by the general formula (1a).

Production Method at Step [a-1]

The amide compound represented by the general formula (3-1) can be produced by reacting the carboxylic acid ester represented by the general formula (5) with the compound represented by the general formula (4) in the presence of a base and an inert solvent.

Examples of the base that can be used in this reaction include inorganic bases such as sodium hydroxide, potassium hydroxide, sodium carbonate, potassium carbonate, sodium hydrogen carbonate and potassium hydrogen carbonate; alkali metal hydrides such as sodium hydride and potassium hydride; acetates such as potassium acetate; alkali metal alkoxides such as potassium t-butoxide, sodium methoxide and sodium ethoxide; tertiary amines such as triethylamine, diisopropylethylamine and 1,8-diazabicyclo [5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (5).

The inert solvent used in this reaction may be any solvent that does not markedly inhibit the progress of the reaction, and examples include aromatic hydrocarbons such as benzene, toluene and xylene; halogenated aromatic hydrocarbons such as chlorobenzene and dichlorobenzene; straight-chain or cyclic ethers such as diethyl ether, methyl tert-butyl ether, dioxane and tetrahydrofuran; amides such as dimethylformamide and dimethylacetamide; and aprotic polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (5).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [b-1]

The compound represented by the general formula (1a-6) can be produced by allowing the amide compound represented by the general formula (3-1) to react in the presence of an acid and an inert solvent.

Examples of the acid that can be used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is usually selected as appropriate from the range of a 0.01- to 10-fold molar amount relative to the amide compound represented by the general formula (3-1).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and aprotic polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (3-1).

The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [c]

The compound represented by the general formula (1a-5) can be produced by reacting the compound represented by the general formula (1a-6) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is usually selected as appropriate from the range of a 1- to 5-fold molar amount relative to the compound represented by the general formula (1a-6).

The inert solvent used in this reaction may be any solvent that does not markedly inhibit the reaction, and examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; aprotic polar solvents such as N,N-dimethylformamide, N,N-dimethylacetamide and 1,3-dimethyl-2-imidazolidinone; and water. One of these inert solvents may be used alone, and also two or more of them may be used as a mixture. The amount of the inert solvent used is usually selected as appropriate from the range of 0.1 to 100 L relative to 1 mol of the compound represented by the general formula (1a-6).

The reaction temperature is usually selected as appropriate from the range of −10° C. to the reflux temperature of the inert solvent used. The reaction time varies with the reaction scale, the reaction temperature and the like and is not the same in every case, but is usually selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [d]

The compound represented by the general formula (1a-4) can be produced by subjecting the compound represented by the general formula (1a-5) to cross-coupling with a vinyl compound in the presence of a metal catalyst and a base in an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an amine complex and an acetylacetonate complex". Preferred is a palladium catalyst. The amount of the metal catalyst used is usually selected as appropriate from the range of 0.001 to 100 mol % relative to the compound represented by the general formula (1a-5).

Examples of the palladium catalyst include palladium metals such as palladium black and palladium sponge as well as supported palladium metals such as palladium/alumina, palladium/carbon, palladium/silica and palladium/type Y zeolite. Also included are metal salts of palladium such as palladium chloride, palladium bromide, palladium iodide and palladium acetate. Other examples of the palladium catalyst include complex compounds of palladium such as π-allylpalladium chloride dimer, palladium acetylacetonate, dichlorobis(acetonitrile)palladium, dichlorobis(benzonitrile)palladium, bis(dibenzylideneacetone)palladium, tris(dibenzylideneacetone)dipalladium, tris(dibenzylideneacetone)dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium and a [(diphenylphosphino)ferrocene]dichloropalladium-dichloromethane complex. The amount of the palladium catalyst used is usually selected as appropriate from the range of 0.001 to 100 mol % relative to the compound represented by the general formula (1a-5).

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl)phosphine, tricyclohexylphosphine, tri-o-tolylphosphine, trioctylphosphine, 9,9-dimethyl-4,5-bis(diphenylphosphino)xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino)ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl. The amount of the tertiary phosphine used is usually selected as appropriate from the range of 0.002 to 400 mol % relative to the compound represented by the general formula (1a-5).

Examples of the vinyl compound that can be used in this reaction include vinylmagnesium bromide, vinylmagnesium chloride, vinylzinc chloride, tributylvinyltin, potassium vinyltrifluoroborate, vinylboronic acid, vinylboronic anhydride, vinylboronic acid 2-methyl-2,4-pentanediol ester, vinylboronic acid pinacol ester and triethoxyvinylsilane. The amount of the vinyl compound used is usually selected as appropriate from the range of a 1- to 5-fold molar amount relative to the compound represented by the general formula (1a-5).

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually selected as appropriate from the range of a 1- to 5-fold molar amount relative to the compound represented by the general formula (1a-5).

The inert solvent used in this reaction may be any solvent that does not markedly inhibit the reaction, and examples include alcohols such as methanol, ethanol, propanol, butanol and 2-propanol; straight-chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; aprotic polar solvents such as N,N-dimethylformamide, N,N-dimethylacetamide, dimethyl sulfoxide and 1,3-dimethyl-2-imidazolidinone; and water. One of these inert solvents may be used alone, and also two or more of them may be used as a mixture. The amount of the inert solvent used is usually selected as appropriate from the range of 0.1 to 100 L relative to 1 mol of the compound represented by the general formula (1a-6).

The reaction temperature in this reaction is usually in the range of about 0° C. to the boiling point of the solvent used. The reaction time varies with the reaction scale, the reaction temperature and the like, but is usually selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by the usual method. As needed, recrystallization, column chromatography, etc. can be employed for the purification of the compound of interest.

Production Method at Step [e]

The compound represented by the general formula (1a-3) can be produced by allowing the vinyl group-containing compound represented by the general formula (1a-4) to react in the presence of osmium tetroxide and an oxidizing agent according to the method described in the Lecture of Experimental Chemistry (Jikken Kagaku Kouza), 4th edition, vol. 23, Organic Chemistry V, Oxidation Reaction (published by Maruzen Co., Ltd.). After the reaction is completed, the compound of interest is isolated from the post-reaction mixture by the usual method. As needed, recrystallization, column chromatography, etc. can be employed for the purification of the compound of interest.

Production Method at Step [f]

The compound represented by the general formula (1a-2) can be produced by reacting the compound represented by the general formula (1a-3) with a periodic acid compound in the presence of an inert solvent according to the method described in the New Lecture of Experimental Chemistry (Shin Jikken Kagaku Kouza), vol. 15, Oxidation and Reduction I-1 (published by Maruzen Co., Ltd). After the reaction is completed, the compound of interest is isolated from the post-reaction mixture by the usual method. As needed, recrystallization, column chromatography, etc. can be employed for the purification of the compound of interest.

Production Method at Step [g]

The condensed heterocyclic compound represented by the general formula (1a-1) can be produced by reacting the compound represented by the general formula (1a-2) with the compound represented by the general formula (2-2) in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is selected as appropriate from the range of a 0.01- to 10-fold molar amount relative to the compound represented by the general formula (1a-2).

The inert solvent used in this reaction may be any solvent that does not markedly inhibit the progress of the reaction, and examples include alcohols such as methanol, ethanol, propanol, butanol and 2-propanol; straight-chain or cyclic saturated hydrocarbons such as pentane, hexane and cyclohexane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane, tetrahydrofuran and cyclopentyl methyl ether; esters such as ethyl acetate; nitriles such as acetonitrile and propionitrile; amides such as dimethylformamide and dimethylacetamide; ketones such as acetone and methyl ethyl ketone; and aprotic polar solvents such as dimethyl sulfoxide and 1,3-dimethyl-2-imidazolidinone; and water. One of these inert solvents may be used alone, and also two or more of them may be used as a mixture. The amount of the inert solvent used is usually selected as appropriate from the range of 0.1 to 100 L relative to 1 mol of the compound represented by the general formula (1a-2).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [h]

The compound represented by the general formula (1a) can be produced by reacting the compound represented by the general formula (1a-1) with the compound represented by the general formula (2-1) in the presence of a base and an inert solvent.

Examples of the base that can be used in this reaction include alkyllithiums such as methyllithium, n-butyllithium, sec-butyllithium and tert-butyllithium; organometallic compounds such as lithium hexamethyldisilazane and sodium hexamethyldisilazane; hydroxides such as lithium hydroxide, sodium hydroxide, potassium hydroxide and calcium hydroxide; carbonates such as lithium carbonate, lithium hydrogen carbonate, sodium carbonate, sodium hydrogen carbonate, potassium carbonate, potassium hydrogen carbonate, calcium carbonate and magnesium carbonate; acetates such as lithium acetate, sodium acetate and potassium acetate; alkoxides such as sodium methoxide, sodium ethoxide, sodium tert-butoxide and potassium tert-butoxide; metal hydrides such as sodium hydride and potassium hydride; and organic bases such as pyridine, picoline, lutidine, triethylamine, tributylamine and diisopropylethylamine. The amount of the base used is usually selected as appropriate from the range of a 1- to 5-fold molar amount relative to the compound represented by the general formula (1a-1).

The inert solvent used in this reaction may be any solvent that does not markedly inhibit the progress of the reaction, and examples include straight-chain or cyclic saturated hydrocarbons such as pentane, hexane and cyclohexane; aromatic hydrocarbons such as benzene, toluene and xylene; straight-chain or cyclic ethers such as diethyl ether, methyl tert-butyl ether, dioxane and tetrahydrofuran; and aprotic polar solvents such as N,N-dimethylformamide, N,N-dimethylacetamide, dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (1a-1).

Since this reaction is an equimolar reaction of the reactants, they are basically used in equimolar amounts, but either of them may be used in an excess amount. The reaction temperature is usually in the range of −78° C. to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method 2

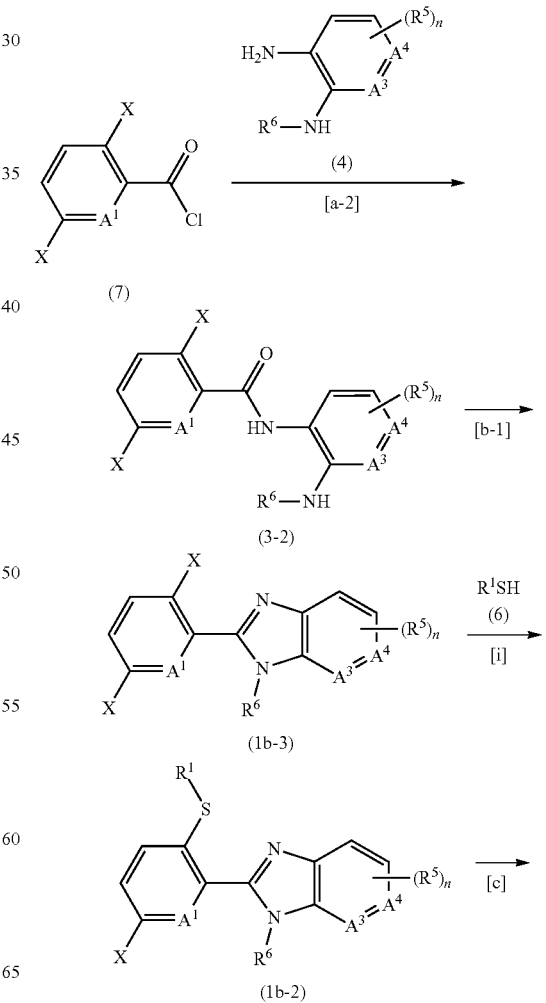

21

-continued

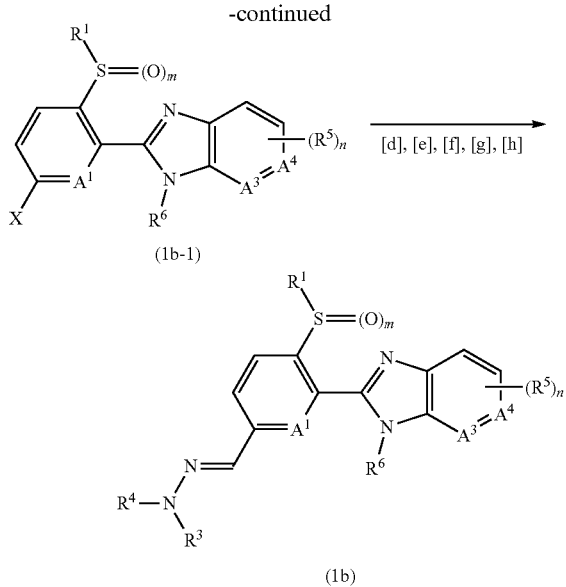

(1b-1)

(1b)

{In the formula, $R^1$, $R^3$, $R^4$, $R^5$, $R^6$, $A^1$, $A^3$, $A^4$, m, n and X are as defined above.}

The compound represented by the general formula (1b) of the present invention can be produced through the steps [a-2] and [i] described below and the steps [c], [b-1], [d], [e], [f], [g] and [h] corresponding to those described in Production Method 1 above.

Step [a-2]

A step of reacting the compound represented by the general formula (7) with the compound represented by the general formula (4) to produce the compound represented by the general formula (3-2).

Step [i]

A step of reacting the compound represented by the general formula (1b-3) with the compound represented by the general formula (6) to produce the compound represented by the general formula (1b-2).

Production Method at Step [a-2]

The compound represented by the general formula (3-2) can be produced by reacting the compound represented by the general formula (7) with the compound represented by the general formula (4) in the presence of a base and an inert solvent. The compound represented by the general formula (7) is derived from the corresponding carboxylic acid by the usual method used in organic synthesis.

Examples of the base that can be used in this reaction include inorganic bases such as sodium carbonate, potassium carbonate, sodium hydrogen carbonate and potassium hydrogen carbonate; acetates such as potassium acetate; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (7).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and aprotic polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (7).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [i]

The compound represented by the general formula (1b-2) can be produced by reacting the compound represented by the general formula (1b-3) with the compound represented by the general formula (6) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually selected as appropriate from the range of a 1- to 10-fold molar amount relative to the compound represented by the general formula (1b-3). In the case where an alkali metal salt of the compound represented by the general formula (6) is used, it is not necessary to use a base.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and aprotic polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (1b-3).

Since this reaction is an equimolar reaction of the reactants, they are basically used in equimolar amounts, but either of them may be used in an excess amount. The reaction temperature is usually in the range of −10° C. to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method 3

[Chem. 6]

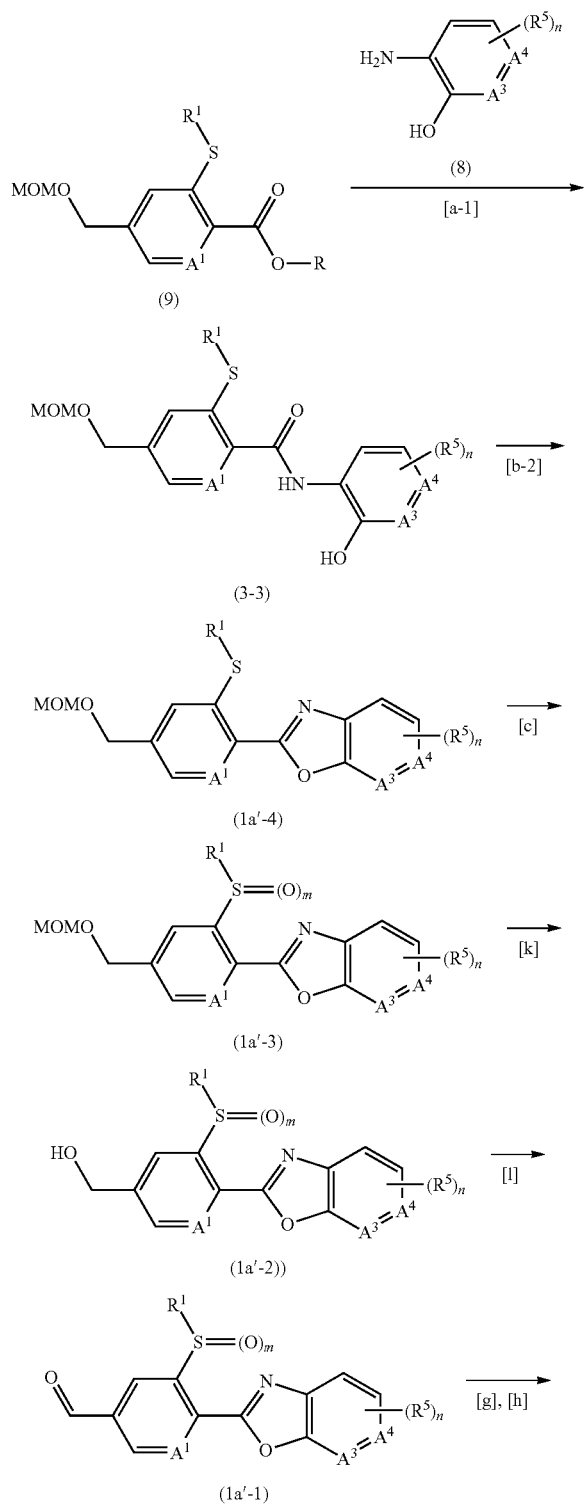

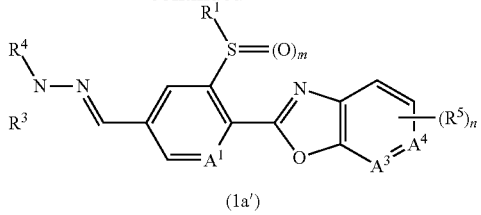

{In the formula, $R^1$, $R^3$, $R^4$, $R^5$, R, $A^1$, $A^3$, $A^4$, m and n are as defined above, and MOM stands for methoxymethyl.}

The compound represented by the general formula (1a') of the present invention can be produced through the steps [b-2], [k] and [l] described below and the steps [a-1], [c], [g] and [h] corresponding to those described in Production Method 1 above.

Step [k]

A step of removing the MOM protecting group of the compound represented by the general formula (1a'-3) to produce the compound represented by the formula (1a'-2).

Step [l]

A step of oxidizing the hydroxyl group of the compound represented by the general formula (1a'-2) to produce the compound represented by the general formula (1a'-1).

Production Method at Step [b-2]

The compound represented by the general formula (1a'-4) can be produced by intramolecularly cyclizing the amide compound represented by the general formula (3-3).

Examples of the acid that can be used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is usually selected as appropriate from the range of a 0.01- to 10-fold molar amount relative to the amide compound represented by the general formula (3-3).

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and aprotic polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (3-3).

The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [k]

The compound represented by the general formula (1a'-2) can be produced by removing the MOM protecting group of the compound represented by the general formula (1a'-3) according to the method described in Greene's Protective GROUPS in Organic SYNTHESIS (4th Edition).

Production Method at Step [l]

The compound represented by the general formula (1a'-1) can be produced from the compound represented by the general formula (1a'-2) by converting the hydroxymethyl group to a formyl group according to the method described in Synthesis 1996, 1153.

Production Method 4

[Chem. 27]

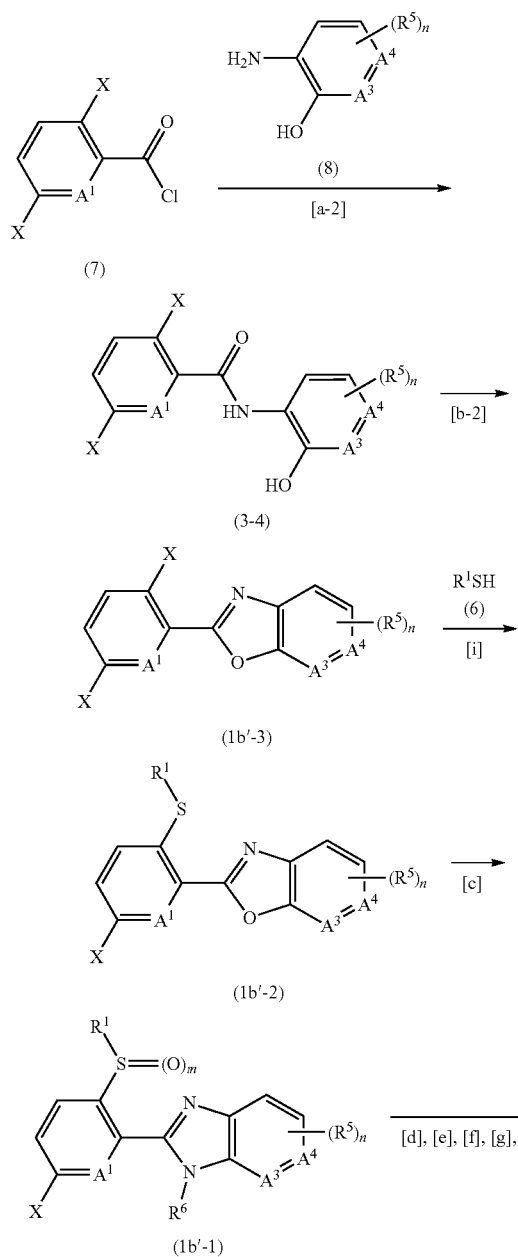

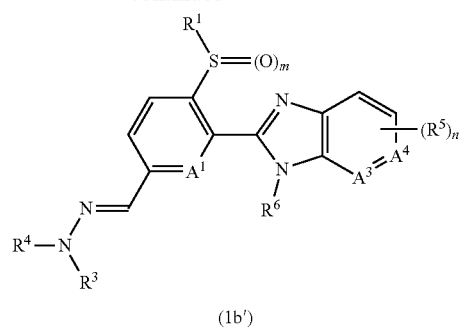

{In the formula, $R^1$, $R^3$, $R^4$, $R^5$, $R^6$, $A^1$, $A^3$, $A^4$, X, m and n are as defined above.}

The compound represented by the general formula (1b') of the present invention can be produced in the same manner as described in the steps [a-2], [b-2], [c], [d], [e], [f], [g], [h] and [i] of Production Methods 1, 2 and 3 above.

Intermediate Production Method 1

[Chem. 8]

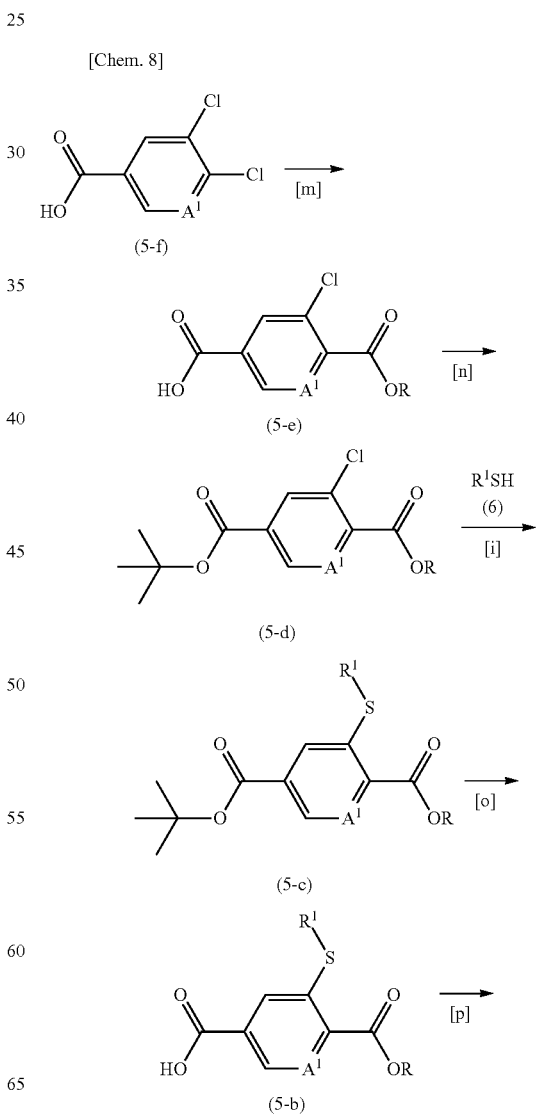

-continued

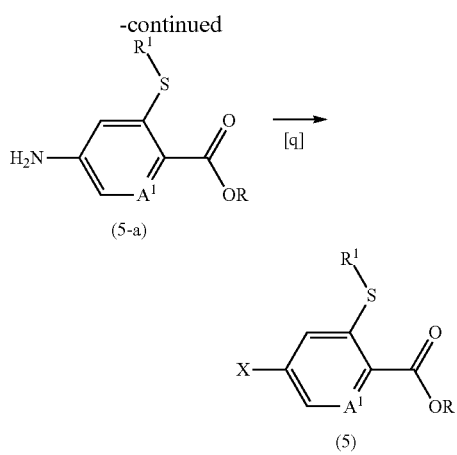

(In the formula, $R^1$, $A^1$, R and X are as defined above.)

The intermediate represented by the general formula (5) can be produced through the steps [m], [n], [o], [p] and [q] described below and the step [i] of Production Method 2 above.

Step [m]
A step of converting a halogen atom of the compound represented by the general formula (5-f) to an ester group via the Heck reaction to produce the compound represented by the general formula (5-e).

Step [n]
A step of protecting the carboxyl group of the compound represented by the general formula (5-e) by tert-butyl esterification to produce the compound represented by the general formula (5-d).

Step [o]
A step of deprotecting the carboxyl group protected by tert-butyl esterification in the compound represented by the general formula (5-c) to produce the compound represented by the general formula (5-b).

Step [p]
A step of converting the carboxyl group of the compound represented by the general formula (5-b) to an amino group via the Curtius rearrangement to produce the compound represented by the general formula (5-a).

Step [q]
A step of converting the amino group of the compound represented by the general formula (5-a) to a halogen atom via the Sandmeyer reaction to produce the compound represented by the general formula (5).

Production Method at Step [m]
The compound represented by the general formula (5-e) can be produced by subjecting the compound represented by formula (5-f), which is commercially available, to the reaction as described in JP-A 2005-272338 (Heck reaction). After the reaction is completed, the compound of interest is isolated from the post-reaction mixture by the usual method. If desired, recrystallization, column chromatography, etc. can be employed for the purification of the compound of interest.

Production Method at Step [n]
Firstly, the compound represented by the general formula (5-e) is reacted with a chlorinating agent in the presence of an inert solvent according to the usual method used in organic synthesis to yield the corresponding acid chloride. The acid chloride is then reacted with a tert-butyl alcohol in the presence of a base and an inert solvent to yield the compound represented by the general formula (5-d).

Production Method at Step [o]
The compound represented by the general formula (5-b) can be produced by hydrolyzing the compound represented by the general formula (5-c) in the presence of an acid and/or an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1-to 10-fold molar amount relative to the compound represented by the general formula (2-c). In some cases, the acid can be used to serve as the solvent as well.

The inert solvent used in this reaction may be any solvent that does not markedly inhibit the progress of the reaction, and examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; aprotic polar solvents such as dimethyl sulfoxide and 1,3-dimethyl-2-imidazolidinone; and water. One of these inert solvents may be used alone, and also two or more of them may be used as a mixture. The amount of the inert solvent used is usually selected as appropriate from the range of 0.1 to 100 L relative to 1 mol of the compound represented by the general formula (5-c). In the case where the acid is used as the solvent, it is not necessary to use another solvent.

The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [p]
The compound represented by the general formula (5-b) is reacted with DPPA (diphenylphosphoryl azide) in the presence of a base and a tert-butyl alcohol according to the method described in J. A. Chem. Soc. 1972, 94, 6203-6205. Subsequently, the resulting compound is hydrolyzed under acid conditions to yield the compound represented by the general formula (5-a). After the reaction is completed, the compound of interest is isolated from the post-reaction mixture by the usual method. As needed, recrystallization, column chromatography, etc. can be employed for the purification of the compound of interest.

Production Method at Step [q]
The intermediate represented by the general formula (5) can be produced by subjecting the compound represented by the general formula (5-a) to the Sandmeyer reaction as described in Chem. Rev. 1988, 88, 765. After the reaction is completed, the compound of interest is isolated from the post-reaction mixture by the usual method. As needed, recrystallization, column chromatography, etc. can be employed for the purification of the compound of interest.

Intermediate Production Method 2

[Chem. 9]

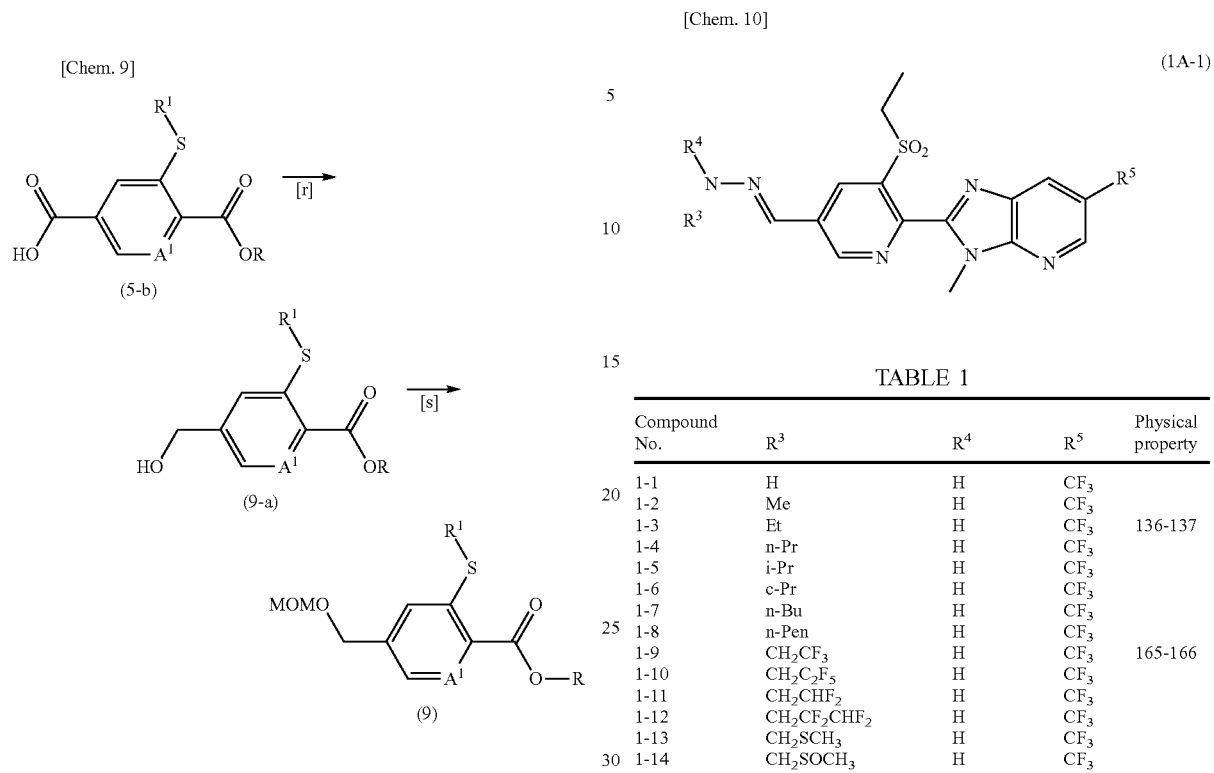

[Chem. 10]

(In the formula, $R^1$, R, MOM and $A^1$ are as defined above.)

The intermediate represented by the general formula (9) can be produced through the steps [r] and [s] described below.

Step [r]

A step of reducing the carboxyl group of the compound represented by the general formula (5-b) to produce the compound represented by the general formula (9-a).

Step [s]

A step of protecting the hydroxyl group of the compound represented by the general formula (9-a) with a MOM group to produce the compound represented by the general formula (9).

Production Methods at Steps [r] and [s]

The compound represented by the general formula (5-b) produced according to Intermediate Production Method 1 above is reduced according to the reducing method described in WO 2014/068988 to yield the compound represented by the general formula (9-a). The hydroxyl group of the compound represented by the general formula (9-a) is protected with a MOM group according to the method described in Greene's Protective GROUPS in Organic SYNTHESIS (4th Edition) to yield the intermediate represented by the general formula (9).

Specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, n-Bu stands for a n-butyl group, n-Pen stands for a n-pentyl group, Ph stands for a phenyl group, Bn stands for a benzyl group, and Ac stands for an acetyl group. Shown in the column of "Physical property" is a melting point (° C.) or "NMR". NMR data are shown in Table 5.

TABLE 1

| Compound No. | $R^3$ | $R^4$ | $R^5$ | Physical property |
|---|---|---|---|---|
| 1-1 | H | H | $CF_3$ | |
| 1-2 | Me | H | $CF_3$ | |
| 1-3 | Et | H | $CF_3$ | 136-137 |
| 1-4 | n-Pr | H | $CF_3$ | |
| 1-5 | i-Pr | H | $CF_3$ | |
| 1-6 | c-Pr | H | $CF_3$ | |
| 1-7 | n-Bu | H | $CF_3$ | |
| 1-8 | n-Pen | H | $CF_3$ | |
| 1-9 | $CH_2CF_3$ | H | $CF_3$ | 165-166 |
| 1-10 | $CH_2C_2F_5$ | H | $CF_3$ | |
| 1-11 | $CH_2CHF_2$ | H | $CF_3$ | |
| 1-12 | $CH_2CF_2CHF_2$ | H | $CF_3$ | |
| 1-13 | $CH_2SCH_3$ | H | $CF_3$ | |
| 1-14 | $CH_2SOCH_3$ | H | $CF_3$ | |
| 1-15 | $CH_2SO_2CH_3$ | H | $CF_3$ | |
| 1-16 | $CH_2SCH_2CH_3$ | H | $CF_3$ | |
| 1-17 | $CH_2SOCH_2CH_3$ | H | $CF_3$ | |
| 1-18 | $CH_2SO_2CH_2CH_3$ | H | $CF_3$ | |
| 1-19 | $CH_2CH_2SCH_3$ | H | $CF_3$ | |
| 1-20 | $CH_2CH_2SOCH_3$ | H | $CF_3$ | |
| 1-21 | $CH_2CH_2SO_2CH_3$ | H | $CF_3$ | |
| 1-22 | $CH_2CH_2SCH_2CH_3$ | H | $CF_3$ | |
| 1-23 | $CH_2CH_2SOCH_2CH_3$ | H | $CF_3$ | |
| 1-24 | $CH_2CH_2SO_2CH_2CH_3$ | H | $CF_3$ | |
| 1-25 | $CH_2CH_2SCF_3$ | H | $CF_3$ | |
| 1-26 | $CH_2CH_2SOCF_3$ | H | $CF_3$ | |
| 1-27 | $CH_2CH_2SO_2CF_3$ | H | $CF_3$ | |
| 1-28 | $CH_2Ph$ | H | $CF_3$ | |
| 1-29 | $CH_2C\equiv CH$ | H | $CF_3$ | |
| 1-30 | $CH_2C\equiv CCH_3$ | H | $CF_3$ | |
| 1-31 | $CH_2C\equiv N$ | H | $CF_3$ | |
| 1-32 | $CH_2CH=CH_2$ | H | $CF_3$ | |
| 1-33 | $CH_2CH=CHCH_3$ | H | $CF_3$ | |
| 1-34 | $CH_2CH=C(CH_3)_3$ | H | $CF_3$ | |
| 1-35 | $CH_2OCH_3$ | H | $CF_3$ | |
| 1-36 | $CH_2CH_2OCH_3$ | H | $CF_3$ | |
| 1-37 | $CH_2OCH_2CH_3$ | H | $CF_3$ | |
| 1-38 | $CH_2CH_2OCH_2CH_3$ | H | $CF_3$ | |
| 1-39 | Ph | H | $CF_3$ | |
| 1-40 | 4-SMePh | H | $CF_3$ | 231-232 |
| 1-41 | 4-$CF_3$Ph | H | $CF_3$ | 224-225 |
| 1-42 | 2-F,4-Cl—Ph | H | $CF_3$ | 249-250 |
| 1-43 | Me | Me | $CF_3$ | |
| 1-44 | Et | Me | $CF_3$ | |
| 1-45 | n-Pr | Me | $CF_3$ | |
| 1-46 | i-Pr | Me | $CF_3$ | |
| 1-47 | c-Pr | Me | $CF_3$ | |
| 1-48 | n-Bu | Me | $CF_3$ | |
| 1-49 | n-Pen | Me | $CF_3$ | |
| 1-50 | $CH_2CF_3$ | Me | $CF_3$ | NMR |
| 1-51 | $CH_2C_2F_5$ | Me | $CF_3$ | |
| 1-52 | $CH_2CHF_2$ | Me | $CF_3$ | |
| 1-53 | $CH_2CF_2CHF_2$ | Me | $CF_3$ | |
| 1-54 | $CH_2SCH_3$ | Me | $CF_3$ | |
| 1-55 | $CH_2SOCH_3$ | Me | $CF_3$ | |
| 1-56 | $CH_2SO_2CH_3$ | Me | $CF_3$ | |
| 1-57 | $CH_2SCH_2CH_3$ | Me | $CF_3$ | |
| 1-58 | $CH_2SOCH_2CH_3$ | Me | $CF_3$ | |
| 1-59 | $CH_2SO_2CH_2CH_3$ | Me | $CF_3$ | |

TABLE 1-continued

| Compound No. | R³ | R⁴ | R⁵ | Physical property |
|---|---|---|---|---|
| 1-60 | CH₂CH₂SCH₃ | Me | CF₃ | |
| 1-61 | CH₂CH₂SOCH₃ | Me | CF₃ | |
| 1-62 | CH₂CH₂SO₂CH₃ | Me | CF₃ | |
| 1-63 | CH₂CH₂SCH₂CH₃ | Me | CF₃ | |
| 1-64 | CH₂CH₂SOCH₂CH₃ | Me | CF₃ | |
| 1-65 | CH₂CH₂SO₂CH₂CH₃ | Me | CF₃ | |
| 1-66 | CH₂CH₂SCF₃ | Me | CF₃ | |
| 1-67 | CH₂CH₂SOCF₃ | Me | CF₃ | |
| 1-68 | CH₂CH₂SO₂CF₃ | Me | CF₃ | |
| 1-69 | CH₂Ph | Me | CF₃ | |
| 1-70 | CH₂C≡CH | Me | CF₃ | |
| 1-71 | CH₂C≡CCH₃ | Me | CF₃ | |
| 1-72 | CH₂C≡N | Me | CF₃ | |
| 1-73 | CH₂CH═CH₂ | Me | CF₃ | |
| 1-74 | CH₂CH═CHCH₃ | Me | CF₃ | |
| 1-75 | CH₂CH═C(CH₃)₃ | Me | CF₃ | |
| 1-76 | CH₂OCH₃ | Me | CF₃ | |
| 1-77 | CH₂CH₂OCH₃ | Me | CF₃ | |
| 1-78 | CH₂OCH₂CH₃ | Me | CF₃ | |
| 1-79 | CH₂CH₂OCH₂CH₃ | Me | CF₃ | |
| 1-80 | Et | Et | CF₃ | |
| 1-81 | n-Pr | Et | CF₃ | |
| 1-82 | i-Pr | Et | CF₃ | |
| 1-83 | c-Pr | Et | CF₃ | |
| 1-84 | n-Bu | Et | CF₃ | |
| 1-85 | n-Pen | Et | CF₃ | |
| 1-86 | CH₂CF₃ | Et | CF₃ | 138-139 |
| 1-87 | CH₂C₂F₅ | Et | CF₃ | |
| 1-88 | CH₂CHF₂ | Et | CF₃ | |
| 1-89 | CH₂CF₂CHF₂ | Et | CF₃ | NMR |
| 1-90 | CH₂SCH₃ | Et | CF₃ | |
| 1-91 | CH₂SOCH₃ | Et | CF₃ | |
| 1-92 | CH₂SO₂CH₃ | Et | CF₃ | |
| 1-93 | CH₂SCH₂CH₃ | Et | CF₃ | |
| 1-94 | CH₂SOCH₂CH₃ | Et | CF₃ | |
| 1-95 | CH₂SO₂CH₂CH₃ | Et | CF₃ | |
| 1-96 | CH₂CH₂SCH₃ | Et | CF₃ | |
| 1-97 | CH₂CH₂SOCH₃ | Et | CF₃ | |
| 1-98 | CH₂CH₂SO₂CH₃ | Et | CF₃ | |
| 1-99 | CH₂CH₂SCH₂CH₃ | Et | CF₃ | |
| 1-100 | CH₂CH₂SOCH₂CH₃ | Et | CF₃ | |
| 1-101 | CH₂CH₂SO₂CH₂CH₃ | Et | CF₃ | |
| 1-102 | CH₂CH₂SCF₃ | Et | CF₃ | |
| 1-103 | CH₂CH₂SOCF₃ | Et | CF₃ | |
| 1-104 | CH₂CH₂SO₂CF₃ | Et | CF₃ | |
| 1-105 | CH₂Ph | Et | CF₃ | |
| 1-106 | CH₂C≡CH | Et | CF₃ | |
| 1-107 | CH₂C≡CCH₃ | Et | CF₃ | |
| 1-108 | CH₂C≡N | Et | CF₃ | |
| 1-109 | CH₂CH═CH₂ | Et | CF₃ | |
| 1-110 | CH₂CH═CHCH₃ | Et | CF₃ | |
| 1-111 | CH₂CH═C(CH₃)₃ | Et | CF₃ | |
| 1-112 | CH₂OCH₃ | Et | CF₃ | |
| 1-113 | CH₂CH₂OCH₃ | Et | CF₃ | |
| 1-114 | CH₂OCH₂CH₃ | Et | CF₃ | |
| 1-115 | CH₂CH₂OCH₂CH₃ | Et | CF₃ | |
| 1-116 | H | Ac | CF₃ | 254-255 |
| 1-117 | Me | Ac | CF₃ | |
| 1-118 | Et | Ac | CF₃ | 209-210 |
| 1-119 | n-Pr | Ac | CF₃ | |
| 1-120 | i-Pr | Ac | CF₃ | |
| 1-121 | c-Pr | Ac | CF₃ | |
| 1-122 | n-Bu | Ac | CF₃ | |
| 1-123 | n-Pen | Ac | CF₃ | |
| 1-124 | CH₂CF₃ | Ac | CF₃ | 239-240 |
| 1-125 | CH₂C₂F₅ | Ac | CF₃ | |
| 1-126 | CH₂CHF₂ | Ac | CF₃ | |
| 1-127 | CH₂CF₂CHF₂ | Ac | CF₃ | |
| 1-128 | CH₂SCH₃ | Ac | CF₃ | |
| 1-129 | CH₂SOCH₃ | Ac | CF₃ | |
| 1-130 | CH₂SO₂CH₃ | Ac | CF₃ | |
| 1-131 | CH₂SCH₂CH₃ | Ac | CF₃ | |
| 1-132 | CH₂SOCH₂CH₃ | Ac | CF₃ | |
| 1-133 | CH₂SO₂CH₂CH₃ | Ac | CF₃ | |
| 1-134 | CH₂CH₂SCH₃ | Ac | CF₃ | |
| 1-135 | CH₂CH₂SOCH₃ | Ac | CF₃ | |
| 1-136 | CH₂CH₂SO₂CH₃ | Ac | CF₃ | |
| 1-137 | CH₂CH₂SCH₂CH₃ | Ac | CF₃ | |
| 1-138 | CH₂CH₂SOCH₂CH₃ | Ac | CF₃ | |
| 1-139 | CH₂CH₂SO₂CH₂CH₃ | Ac | CF₃ | |
| 1-140 | CH₂CH₂SCF₃ | Ac | CF₃ | |
| 1-141 | CH₂CH₂SOCF₃ | Ac | CF₃ | |
| 1-142 | CH₂CH₂SO₂CF₃ | Ac | CF₃ | |
| 1-143 | CH₂Ph | Ac | CF₃ | |
| 1-144 | CH₂C≡CH | Ac | CF₃ | |
| 1-145 | CH₂C≡CCH₃ | Ac | CF₃ | |
| 1-146 | CH₂C≡N | Ac | CF₃ | |
| 1-147 | CH₂CH═CH₂ | Ac | CF₃ | |
| 1-148 | CH₂CH═CHCH₃ | Ac | CF₃ | |
| 1-149 | CH₂CH═C(CH₃)₃ | Ac | CF₃ | |
| 1-150 | CH₂OCH₃ | Ac | CF₃ | |
| 1-151 | CH₂CH₂OCH₃ | Ac | CF₃ | |
| 1-152 | CH₂OCH₂CH₃ | Ac | CF₃ | |
| 1-153 | CH₂CH₂OCH₂CH₃ | Ac | CF₃ | |
| 1-154 | H | CO₂Me | CF₃ | 230-231 |
| 1-155 | Me | CO₂Me | CF₃ | |
| 1-156 | Et | CO₂Me | CF₃ | 198-199 |
| 1-157 | n-Pr | CO₂Me | CF₃ | |
| 1-158 | i-Pr | CO₂Me | CF₃ | |
| 1-159 | c-Pr | CO₂Me | CF₃ | |
| 1-160 | n-Bu | CO₂Me | CF₃ | |
| 1-161 | n-Pen | CO₂Me | CF₃ | |
| 1-162 | CH₂CF₃ | CO₂Me | CF₃ | |
| 1-163 | CH₂C₂F₅ | CO₂Me | CF₃ | |
| 1-164 | CH₂CHF₂ | CO₂Me | CF₃ | |
| 1-165 | CH₂CF₂CHF₂ | CO₂Me | CF₃ | |
| 1-166 | CH₂SCH₃ | CO₂Me | CF₃ | |
| 1-167 | CH₂SOCH₃ | CO₂Me | CF₃ | |
| 1-168 | CH₂SO₂CH₃ | CO₂Me | CF₃ | |
| 1-169 | CH₂SCH₂CH₃ | CO₂Me | CF₃ | |
| 1-170 | CH₂SOCH₂CH₃ | CO₂Me | CF₃ | |
| 1-171 | CH₂SO₂CH₂CH₃ | CO₂Me | CF₃ | |
| 1-172 | CH₂CH₂SCH₃ | CO₂Me | CF₃ | |
| 1-173 | CH₂CH₂SOCH₃ | CO₂Me | CF₃ | |
| 1-174 | CH₂CH₂SO₂CH₃ | CO₂Me | CF₃ | |
| 1-175 | CH₂CH₂SCH₂CH₃ | CO₂Me | CF₃ | |
| 1-176 | CH₂CH₂SOCH₂CH₃ | CO₂Me | CF₃ | |
| 1-177 | CH₂CH₂SO₂CH₂CH₃ | CO₂Me | CF₃ | |
| 1-178 | CH₂CH₂SCF₃ | CO₂Me | CF₃ | |
| 1-179 | CH₂CH₂SOCF₃ | CO₂Me | CF₃ | |
| 1-180 | CH₂CH₂SO₂CF₃ | CO₂Me | CF₃ | |
| 1-181 | CH₂Ph | CO₂Me | CF₃ | |
| 1-182 | CH₂C≡CH | CO₂Me | CF₃ | |
| 1-183 | CH₂C≡CCH₃ | CO₂Me | CF₃ | |
| 1-184 | CH₂C≡N | CO₂Me | CF₃ | |
| 1-185 | CH₂CH═CH₂ | CO₂Me | CF₃ | |
| 1-186 | CH₂CH═CHCH₃ | CO₂Me | CF₃ | |
| 1-187 | CH₂CH═C(CH₃)₃ | CO₂Me | CF₃ | |
| 1-188 | CH₂OCH₃ | CO₂Me | CF₃ | |
| 1-189 | CH₂CH₂OCH₃ | CO₂Me | CF₃ | |
| 1-190 | CH₂OCH₂CH₃ | CO₂Me | CF₃ | |
| 1-191 | CH₂CH₂OCH₂CH₃ | CO₂Me | CF₃ | |
| 1-192 | H | CO₂Et | CF₃ | |
| 1-193 | Me | CO₂Et | CF₃ | |
| 1-194 | Et | CO₂Et | CF₃ | |
| 1-195 | n-Pr | CO₂Et | CF₃ | |
| 1-196 | i-Pr | CO₂Et | CF₃ | |
| 1-197 | c-Pr | CO₂Et | CF₃ | |
| 1-198 | n-Bu | CO₂Et | CF₃ | |
| 1-199 | n-Pen | CO₂Et | CF₃ | |
| 1-200 | CH₂CF₃ | CO₂Et | CF₃ | |
| 1-201 | CH₂C₂F₅ | CO₂Et | CF₃ | |
| 1-202 | CH₂CHF₂ | CO₂Et | CF₃ | |
| 1-203 | CH₂CF₂CHF₂ | CO₂Et | CF₃ | |
| 1-204 | CH₂SCH₃ | CO₂Et | CF₃ | |
| 1-205 | CH₂SOCH₃ | CO₂Et | CF₃ | |
| 1-206 | CH₂SO₂CH₃ | CO₂Et | CF₃ | |
| 1-207 | CH₂SCH₂CH₃ | CO₂Et | CF₃ | |
| 1-208 | CH₂SOCH₂CH₃ | CO₂Et | CF₃ | |
| 1-209 | CH₂SO₂CH₂CH₃ | CO₂Et | CF₃ | |
| 1-210 | CH₂CH₂SCH₃ | CO₂Et | CF₃ | |
| 1-211 | CH₂CH₂SOCH₃ | CO₂Et | CF₃ | |
| 1-212 | CH₂CH₂SO₂CH₃ | CO₂Et | CF₃ | |
| 1-213 | CH₂CH₂SCH₂CH₃ | CO₂Et | CF₃ | |

TABLE 1-continued

| Compound No. | R³ | R⁴ | R⁵ | Physical property |
|---|---|---|---|---|
| 1-214 | CH₂CH₂SOCH₂CH₃ | CO₂Et | CF₃ | |
| 1-215 | CH₂CH₂SO₂CH₂CH₃ | CO₂Et | CF₃ | |
| 1-216 | CH₂CH₂SCF₃ | CO₂Et | CF₃ | |
| 1-217 | CH₂CH₂SOCF₃ | CO₂Et | CF₃ | |
| 1-218 | CH₂CH₂SO₂CF₃ | CO₂Et | CF₃ | |
| 1-219 | CH₂Ph | CO₂Et | CF₃ | |
| 1-220 | CH₂C≡CH | CO₂Et | CF₃ | |
| 1-221 | CH₂C≡CCH₃ | CO₂Et | CF₃ | |
| 1-222 | CH₂C≡N | CO₂Et | CF₃ | |
| 1-223 | CH₂CH=CH₂ | CO₂Et | CF₃ | |
| 1-224 | CH₂CH=CHCH₃ | CO₂Et | CF₃ | |
| 1-225 | CH₂CH=C(CH₃)₃ | CO₂Et | CF₃ | |
| 1-226 | CH₂OCH₃ | CO₂Et | CF₃ | |
| 1-227 | CH₂CH₂OCH₃ | CO₂Et | CF₃ | |
| 1-228 | CH₂OCH₂CH₃ | CO₂Et | CF₃ | |
| 1-229 | CH₂CH₂OCH₂CH₃ | CO₂Et | CF₃ | |
| 1-230 | H | COCF₃ | CF₃ | |
| 1-231 | Me | COCF₃ | CF₃ | |
| 1-232 | Et | COCF₃ | CF₃ | |
| 1-233 | n-Pr | COCF₃ | CF₃ | |
| 1-234 | i-Pr | COCF₃ | CF₃ | |
| 1-235 | c-Pr | COCF₃ | CF₃ | |
| 1-236 | n-Bu | COCF₃ | CF₃ | |
| 1-237 | n-Pen | COCF₃ | CF₃ | |
| 1-238 | CH₂CF₃ | COCF₃ | CF₃ | |
| 1-239 | CH₂C₂F₅ | COCF₃ | CF₃ | |
| 1-240 | CH₂CHF₂ | COCF₃ | CF₃ | |
| 1-241 | CH₂CF₂CHF₂ | COCF₃ | CF₃ | |
| 1-242 | CH₂SCH₃ | COCF₃ | CF₃ | |
| 1-243 | CH₂SOCH₃ | COCF₃ | CF₃ | |
| 1-244 | CH₂SO₂CH₃ | COCF₃ | CF₃ | |
| 1-245 | CH₂SCH₂CH₃ | COCF₃ | CF₃ | |
| 1-246 | CH₂SOCH₂CH₃ | COCF₃ | CF₃ | |
| 1-247 | CH₂SO₂CH₂CH₃ | COCF₃ | CF₃ | |
| 1-248 | CH₂CH₂SCH₃ | COCF₃ | CF₃ | |
| 1-249 | CH₂CH₂SOCH₃ | COCF₃ | CF₃ | |
| 1-250 | CH₂CH₂SO₂CH₃ | COCF₃ | CF₃ | |
| 1-251 | CH₂CH₂SCH₂CH₃ | COCF₃ | CF₃ | |
| 1-252 | CH₂CH₂SOCH₂CH₃ | COCF₃ | CF₃ | |
| 1-253 | CH₂CH₂SO₂CH₂CH₃ | COCF₃ | CF₃ | |
| 1-254 | CH₂CH₂SCF₃ | COCF₃ | CF₃ | |
| 1-255 | CH₂CH₂SOCF₃ | COCF₃ | CF₃ | |
| 1-256 | CH₂CH₂SO₂CF₃ | COCF₃ | CF₃ | |
| 1-257 | CH₂Ph | COCF₃ | CF₃ | |
| 1-258 | CH₂C≡CH | COCF₃ | CF₃ | |
| 1-259 | CH₂C≡CCH₃ | COCF₃ | CF₃ | |
| 1-260 | CH₂C≡N | COCF₃ | CF₃ | |
| 1-261 | CH₂CH=CH₂ | COCF₃ | CF₃ | |
| 1-262 | CH₂CH=CHCH₃ | COCF₃ | CF₃ | |
| 1-263 | CH₂CH=C(CH₃)₃ | COCF₃ | CF₃ | |
| 1-264 | CH₂OCH₃ | COCF₃ | CF₃ | |
| 1-265 | CH₂CH₂OCH₃ | COCF₃ | CF₃ | |
| 1-266 | CH₂OCH₂CH₃ | COCF₃ | CF₃ | |
| 1-267 | CH₂CH₂OCH₂CH₃ | COCF₃ | CF₃ | |
| 1-268 | H | COCF₃ | CF₃ | |
| 1-269 | Me | CSOMe | CF₃ | |
| 1-270 | Et | CSOMe | CF₃ | |
| 1-271 | n-Pr | CSOMe | CF₃ | |
| 1-272 | i-Pr | CSOMe | CF₃ | |
| 1-273 | c-Pr | CSOMe | CF₃ | |
| 1-274 | n-Bu | CSOMe | CF₃ | |
| 1-275 | n-Pen | CSOMe | CF₃ | |
| 1-276 | CH₂CF₃ | CSOMe | CF₃ | |
| 1-277 | CH₂C₂F₅ | CSOMe | CF₃ | |
| 1-278 | CH₂CHF₂ | CSOMe | CF₃ | |
| 1-279 | CH₂CF₂CHF₂ | CSOMe | CF₃ | |
| 1-280 | CH₂SCH₃ | CSOMe | CF₃ | |
| 1-281 | CH₂SOCH₃ | CSOMe | CF₃ | |
| 1-282 | CH₂SO₂CH₃ | CSOMe | CF₃ | |
| 1-283 | CH₂SCH₂CH₃ | CSOMe | CF₃ | |
| 1-284 | CH₂SOCH₂CH₃ | CSOMe | CF₃ | |
| 1-285 | CH₂SO₂CH₂CH₃ | CSOMe | CF₃ | |
| 1-286 | CH₂CH₂SCH₃ | CSOMe | CF₃ | |
| 1-287 | CH₂CH₂SOCH₃ | CSOMe | CF₃ | |
| 1-288 | CH₂CH₂SO₂CH₃ | CSOMe | CF₃ | |
| 1-289 | CH₂CH₂SCH₂CH₃ | CSOMe | CF₃ | |
| 1-290 | CH₂CH₂SOCH₂CH₃ | CSOMe | CF₃ | |
| 1-291 | CH₂CH₂SO₂CH₂CH₃ | CSOMe | CF₃ | |
| 1-292 | CH₂CH₂SCF₃ | CSOMe | CF₃ | |
| 1-293 | CH₂CH₂SOCF₃ | CSOMe | CF₃ | |
| 1-294 | CH₂CH₂SO₂CF₃ | CSOMe | CF₃ | |
| 1-295 | CH₂Ph | CSOMe | CF₃ | |
| 1-296 | CH₂C≡CH | CSOMe | CF₃ | |
| 1-297 | CH₂C≡CCH₃ | CSOMe | CF₃ | |
| 1-298 | CH₂C≡N | CSOMe | CF₃ | |
| 1-299 | CH₂CH=CH₂ | CSOMe | CF₃ | |
| 1-300 | CH₂CH=CHCH₃ | CSOMe | CF₃ | |
| 1-301 | CH₂CH=C(CH₃)₃ | CSOMe | CF₃ | |
| 1-302 | CH₂OCH₃ | CSOMe | CF₃ | |
| 1-303 | CH₂CH₂OCH₃ | CSOMe | CF₃ | |
| 1-304 | CH₂OCH₂CH₃ | CSOMe | CF₃ | |
| 1-305 | CH₂CH₂OCH₂CH₃ | CSOMe | CF₃ | |
| 1-306 | H | CSOEt | CF₃ | 234-235 |
| 1-307 | Me | CSOEt | CF₃ | |
| 1-308 | Et | CSOEt | CF₃ | 196-197 |
| 1-309 | n-Pr | CSOEt | CF₃ | |
| 1-310 | i-Pr | CSOEt | CF₃ | |
| 1-311 | c-Pr | CSOEt | CF₃ | |
| 1-312 | n-Bu | CSOEt | CF₃ | |
| 1-313 | n-Pen | CSOEt | CF₃ | |
| 1-314 | CH₂CF₃ | CSOEt | CF₃ | |
| 1-315 | CH₂C₂F₅ | CSOEt | CF₃ | |
| 1-316 | CH₂CHF₂ | CSOEt | CF₃ | |
| 1-317 | CH₂CF₂CHF₂ | CSOEt | CF₃ | |
| 1-318 | CH₂SCH₃ | CSOEt | CF₃ | |
| 1-319 | CH₂SOCH₃ | CSOEt | CF₃ | |
| 1-320 | CH₂SO₂CH₃ | CSOEt | CF₃ | |
| 1-321 | CH₂SCH₂CH₃ | CSOEt | CF₃ | |
| 1-322 | CH₂SOCH₂CH₃ | CSOEt | CF₃ | |
| 1-323 | CH₂SO₂CH₂CH₃ | CSOEt | CF₃ | |
| 1-324 | CH₂CH₂SCH₃ | CSOEt | CF₃ | |
| 1-325 | CH₂CH₂SOCH₃ | CSOEt | CF₃ | |
| 1-326 | CH₂CH₂SO₂CH₃ | CSOEt | CF₃ | |
| 1-327 | CH₂CH₂SCH₂CH₃ | CSOEt | CF₃ | |
| 1-328 | CH₂CH₂SOCH₂CH₃ | CSOEt | CF₃ | |
| 1-329 | CH₂CH₂SO₂CH₂CH₃ | CSOEt | CF₃ | |
| 1-330 | CH₂CH₂SCF₃ | CSOEt | CF₃ | |
| 1-331 | CH₂CH₂SOCF₃ | CSOEt | CF₃ | |
| 1-332 | CH₂CH₂SO₂CF₃ | CSOEt | CF₃ | |
| 1-333 | CH₂Ph | CSOEt | CF₃ | |
| 1-334 | CH₂C≡CH | CSOEt | CF₃ | |
| 1-335 | CH₂C≡CCH₃ | CSOEt | CF₃ | |
| 1-336 | CH₂C≡N | CSOEt | CF₃ | |
| 1-337 | CH₂CH=CH₂ | CSOEt | CF₃ | |
| 1-338 | CH₂CH=CHCH₃ | CSOEt | CF₃ | |
| 1-339 | CH₂CH=C(CH₃)₃ | CSOEt | CF₃ | |
| 1-340 | CH₂OCH₃ | CSOEt | CF₃ | |
| 1-341 | CH₂CH₂OCH₃ | CSOEt | CF₃ | |
| 1-342 | CH₂OCH₂CH₃ | CSOEt | CF₃ | |
| 1-343 | CH₂CH₂OCH₂CH₃ | CSOEt | CF₃ | |
| 1-344 | H | CSN(Me)₂ | CF₃ | |
| 1-345 | Me | CSN(Me)₂ | CF₃ | |
| 1-346 | Et | CSN(Me)₂ | CF₃ | 71-72 |
| 1-347 | n-Pr | CSN(Me)₂ | CF₃ | |
| 1-348 | i-Pr | CSN(Me)₂ | CF₃ | |
| 1-349 | c-Pr | CSN(Me)₂ | CF₃ | |
| 1-350 | n-Bu | CSN(Me)₂ | CF₃ | |
| 1-351 | n-Pen | CSN(Me)₂ | CF₃ | |
| 1-352 | CH₂CF₃ | CSN(Me)₂ | CF₃ | |
| 1-353 | CH₂C₂F₅ | CSN(Me)₂ | CF₃ | |
| 1-354 | CH₂CHF₂ | CSN(Me)₂ | CF₃ | |
| 1-355 | CH₂CF₂CHF₂ | CSN(Me)₂ | CF₃ | |
| 1-356 | CH₂SCH₃ | CSN(Me)₂ | CF₃ | |
| 1-357 | CH₂SOCH₃ | CSN(Me)₂ | CF₃ | |
| 1-358 | CH₂SO₂CH₃ | CSN(Me)₂ | CF₃ | |
| 1-359 | CH₂SCH₂CH₃ | CSN(Me)₂ | CF₃ | |
| 1-360 | CH₂SOCH₂CH₃ | CSN(Me)₂ | CF₃ | |
| 1-361 | CH₂SO₂CH₂CH₃ | CSN(Me)₂ | CF₃ | |
| 1-362 | CH₂CH₂SCH₃ | CSN(Me)₂ | CF₃ | |
| 1-363 | CH₂CH₂SOCH₃ | CSN(Me)₂ | CF₃ | |
| 1-364 | CH₂CH₂SO₂CH₃ | CSN(Me)₂ | CF₃ | |
| 1-365 | CH₂CH₂SCH₂CH₃ | CSN(Me)₂ | CF₃ | |
| 1-366 | CH₂CH₂SOCH₂CH₃ | CSN(Me)₂ | CF₃ | |
| 1-367 | CH₂CH₂SO₂CH₂CH₃ | CSN(Me)₂ | CF₃ | |

TABLE 1-continued

| Compound No. | R³ | R⁴ | R⁵ | Physical property |
|---|---|---|---|---|
| 1-368 | CH₂CH₂SCF₃ | CSN(Me)₂ | CF₃ | |
| 1-369 | CH₂CH₂SOCF₃ | CSN(Me)₂ | CF₃ | |
| 1-370 | CH₂CH₂SO₂CF₃ | CSN(Me)₂ | CF₃ | |
| 1-371 | CH₂Ph | CSN(Me)₂ | CF₃ | |
| 1-372 | CH₂C≡CH | CSN(Me)₂ | CF₃ | |
| 1-373 | CH₂C≡CCH₃ | CSN(Me)₂ | CF₃ | |
| 1-374 | CH₂C≡N | CSN(Me)₂ | CF₃ | |
| 1-375 | CH₂CH=CH₂ | CSN(Me)₂ | CF₃ | |
| 1-376 | CH₂CH=CHCH₃ | CSN(Me)₂ | CF₃ | |
| 1-377 | CH₂CH=C(CH₃)₃ | CSN(Me)₂ | CF₃ | |
| 1-378 | CH₂OCH₃ | CSN(Me)₂ | CF₃ | |
| 1-379 | CH₂CH₂OCH₃ | CSN(Me)₂ | CF₃ | |
| 1-380 | CH₂OCH₂CH₃ | CSN(Me)₂ | CF₃ | |
| 1-381 | CH₂CH₂OCH₂CH₃ | CSN(Me)₂ | CF₃ | |
| 1-382 | H | CSNHEt | CF₃ | |
| 1-383 | Me | CSNHEt | CF₃ | |
| 1-384 | Et | CSNHEt | CF₃ | 99-100 |
| 1-385 | n-Pr | CSNHEt | CF₃ | |
| 1-386 | i-Pr | CSNHEt | CF₃ | |
| 1-387 | c-Pr | CSNHEt | CF₃ | |
| 1-388 | n-Bu | CSNHEt | CF₃ | |
| 1-389 | n-Pen | CSNHEt | CF₃ | |
| 1-390 | CH₂CF₃ | CSNHEt | CF₃ | |
| 1-391 | CH₂C₂F₅ | CSNHEt | CF₃ | |
| 1-392 | CH₂CHF₂ | CSNHEt | CF₃ | |
| 1-393 | CH₂CF₂CHF₂ | CSNHEt | CF₃ | |
| 1-394 | CH₂SCH₃ | CSNHEt | CF₃ | |
| 1-395 | CH₂SOCH₃ | CSNHEt | CF₃ | |
| 1-396 | CH₂SO₂CH₃ | CSNHEt | CF₃ | |
| 1-397 | CH₂SCH₂CH₃ | CSNHEt | CF₃ | |
| 1-398 | CH₂SOCH₂CH₃ | CSNHEt | CF₃ | |
| 1-399 | CH₂SO₂CH₂CH₃ | CSNHEt | CF₃ | |
| 1-400 | CH₂CH₂SCH₃ | CSNHEt | CF₃ | |
| 1-401 | CH₂CH₂SOCH₃ | CSNHEt | CF₃ | |
| 1-402 | CH₂CH₂SO₂CH₃ | CSNHEt | CF₃ | |
| 1-403 | CH₂CH₂SCH₂CH₃ | CSNHEt | CF₃ | |
| 1-404 | CH₂CH₂SOCH₂CH₃ | CSNHEt | CF₃ | |
| 1-405 | CH₂CH₂SO₂CH₂CH₃ | CSNHEt | CF₃ | |
| 1-406 | CH₂CH₂SCF₃ | CSNHEt | CF₃ | |
| 1-407 | CH₂CH₂SOCF₃ | CSNHEt | CF₃ | |
| 1-408 | CH₂CH₂SO₂CF₃ | CSNHEt | CF₃ | |
| 1-409 | CH₂Ph | CSNHEt | CF₃ | |
| 1-410 | CH₂C≡CH | CSNHEt | CF₃ | |
| 1-411 | CH₂C≡CCH₃ | CSNHEt | CF₃ | |
| 1-412 | CH₂C≡N | CSNHEt | CF₃ | |
| 1-413 | CH₂CH=CH₂ | CSNHEt | CF₃ | |
| 1-414 | CH₂CH=CHCH₃ | CSNHEt | CF₃ | |
| 1-415 | CH₂CH=C(CH₃)₃ | CSNHEt | CF₃ | |
| 1-416 | CH₂OCH₃ | CSNHEt | CF₃ | |
| 1-417 | CH₂CH₂OCH₃ | CSNHEt | CF₃ | |
| 1-418 | CH₂OCH₂CH₃ | CSNHEt | CF₃ | |
| 1-419 | CH₂CH₂OCH₂CH₃ | CSNHEt | CF₃ | |
| 1-420 | H | SO₂Me | CF₃ | 109-110 |
| 1-421 | Me | SO₂Me | CF₃ | |
| 1-422 | Et | SO₂Me | CF₃ | |
| 1-423 | n-Pr | SO₂Me | CF₃ | |
| 1-424 | i-Pr | SO₂Me | CF₃ | |
| 1-425 | c-Pr | SO₂Me | CF₃ | |
| 1-426 | n-Bu | SO₂Me | CF₃ | |
| 1-427 | n-Pen | SO₂Me | CF₃ | |
| 1-428 | CH₂CF₃ | SO₂Me | CF₃ | |
| 1-429 | CH₂C₂F₅ | SO₂Me | CF₃ | |
| 1-430 | CH₂CHF₂ | SO₂Me | CF₃ | |
| 1-431 | CH₂CF₂CHF₂ | SO₂Me | CF₃ | |
| 1-432 | CH₂SCH₃ | SO₂Me | CF₃ | |
| 1-433 | CH₂SOCH₃ | SO₂Me | CF₃ | |
| 1-434 | CH₂SO₂CH₃ | SO₂Me | CF₃ | |
| 1-435 | CH₂SCH₂CH₃ | SO₂Me | CF₃ | |
| 1-436 | CH₂SOCH₂CH₃ | SO₂Me | CF₃ | |
| 1-437 | CH₂SO₂CH₂CH₃ | SO₂Me | CF₃ | |
| 1-438 | CH₂CH₂SCH₃ | SO₂Me | CF₃ | |
| 1-439 | CH₂CH₂SOCH₃ | SO₂Me | CF₃ | |
| 1-440 | CH₂CH₂SO₂CH₃ | SO₂Me | CF₃ | |
| 1-441 | CH₂CH₂SCH₂CH₃ | SO₂Me | CF₃ | |
| 1-442 | CH₂CH₂SOCH₂CH₃ | SO₂Me | CF₃ | |
| 1-443 | CH₂CH₂SO₂CH₂CH₃ | SO₂Me | CF₃ | |
| 1-444 | CH₂CH₂SCF₃ | SO₂Me | CF₃ | |
| 1-445 | CH₂CH₂SOCF₃ | SO₂Me | CF₃ | |
| 1-446 | CH₂CH₂SO₂CF₃ | SO₂Me | CF₃ | |
| 1-447 | CH₂Ph | SO₂Me | CF₃ | |
| 1-448 | CH₂C≡CH | SO₂Me | CF₃ | |
| 1-449 | CH₂C≡CCH₃ | SO₂Me | CF₃ | |
| 1-450 | CH₂C≡N | SO₂Me | CF₃ | |
| 1-451 | CH₂CH=CH₂ | SO₂Me | CF₃ | |
| 1-452 | CH₂CH=CHCH₃ | SO₂Me | CF₃ | |
| 1-453 | CH₂CH=C(CH₃)₃ | SO₂Me | CF₃ | |
| 1-454 | CH₂OCH₃ | SO₂Me | CF₃ | |
| 1-455 | CH₂CH₂OCH₃ | SO₂Me | CF₃ | |
| 1-456 | CH₂OCH₂CH₃ | SO₂Me | CF₃ | |
| 1-457 | CH₂CH₂OCH₂CH₃ | SO₂Me | CF₃ | |
| 1-458 | n-Pr | CH₂OCH₃ | CF₃ | |
| 1-459 | CH₂CF₃ | CH₂OCH₃ | CF₃ | |
| 1-460 | CH₂C₂F₅ | CH₂OCH₃ | CF₃ | |
| 1-461 | CH₂CHF₂ | CH₂OCH₃ | CF₃ | |
| 1-462 | CH₂CF₂CHF₂ | CH₂OCH₃ | CF₃ | |

[Chem. 11]

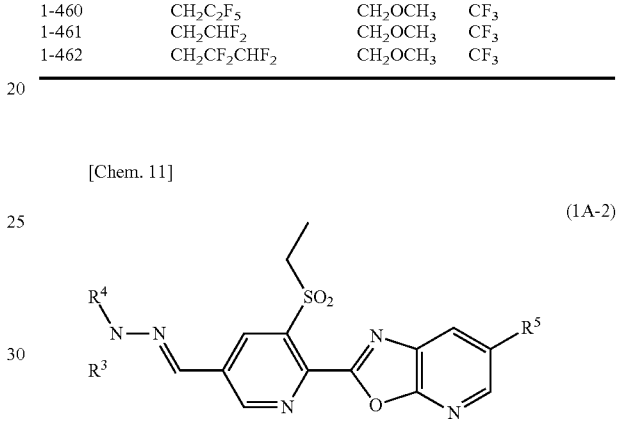

(1A-2)

TABLE 2

| Compound No. | R³ | R⁴ | R⁵ | Physical property |
|---|---|---|---|---|
| 2-1 | H | H | SCF₃ | 229-230 |
| 2-2 | Me | H | SCF₃ | |
| 2-3 | Et | H | SCF₃ | 191-192 |
| 2-4 | n-Pr | H | SCF₃ | |
| 2-5 | i-Pr | H | SCF₃ | |
| 2-6 | c-Pr | H | SCF₃ | |
| 2-7 | n-Bu | H | SCF₃ | |
| 2-8 | n-Pen | H | SCF₃ | |
| 2-9 | CH₂CF₃ | H | SCF₃ | 206-207 |
| 2-10 | CH₂C₂F₅ | H | SCF₃ | |
| 2-11 | CH₂CHF₂ | H | SCF₃ | |
| 2-12 | CH₂CF₂CHF₂ | H | SCF₃ | |
| 2-13 | CH₂SCH₃ | H | SCF₃ | |
| 2-14 | CH₂SOCH₃ | H | SCF₃ | |
| 2-15 | CH₂SO₂CH₃ | H | SCF₃ | |
| 2-16 | CH₂SCH₂CH₃ | H | SCF₃ | |
| 2-17 | CH₂SOCH₂CH₃ | H | SCF₃ | |
| 2-18 | CH₂SO₂CH₂CH₃ | H | SCF₃ | |
| 2-19 | CH₂CH₂SCH₃ | H | SCF₃ | |
| 2-20 | CH₂CH₂SOCH₃ | H | SCF₃ | |
| 2-21 | CH₂CH₂SO₂CH₃ | H | SCF₃ | |
| 2-22 | CH₂CH₂SCH₂CH₃ | H | SCF₃ | |
| 2-23 | CH₂CH₂SOCH₂CH₃ | H | SCF₃ | |
| 2-24 | CH₂CH₂SO₂CH₂CH₃ | H | SCF₃ | |
| 2-25 | CH₂CH₂SCF₃ | H | SCF₃ | |
| 2-26 | CH₂CH₂SOCF₃ | H | SCF₃ | |
| 2-27 | CH₂CH₂SO₂CF₃ | H | SCF₃ | |
| 2-28 | CH₂Ph | H | SCF₃ | |
| 2-29 | CH₂C≡CH | H | SCF₃ | |
| 2-30 | CH₂C≡CCH₃ | H | SCF₃ | |
| 2-31 | CH₂C≡N | H | SCF₃ | |
| 2-32 | CH₂CH=CH₂ | H | SCF₃ | |
| 2-33 | CH₂CH=CHCH₃ | H | SCF₃ | |
| 2-34 | CH₂CH=C(CH₃)₃ | H | SCF₃ | |

TABLE 2-continued

| Compound No. | R³ | R⁴ | R⁵ | Physical property |
|---|---|---|---|---|
| 2-35 | CH₂OCH₃ | H | SCF₃ | |
| 2-36 | CH₂CH₂OCH₃ | H | SCF₃ | |
| 2-37 | CH₂OCH₂CH₃ | H | SCF₃ | |
| 2-38 | CH₂CH₂OCH₂CH₃ | H | SCF₃ | |
| 2-39 | Ph | H | SCF₃ | |
| 2-40 | 4-SMePh | H | SCF₃ | 199-200 |
| 2-41 | 4-CF₃Ph | H | SCF₃ | 228-229 |
| 2-42 | 2-F,4-Cl—Ph | H | SCF₃ | 247-248 |
| 2-43 | Me | Me | SCF₃ | |
| 2-44 | Et | Me | SCF₃ | |
| 2-45 | n-Pr | Me | SCF₃ | |
| 2-46 | i-Pr | Me | SCF₃ | |
| 2-47 | c-Pr | Me | SCF₃ | |
| 2-48 | n-Bu | Me | SCF₃ | |
| 2-49 | n-Pen | Me | SCF₃ | |
| 2-50 | CH₂CF₃ | Me | SCF₃ | 194-195 |
| 2-51 | CH₂C₂F₅ | Me | SCF₃ | |
| 2-52 | CH₂CHF₂ | Me | SCF₃ | |
| 2-53 | CH₂CF₂CHF₂ | Me | SCF₃ | |
| 2-54 | CH₂SCH₃ | Me | SCF₃ | |
| 2-55 | CH₂SOCH₃ | Me | SCF₃ | |
| 2-56 | CH₂SO₂CH₃ | Me | SCF₃ | |
| 2-57 | CH₂SCH₂CH₃ | Me | SCF₃ | |
| 2-58 | CH₂SOCH₂CH₃ | Me | SCF₃ | |
| 2-59 | CH₂SO₂CH₂CH₃ | Me | SCF₃ | |
| 2-60 | CH₂CH₂SCH₃ | Me | SCF₃ | |
| 2-61 | CH₂CH₂SOCH₃ | Me | SCF₃ | |
| 2-62 | CH₂CH₂SO₂CH₃ | Me | SCF₃ | |
| 2-63 | CH₂CH₂SCH₂CH₃ | Me | SCF₃ | |
| 2-64 | CH₂CH₂SOCH₂CH₃ | Me | SCF₃ | |
| 2-65 | CH₂CH₂SO₂CH₂CH₃ | Me | SCF₃ | |
| 2-66 | CH₂CH₂SCF₃ | Me | SCF₃ | |
| 2-67 | CH₂CH₂SOCF₃ | Me | SCF₃ | |
| 2-68 | CH₂CH₂SO₂CF₃ | Me | SCF₃ | |
| 2-69 | CH₂Ph | Me | SCF₃ | |
| 2-70 | CH₂C≡CH | Me | SCF₃ | |
| 2-71 | CH₂C≡CCH₃ | Me | SCF₃ | |
| 2-72 | CH₂C≡N | Me | SCF₃ | |
| 2-73 | CH₂CH═CH₂ | Me | SCF₃ | |
| 2-74 | CH₂CH═CHCH₃ | Me | SCF₃ | |
| 2-75 | CH₂CH═C(CH₃)₃ | Me | SCF₃ | |
| 2-76 | CH₂OCH₃ | Me | SCF₃ | |
| 2-77 | CH₂CH₂OCH₃ | Me | SCF₃ | |
| 2-78 | CH₂OCH₂CH₃ | Me | SCF₃ | |
| 2-79 | CH₂CH₂OCH₂CH₃ | Me | SCF₃ | |
| 2-80 | Et | Et | SCF₃ | |
| 2-81 | n-Pr | Et | SCF₃ | |
| 2-82 | i-Pr | Et | SCF₃ | |
| 2-83 | c-Pr | Et | SCF₃ | |
| 2-84 | n-Bu | Et | SCF₃ | |
| 2-85 | n-Pen | Et | SCF₃ | |
| 2-86 | CH₂CF₃ | Et | SCF₃ | 142-143 |
| 2-87 | CH₂C₂F₅ | Et | SCF₃ | |
| 2-88 | CH₂CHF₂ | Et | SCF₃ | |
| 2-89 | CH₂CF₂CHF₂ | Et | SCF₃ | 137-138 |
| 2-90 | CH₂SCH₃ | Et | SCF₃ | |
| 2-91 | CH₂SOCH₃ | Et | SCF₃ | |
| 2-92 | CH₂SO₂CH₃ | Et | SCF₃ | |
| 2-93 | CH₂SCH₂CH₃ | Et | SCF₃ | |
| 2-94 | CH₂SOCH₂CH₃ | Et | SCF₃ | |
| 2-95 | CH₂SO₂CH₂CH₃ | Et | SCF₃ | |
| 2-96 | CH₂CH₂SCH₃ | Et | SCF₃ | |
| 2-97 | CH₂CH₂SOCH₃ | Et | SCF₃ | |
| 2-98 | CH₂CH₂SO₂CH₃ | Et | SCF₃ | |
| 2-99 | CH₂CH₂SCH₂CH₃ | Et | SCF₃ | |
| 2-100 | CH₂CH₂SOCH₂CH₃ | Et | SCF₃ | |
| 2-101 | CH₂CH₂SO₂CH₂CH₃ | Et | SCF₃ | |
| 2-102 | CH₂CH₂SCF₃ | Et | SCF₃ | |
| 2-103 | CH₂CH₂SOCF₃ | Et | SCF₃ | |
| 2-104 | CH₂CH₂SO₂CF₃ | Et | SCF₃ | |
| 2-105 | CH₂Ph | Et | SCF₃ | |
| 2-106 | CH₂C≡CH | Et | SCF₃ | |
| 2-107 | CH₂C≡CCH₃ | Et | SCF₃ | |
| 2-108 | CH₂C≡N | Et | SCF₃ | |
| 2-109 | CH₂CH═CH₂ | Et | SCF₃ | |
| 2-110 | CH₂CH═CHCH₃ | Et | SCF₃ | |
| 2-111 | CH₂CH═C(CH₃)₃ | Et | SCF₃ | |
| 2-112 | CH₂OCH₃ | Et | SCF₃ | |
| 2-113 | CH₂CH₂OCH₃ | Et | SCF₃ | |
| 2-114 | CH₂OCH₂CH₃ | Et | SCF₃ | |
| 2-115 | CH₂CH₂OCH₂CH₃ | Et | SCF₃ | |
| 2-116 | H | Ac | SCF₃ | 261-262 |
| 2-117 | Me | Ac | SCF₃ | |
| 2-118 | Et | Ac | SCF₃ | 191-192 |
| 2-119 | n-Pr | Ac | SCF₃ | |
| 2-120 | i-Pr | Ac | SCF₃ | |
| 2-121 | c-Pr | Ac | SCF₃ | |
| 2-122 | n-Bu | Ac | SCF₃ | |
| 2-123 | n-Pen | Ac | SCF₃ | |
| 2-124 | CH₂CF₃ | Ac | SCF₃ | 87-88 |
| 2-125 | CH₂C₂F₅ | Ac | SCF₃ | |
| 2-126 | CH₂CHF₂ | Ac | SCF₃ | |
| 2-127 | CH₂CF₂CHF₂ | Ac | SCF₃ | |
| 2-128 | CH₂SCH₃ | Ac | SCF₃ | |
| 2-129 | CH₂SOCH₃ | Ac | SCF₃ | |
| 2-130 | CH₂SO₂CH₃ | Ac | SCF₃ | |
| 2-131 | CH₂SCH₂CH₃ | Ac | SCF₃ | |
| 2-132 | CH₂SOCH₂CH₃ | Ac | SCF₃ | |
| 2-133 | CH₂SO₂CH₂CH₃ | Ac | SCF₃ | |
| 2-134 | CH₂CH₂SCH₃ | Ac | SCF₃ | |
| 2-135 | CH₂CH₂SOCH₃ | Ac | SCF₃ | |
| 2-136 | CH₂CH₂SO₂CH₃ | Ac | SCF₃ | |
| 2-137 | CH₂CH₂SCH₂CH₃ | Ac | SCF₃ | |
| 2-138 | CH₂CH₂SOCH₂CH₃ | Ac | SCF₃ | |
| 2-139 | CH₂CH₂SO₂CH₂CH₃ | Ac | SCF₃ | |
| 2-140 | CH₂CH₂SCF₃ | Ac | SCF₃ | |
| 2-141 | CH₂CH₂SOCF₃ | Ac | SCF₃ | |
| 2-142 | CH₂CH₂SO₂CF₃ | Ac | SCF₃ | |
| 2-143 | CH₂Ph | Ac | SCF₃ | |
| 2-144 | CH₂C≡CH | Ac | SCF₃ | |
| 2-145 | CH₂C≡CCH₃ | Ac | SCF₃ | |
| 2-146 | CH₂C≡N | Ac | SCF₃ | |
| 2-147 | CH₂CH═CH₂ | Ac | SCF₃ | |
| 2-148 | CH₂CH═CHCH₃ | Ac | SCF₃ | |
| 2-149 | CH₂CH═C(CH₃)₃ | Ac | SCF₃ | |
| 2-150 | CH₂OCH₃ | Ac | SCF₃ | |
| 2-151 | CH₂CH₂OCH₃ | Ac | SCF₃ | |
| 2-152 | CH₂OCH₂CH₃ | Ac | SCF₃ | |
| 2-153 | CH₂CH₂OCH₂CH₃ | Ac | SCF₃ | |
| 2-154 | H | CO₂Me | SCF₃ | 235-236 |
| 2-155 | Me | CO₂Me | SCF₃ | |
| 2-156 | Et | CO₂Me | SCF₃ | 157-158 |
| 2-157 | n-Pr | CO₂Me | SCF₃ | |
| 2-158 | i-Pr | CO₂Me | SCF₃ | |
| 2-159 | c-Pr | CO₂Me | SCF₃ | |
| 2-160 | n-Bu | CO₂Me | SCF₃ | |
| 2-161 | n-Pen | CO₂Me | SCF₃ | |
| 2-162 | CH₂CF₃ | CO₂Me | SCF₃ | 193-194 |
| 2-163 | CH₂C₂F₅ | CO₂Me | SCF₃ | |
| 2-164 | CH₂CHF₂ | CO₂Me | SCF₃ | 175-176 |
| 2-165 | CH₂CF₂CHF₂ | CO₂Me | SCF₃ | |
| 2-166 | CH₂SCH₃ | CO₂Me | SCF₃ | |
| 2-167 | CH₂SOCH₃ | CO₂Me | SCF₃ | |
| 2-168 | CH₂SO₂CH₃ | CO₂Me | SCF₃ | |
| 2-169 | CH₂SCH₂CH₃ | CO₂Me | SCF₃ | |
| 2-170 | CH₂SOCH₂CH₃ | CO₂Me | SCF₃ | |
| 2-171 | CH₂SO₂CH₂CH₃ | CO₂Me | SCF₃ | |
| 2-172 | CH₂CH₂SCH₃ | CO₂Me | SCF₃ | |
| 2-173 | CH₂CH₂SOCH₃ | CO₂Me | SCF₃ | |
| 2-174 | CH₂CH₂SO₂CH₃ | CO₂Me | SCF₃ | |
| 2-175 | CH₂CH₂SCH₂CH₃ | CO₂Me | SCF₃ | |
| 2-176 | CH₂CH₂SOCH₂CH₃ | CO₂Me | SCF₃ | |
| 2-177 | CH₂CH₂SO₂CH₂CH₃ | CO₂Me | SCF₃ | |
| 2-178 | CH₂CH₂SCF₃ | CO₂Me | SCF₃ | |
| 2-179 | CH₂CH₂SOCF₃ | CO₂Me | SCF₃ | |
| 2-180 | CH₂CH₂SO₂CF₃ | CO₂Me | SCF₃ | |
| 2-181 | CH₂Ph | CO₂Me | SCF₃ | |
| 2-182 | CH₂C≡CH | CO₂Me | SCF₃ | |
| 2-183 | CH₂C≡CCH₃ | CO₂Me | SCF₃ | |
| 2-184 | CH₂C≡N | CO₂Me | SCF₃ | |
| 2-185 | CH₂CH═CH₂ | CO₂Me | SCF₃ | |
| 2-186 | CH₂CH═CHCH₃ | CO₂Me | SCF₃ | |
| 2-187 | CH₂CH═C(CH₃)₃ | CO₂Me | SCF₃ | |
| 2-188 | CH₂OCH₃ | CO₂Me | SCF₃ | |

TABLE 2-continued

| Compound No. | R³ | R⁴ | R⁵ | Physical property |
|---|---|---|---|---|
| 2-189 | CH₂CH₂OCH₃ | CO₂Me | SCF₃ | |
| 2-190 | CH₂OCH₂CH₃ | CO₂Me | SCF₃ | |
| 2-191 | CH₂CH₂OCH₂CH₃ | CO₂Me | SCF₃ | |
| 2-192 | H | CO₂Et | SCF₃ | |
| 2-193 | Me | CO₂Et | SCF₃ | |
| 2-194 | Et | CO₂Et | SCF₃ | |
| 2-195 | n-Pr | CO₂Et | SCF₃ | |
| 2-196 | i-Pr | CO₂Et | SCF₃ | |
| 2-197 | c-Pr | CO₂Et | SCF₃ | |
| 2-198 | n-Bu | CO₂Et | SCF₃ | |
| 2-199 | n-Pen | CO₂Et | SCF₃ | |
| 2-200 | CH₂CF₃ | CO₂Et | SCF₃ | |
| 2-201 | CH₂C₂F₅ | CO₂Et | SCF₃ | |
| 2-202 | CH₂CHF₂ | CO₂Et | SCF₃ | |
| 2-203 | CH₂CF₂CHF₂ | CO₂Et | SCF₃ | |
| 2-204 | CH₂SCH₃ | CO₂Et | SCF₃ | |
| 2-205 | CH₂SOCH₃ | CO₂Et | SCF₃ | |
| 2-206 | CH₂SO₂CH₃ | CO₂Et | SCF₃ | |
| 2-207 | CH₂SCH₂CH₃ | CO₂Et | SCF₃ | |
| 2-208 | CH₂SOCH₂CH₃ | CO₂Et | SCF₃ | |
| 2-209 | CH₂SO₂CH₂CH₃ | CO₂Et | SCF₃ | |
| 2-210 | CH₂CH₂SCH₃ | CO₂Et | SCF₃ | |
| 2-211 | CH₂CH₂SOCH₃ | CO₂Et | SCF₃ | |
| 2-212 | CH₂CH₂SO₂CH₃ | CO₂Et | SCF₃ | |
| 2-213 | CH₂CH₂SCH₂CH₃ | CO₂Et | SCF₃ | |
| 2-214 | CH₂CH₂SOCH₂CH₃ | CO₂Et | SCF₃ | |
| 2-215 | CH₂CH₂SO₂CH₂CH₃ | CO₂Et | SCF₃ | |
| 2-216 | CH₂CH₂SCF₃ | CO₂Et | SCF₃ | |
| 2-217 | CH₂CH₂SOCF₃ | CO₂Et | SCF₃ | |
| 2-218 | CH₂CH₂SO₂CF₃ | CO₂Et | SCF₃ | |
| 2-219 | CH₂Ph | CO₂Et | SCF₃ | |
| 2-220 | CH₂C≡CH | CO₂Et | SCF₃ | |
| 2-221 | CH₂C≡CCH₃ | CO₂Et | SCF₃ | |
| 2-222 | CH₂C≡N | CO₂Et | SCF₃ | |
| 2-223 | CH₂CH═CH₂ | CO₂Et | SCF₃ | |
| 2-224 | CH₂CH═CHCH₃ | CO₂Et | SCF₃ | |
| 2-225 | CH₂CH═C(CH₃)₃ | CO₂Et | SCF₃ | |
| 2-226 | CH₂OCH₃ | CO₂Et | SCF₃ | |
| 2-227 | CH₂CH₂OCH₃ | CO₂Et | SCF₃ | |
| 2-228 | CH₂OCH₂CH₃ | CO₂Et | SCF₃ | |
| 2-229 | CH₂CH₂OCH₂CH₃ | CO₂Et | SCF₃ | |
| 2-230 | H | COCF₃ | SCF₃ | 198-199 |
| 2-231 | Me | COCF₃ | SCF₃ | |
| 2-232 | Et | COCF₃ | SCF₃ | |
| 2-233 | n-Pr | COCF₃ | SCF₃ | |
| 2-234 | i-Pr | COCF₃ | SCF₃ | |
| 2-235 | c-Pr | COCF₃ | SCF₃ | |
| 2-236 | n-Bu | COCF₃ | SCF₃ | |
| 2-237 | n-Pen | COCF₃ | SCF₃ | |
| 2-238 | CH₂CF₃ | COCF₃ | SCF₃ | |
| 2-239 | CH₂C₂F₅ | COCF₃ | SCF₃ | |
| 2-240 | CH₂CHF₂ | COCF₃ | SCF₃ | |
| 2-241 | CH₂CF₂CHF₂ | COCF₃ | SCF₃ | |
| 2-242 | CH₂SCH₃ | COCF₃ | SCF₃ | |
| 2-243 | CH₂SOCH₃ | COCF₃ | SCF₃ | |
| 2-244 | CH₂SO₂CH₃ | COCF₃ | SCF₃ | |
| 2-245 | CH₂SCH₂CH₃ | COCF₃ | SCF₃ | |
| 2-246 | CH₂SOCH₂CH₃ | COCF₃ | SCF₃ | |
| 2-247 | CH₂SO₂CH₂CH₃ | COCF₃ | SCF₃ | |
| 2-248 | CH₂CH₂SCH₃ | COCF₃ | SCF₃ | |
| 2-249 | CH₂CH₂SOCH₃ | COCF₃ | SCF₃ | |
| 2-250 | CH₂CH₂SO₂CH₃ | COCF₃ | SCF₃ | |
| 2-251 | CH₂CH₂SCH₂CH₃ | COCF₃ | SCF₃ | |
| 2-252 | CH₂CH₂SOCH₂CH₃ | COCF₃ | SCF₃ | |
| 2-253 | CH₂CH₂SO₂CH₂CH₃ | COCF₃ | SCF₃ | |
| 2-254 | CH₂CH₂SCF₃ | COCF₃ | SCF₃ | |
| 2-255 | CH₂CH₂SOCF₃ | COCF₃ | SCF₃ | |
| 2-256 | CH₂CH₂SO₂CF₃ | COCF₃ | SCF₃ | |
| 2-257 | CH₂Ph | COCF₃ | SCF₃ | |
| 2-258 | CH₂C≡CH | COCF₃ | SCF₃ | |
| 2-259 | CH₂C≡CCH₃ | COCF₃ | SCF₃ | |
| 2-260 | CH₂C≡N | COCF₃ | SCF₃ | |
| 2-261 | CH₂CH═CH₂ | COCF₃ | SCF₃ | |
| 2-262 | CH₂CH═CHCH₃ | COCF₃ | SCF₃ | |
| 2-263 | CH₂CH═C(CH₃)₃ | COCF₃ | SCF₃ | |
| 2-264 | CH₂OCH₃ | COCF₃ | SCF₃ | |
| 2-265 | CH₂CH₂OCH₃ | COCF₃ | SCF₃ | |
| 2-266 | CH₂OCH₂CH₃ | COCF₃ | SCF₃ | |
| 2-267 | CH₂CH₂OCH₂CH₃ | COCF₃ | SCF₃ | |
| 2-268 | H | CSOMe | SCF₃ | |
| 2-269 | Me | CSOMe | SCF₃ | |
| 2-270 | Et | CSOMe | SCF₃ | |
| 2-271 | n-Pr | CSOMe | SCF₃ | |
| 2-272 | i-Pr | CSOMe | SCF₃ | |
| 2-273 | c-Pr | CSOMe | SCF₃ | |
| 2-274 | n-Bu | CSOMe | SCF₃ | |
| 2-275 | n-Pen | CSOMe | SCF₃ | |
| 2-276 | CH₂CF₃ | CSOMe | SCF₃ | |
| 2-277 | CH₂C₂F₅ | CSOMe | SCF₃ | |
| 2-278 | CH₂CHF₂ | CSOMe | SCF₃ | |
| 2-279 | CH₂CF₂CHF₂ | CSOMe | SCF₃ | |
| 2-280 | CH₂SCH₃ | CSOMe | SCF₃ | |
| 2-281 | CH₂SOCH₃ | CSOMe | SCF₃ | |
| 2-282 | CH₂SO₂CH₃ | CSOMe | SCF₃ | |
| 2-283 | CH₂SCH₂CH₃ | CSOMe | SCF₃ | |
| 2-284 | CH₂SOCH₂CH₃ | CSOMe | SCF₃ | |
| 2-285 | CH₂SO₂CH₂CH₃ | CSOMe | SCF₃ | |
| 2-286 | CH₂CH₂SCH₃ | CSOMe | SCF₃ | |
| 2-287 | CH₂CH₂SOCH₃ | CSOMe | SCF₃ | |
| 2-288 | CH₂CH₂SO₂CH₃ | CSOMe | SCF₃ | |
| 2-289 | CH₂CH₂SCH₂CH₃ | CSOMe | SCF₃ | |
| 2-290 | CH₂CH₂SOCH₂CH₃ | CSOMe | SCF₃ | |
| 2-291 | CH₂CH₂SO₂CH₂CH₃ | CSOMe | SCF₃ | |
| 2-292 | CH₂CH₂SCF₃ | CSOMe | SCF₃ | |
| 2-293 | CH₂CH₂SOCF₃ | CSOMe | SCF₃ | |
| 2-294 | CH₂CH₂SO₂CF₃ | CSOMe | SCF₃ | |
| 2-295 | CH₂Ph | CSOMe | SCF₃ | |
| 2-296 | CH₂C≡CH | CSOMe | SCF₃ | |
| 2-297 | CH₂C≡CCH₃ | CSOMe | SCF₃ | |
| 2-298 | CH₂C≡N | CSOMe | SCF₃ | |
| 2-299 | CH₂CH═CH₂ | CSOMe | SCF₃ | |
| 2-300 | CH₂CH═CHCH₃ | CSOMe | SCF₃ | |
| 2-301 | CH₂CH═C(CH₃)₃ | CSOMe | SCF₃ | |
| 2-302 | CH₂OCH₃ | CSOMe | SCF₃ | |
| 2-303 | CH₂CH₂OCH₃ | CSOMe | SCF₃ | |
| 2-304 | CH₂OCH₂CH₃ | CSOMe | SCF₃ | |
| 2-305 | CH₂CH₂OCH₂CH₃ | CSOMe | SCF₃ | |
| 2-306 | H | CSOEt | SCF₃ | 233-234 |
| 2-307 | Me | CSOEt | SCF₃ | |
| 2-308 | Et | CSOEt | SCF₃ | 85-86 |
| 2-309 | n-Pr | CSOEt | SCF₃ | |
| 2-310 | i-Pr | CSOEt | SCF₃ | |
| 2-311 | c-Pr | CSOEt | SCF₃ | |
| 2-312 | n-Bu | CSOEt | SCF₃ | |
| 2-313 | n-Pen | CSOEt | SCF₃ | |
| 2-314 | CH₂CF₃ | CSOEt | SCF₃ | |
| 2-315 | CH₂C₂F₅ | CSOEt | SCF₃ | |
| 2-316 | CH₂CHF₂ | CSOEt | SCF₃ | |
| 2-317 | CH₂CF₂CHF₂ | CSOEt | SCF₃ | |
| 2-318 | CH₂SCH₃ | CSOEt | SCF₃ | |
| 2-319 | CH₂SOCH₃ | CSOEt | SCF₃ | |
| 2-320 | CH₂SO₂CH₃ | CSOEt | SCF₃ | |
| 2-321 | CH₂SCH₂CH₃ | CSOEt | SCF₃ | |
| 2-322 | CH₂SOCH₂CH₃ | CSOEt | SCF₃ | |
| 2-323 | CH₂SO₂CH₂CH₃ | CSOEt | SCF₃ | |
| 2-324 | CH₂CH₂SCH₃ | CSOEt | SCF₃ | |
| 2-325 | CH₂CH₂SOCH₃ | CSOEt | SCF₃ | |
| 2-326 | CH₂CH₂SO₂CH₃ | CSOEt | SCF₃ | |
| 2-327 | CH₂CH₂SCH₂CH₃ | CSOEt | SCF₃ | |
| 2-328 | CH₂CH₂SOCH₂CH₃ | CSOEt | SCF₃ | |
| 2-329 | CH₂CH₂SO₂CH₂CH₃ | CSOEt | SCF₃ | |
| 2-330 | CH₂CH₂SCF₃ | CSOEt | SCF₃ | |
| 2-331 | CH₂CH₂SOCF₃ | CSOEt | SCF₃ | |
| 2-332 | CH₂CH₂SO₂CF₃ | CSOEt | SCF₃ | |
| 2-333 | CH₂Ph | CSOEt | SCF₃ | |
| 2-334 | CH₂C≡CH | CSOEt | SCF₃ | |
| 2-335 | CH₂C≡CCH₃ | CSOEt | SCF₃ | |
| 2-336 | CH₂C≡N | CSOEt | SCF₃ | |
| 2-337 | CH₂CH═CH₂ | CSOEt | SCF₃ | |
| 2-338 | CH₂CH═CHCH₃ | CSOEt | SCF₃ | |
| 2-339 | CH₂CH═C(CH₃)₃ | CSOEt | SCF₃ | |
| 2-340 | CH₂OCH₃ | CSOEt | SCF₃ | |
| 2-341 | CH₂CH₂OCH₃ | CSOEt | SCF₃ | |
| 2-342 | CH₂OCH₂CH₃ | CSOEt | SCF₃ | |

TABLE 2-continued

| Compound No. | R³ | R⁴ | R⁵ | Physical property |
|---|---|---|---|---|
| 2-343 | CH₂CH₂OCH₂CH₃ | CSOEt | SCF₃ | |
| 2-344 | H | CSN(Me)₂ | SCF₃ | |
| 2-345 | Me | CSN(Me)₂ | SCF₃ | |
| 2-346 | Et | CSN(Me)₂ | SCF₃ | 141-142 |
| 2-347 | n-Pr | CSN(Me)₂ | SCF₃ | |
| 2-348 | i-Pr | CSN(Me)₂ | SCF₃ | |
| 2-349 | c-Pr | CSN(Me)₂ | SCF₃ | |
| 2-350 | n-Bu | CSN(Me)₂ | SCF₃ | |
| 2-351 | n-Pen | CSN(Me)₂ | SCF₃ | |
| 2-352 | CH₂CF₃ | CSN(Me)₂ | SCF₃ | |
| 2-353 | CH₂C₂F₅ | CSN(Me)₂ | SCF₃ | |
| 2-354 | CH₂CHF₂ | CSN(Me)₂ | SCF₃ | |
| 2-355 | CH₂CF₂CHF₂ | CSN(Me)₂ | SCF₃ | |
| 2-356 | CH₂SCH₃ | CSN(Me)₂ | SCF₃ | |
| 2-357 | CH₂SOCH₃ | CSN(Me)₂ | SCF₃ | |
| 2-358 | CH₂SO₂CH₃ | CSN(Me)₂ | SCF₃ | |
| 2-359 | CH₂SCH₂CH₃ | CSN(Me)₂ | SCF₃ | |
| 2-360 | CH₂SOCH₂CH₃ | CSN(Me)₂ | SCF₃ | |
| 2-361 | CH₂SO₂CH₂CH₃ | CSN(Me)₂ | SCF₃ | |
| 2-362 | CH₂CH₂SCH₃ | CSN(Me)₂ | SCF₃ | |
| 2-363 | CH₂CH₂SOCH₃ | CSN(Me)₂ | SCF₃ | |
| 2-364 | CH₂CH₂SO₂CH₃ | CSN(Me)₂ | SCF₃ | |
| 2-365 | CH₂CH₂SCH₂CH₃ | CSN(Me)₂ | SCF₃ | |
| 2-366 | CH₂CH₂SOCH₂CH₃ | CSN(Me)₂ | SCF₃ | |
| 2-367 | CH₂CH₂SO₂CH₂CH₃ | CSN(Me)₂ | SCF₃ | |
| 2-368 | CH₂CH₂SCF₃ | CSN(Me)₂ | SCF₃ | |
| 2-369 | CH₂CH₂SOCF₃ | CSN(Me)₂ | SCF₃ | |
| 2-370 | CH₂CH₂SO₂CF₃ | CSN(Me)₂ | SCF₃ | |
| 2-371 | CH₂Ph | CSN(Me)₂ | SCF₃ | |
| 2-372 | CH₂C≡CH | CSN(Me)₂ | SCF₃ | |
| 2-373 | CH₂C≡CCH₃ | CSN(Me)₂ | SCF₃ | |
| 2-374 | CH₂C≡N | CSN(Me)₂ | SCF₃ | |
| 2-375 | CH₂CH=CH₂ | CSN(Me)₂ | SCF₃ | |
| 2-376 | CH₂CH=CHCH₃ | CSN(Me)₂ | SCF₃ | |
| 2-377 | CH₂CH=C(CH₃)₃ | CSN(Me)₂ | SCF₃ | |
| 2-378 | CH₂OCH₃ | CSN(Me)₂ | SCF₃ | |
| 2-379 | CH₂CH₂OCH₃ | CSN(Me)₂ | SCF₃ | |
| 2-380 | CH₂OCH₂CH₃ | CSN(Me)₂ | SCF₃ | |
| 2-381 | CH₂CH₂OCH₂CH₃ | CSN(Me)₂ | SCF₃ | |
| 2-382 | H | CSNHEt | SCF₃ | |
| 2-383 | Me | CSNHEt | SCF₃ | |
| 2-384 | Et | CSNHEt | SCF₃ | 191-192 |
| 2-385 | n-Pr | CSNHEt | SCF₃ | |
| 2-386 | i-Pr | CSNHEt | SCF₃ | |
| 2-387 | c-Pr | CSNHEt | SCF₃ | |
| 2-388 | n-Bu | CSNHEt | SCF₃ | |
| 2-389 | n-Pen | CSNHEt | SCF₃ | |
| 2-390 | CH₂CF₃ | CSNHEt | SCF₃ | |
| 2-391 | CH₂C₂F₅ | CSNHEt | SCF₃ | |
| 2-392 | CH₂CHF₂ | CSNHEt | SCF₃ | |
| 2-393 | CH₂CF₂CHF₂ | CSNHEt | SCF₃ | |
| 2-394 | CH₂SCH₃ | CSNHEt | SCF₃ | |
| 2-395 | CH₂SOCH₃ | CSNHEt | SCF₃ | |
| 2-396 | CH₂SO₂CH₃ | CSNHEt | SCF₃ | |
| 2-397 | CH₂SCH₂CH₃ | CSNHEt | SCF₃ | |
| 2-398 | CH₂SOCH₂CH₃ | CSNHEt | SCF₃ | |
| 2-399 | CH₂SO₂CH₂CH₃ | CSNHEt | SCF₃ | |
| 2-400 | CH₂CH₂SCH₃ | CSNHEt | SCF₃ | |
| 2-401 | CH₂CH₂SOCH₃ | CSNHEt | SCF₃ | |
| 2-402 | CH₂CH₂SO₂CH₃ | CSNHEt | SCF₃ | |
| 2-403 | CH₂CH₂SCH₂CH₃ | CSNHEt | SCF₃ | |
| 2-404 | CH₂CH₂SOCH₂CH₃ | CSNHEt | SCF₃ | |
| 2-405 | CH₂CH₂SO₂CH₂CH₃ | CSNHEt | SCF₃ | |
| 2-406 | CH₂CH₂SCF₃ | CSNHEt | SCF₃ | |
| 2-407 | CH₂CH₂SOCF₃ | CSNHEt | SCF₃ | |
| 2-408 | CH₂CH₂SO₂CF₃ | CSNHEt | SCF₃ | |
| 2-409 | CH₂Ph | CSNHEt | SCF₃ | |
| 2-410 | CH₂C≡CH | CSNHEt | SCF₃ | |
| 2-411 | CH₂C≡CCH₃ | CSNHEt | SCF₃ | |
| 2-412 | CH₂C≡N | CSNHEt | SCF₃ | |
| 2-413 | CH₂CH=CH₂ | CSNHEt | SCF₃ | |
| 2-414 | CH₂CH=CHCH₃ | CSNHEt | SCF₃ | |
| 2-415 | CH₂CH=C(CH₃)₃ | CSNHEt | SCF₃ | |
| 2-416 | CH₂OCH₃ | CSNHEt | SCF₃ | |
| 2-417 | CH₂CH₂OCH₃ | CSNHEt | SCF₃ | |
| 2-418 | CH₂OCH₂CH₃ | CSNHEt | SCF₃ | |
| 2-419 | CH₂CH₂OCH₂CH₃ | CSNHEt | SCF₃ | |
| 2-420 | H | SO₂Me | SCF₃ | |
| 2-421 | Me | SO₂Me | SCF₃ | 215-216 |
| 2-422 | Et | SO₂Me | SCF₃ | |
| 2-423 | n-Pr | SO₂Me | SCF₃ | |
| 2-424 | i-Pr | SO₂Me | SCF₃ | |
| 2-425 | c-Pr | SO₂Me | SCF₃ | |
| 2-426 | n-Bu | SO₂Me | SCF₃ | |
| 2-427 | n-Pen | SO₂Me | SCF₃ | |
| 2-428 | CH₂CF₃ | SO₂Me | SCF₃ | 115-116 |
| 2-429 | CH₂C₂F₅ | SO₂Me | SCF₃ | |
| 2-430 | CH₂CHF₂ | SO₂Me | SCF₃ | 231-232 |
| 2-431 | CH₂CF₂CHF₂ | SO₂Me | SCF₃ | |
| 2-432 | CH₂SCH₃ | SO₂Me | SCF₃ | |
| 2-433 | CH₂SOCH₃ | SO₂Me | SCF₃ | |
| 2-434 | CH₂SO₂CH₃ | SO₂Me | SCF₃ | |
| 2-435 | CH₂SCH₂CH₃ | SO₂Me | SCF₃ | |
| 2-436 | CH₂SOCH₂CH₃ | SO₂Me | SCF₃ | |
| 2-437 | CH₂SO₂CH₂CH₃ | SO₂Me | SCF₃ | |
| 2-438 | CH₂CH₂SCH₃ | SO₂Me | SCF₃ | |
| 2-439 | CH₂CH₂SOCH₃ | SO₂Me | SCF₃ | |
| 2-440 | CH₂CH₂SO₂CH₃ | SO₂Me | SCF₃ | |
| 2-441 | CH₂CH₂SCH₂CH₃ | SO₂Me | SCF₃ | |
| 2-442 | CH₂CH₂SOCH₂CH₃ | SO₂Me | SCF₃ | |
| 2-443 | CH₂CH₂SO₂CH₂CH₃ | SO₂Me | SCF₃ | |
| 2-444 | CH₂CH₂SCF₃ | SO₂Me | SCF₃ | |
| 2-445 | CH₂CH₂SOCF₃ | SO₂Me | SCF₃ | |
| 2-446 | CH₂CH₂SO₂CF₃ | SO₂Me | SCF₃ | |
| 2-447 | CH₂Ph | SO₂Me | SCF₃ | |
| 2-448 | CH₂C≡CH | SO₂Me | SCF₃ | |
| 2-449 | CH₂C≡CCH₃ | SO₂Me | SCF₃ | |
| 2-450 | CH₂C≡N | SO₂Me | SCF₃ | |
| 2-451 | CH₂CH=CH₂ | SO₂Me | SCF₃ | |
| 2-452 | CH₂CH=CHCH₃ | SO₂Me | SCF₃ | |
| 2-453 | CH₂CH=C(CH₃)₃ | SO₂Me | SCF₃ | |
| 2-454 | CH₂OCH₃ | SO₂Me | SCF₃ | |
| 2-455 | CH₂CH₂OCH₃ | SO₂Me | SCF₃ | |
| 2-456 | CH₂OCH₂CH₃ | SO₂Me | SCF₃ | |
| 2-457 | CH₂CH₂OCH₂CH₃ | SO₂Me | SCF₃ | |
| 2-458 | H | H | SO₂CF₃ | |
| 2-459 | Me | H | SO₂CF₃ | |
| 2-460 | Et | H | SO₂CF₃ | |
| 2-461 | n-Pr | H | SO₂CF₃ | |
| 2-462 | i-Pr | H | SO₂CF₃ | |
| 2-463 | c-Pr | H | SO₂CF₃ | |
| 2-464 | n-Bu | H | SO₂CF₃ | |
| 2-465 | n-Pen | H | SO₂CF₃ | |
| 2-466 | CH₂CF₃ | H | SO₂CF₃ | |
| 2-467 | CH₂C₂F₅ | H | SO₂CF₃ | |
| 2-468 | CH₂CHF₂ | H | SO₂CF₃ | |
| 2-469 | CH₂CF₂CHF₂ | H | SO₂CF₃ | |
| 2-470 | CH₂SCH₃ | H | SO₂CF₃ | |
| 2-471 | CH₂SOCH₃ | H | SO₂CF₃ | |
| 2-472 | CH₂SO₂CH₃ | H | SO₂CF₃ | |
| 2-473 | CH₂SCH₂CH₃ | H | SO₂CF₃ | |
| 2-474 | CH₂SOCH₂CH₃ | H | SO₂CF₃ | |
| 2-475 | CH₂SO₂CH₂CH₃ | H | SO₂CF₃ | |
| 2-476 | CH₂CH₂SCH₃ | H | SO₂CF₃ | |
| 2-477 | CH₂CH₂SOCH₃ | H | SO₂CF₃ | |
| 2-478 | CH₂CH₂SO₂CH₃ | H | SO₂CF₃ | |
| 2-479 | CH₂CH₂SCH₂CH₃ | H | SO₂CF₃ | |
| 2-480 | CH₂CH₂SOCH₂CH₃ | H | SO₂CF₃ | |
| 2-481 | CH₂CH₂SO₂CH₂CH₃ | H | SO₂CF₃ | |
| 2-482 | CH₂CH₂SCF₃ | H | SO₂CF₃ | |
| 2-483 | CH₂CH₂SOCF₃ | H | SO₂CF₃ | |
| 2-484 | CH₂CH₂SO₂CF₃ | H | SO₂CF₃ | |
| 2-485 | CH₂Ph | H | SO₂CF₃ | |
| 2-486 | CH₂C≡CH | H | SO₂CF₃ | |
| 2-487 | CH₂C≡CCH₃ | H | SO₂CF₃ | |
| 2-488 | CH₂C≡N | H | SO₂CF₃ | |
| 2-489 | CH₂CH=CH₂ | H | SO₂CF₃ | |
| 2-490 | CH₂CH=CHCH₃ | H | SO₂CF₃ | |
| 2-491 | CH₂CH=C(CH₃)₃ | H | SO₂CF₃ | |
| 2-492 | CH₂OCH₃ | H | SO₂CF₃ | |
| 2-493 | CH₂CH₂OCH₃ | H | SO₂CF₃ | |
| 2-494 | CH₂OCH₂CH₃ | H | SO₂CF₃ | |
| 2-495 | CH₂CH₂OCH₂CH₃ | H | SO₂CF₃ | |
| 2-496 | Ph | H | SO₂CF₃ | |

TABLE 2-continued

| Compound No. | R³ | R⁴ | R⁵ | Physical property |
|---|---|---|---|---|
| 2-497 | 4-SMePh | H | SO₂CF₃ | |
| 2-498 | 4-CF₃Ph | H | SO₂CF₃ | |
| 2-499 | 2-F,4-Cl—Ph | H | SO₂CF₃ | |
| 2-500 | Me | Me | SO₂CF₃ | |
| 2-501 | Et | Me | SO₂CF₃ | |
| 2-502 | n-Pr | Me | SO₂CF₃ | |
| 2-503 | i-Pr | Me | SO₂CF₃ | |
| 2-504 | c-Pr | Me | SO₂CF₃ | |
| 2-505 | n-Bu | Me | SO₂CF₃ | |
| 2-506 | n-Pen | Me | SO₂CF₃ | |
| 2-507 | CH₂CF₃ | Me | SO₂CF₃ | |
| 2-508 | CH₂C₂F₅ | Me | SO₂CF₃ | |
| 2-509 | CH₂CHF₂ | Me | SO₂CF₃ | |
| 2-510 | CH₂CF₂CHF₂ | Me | SO₂CF₃ | |
| 2-511 | CH₂SCH₃ | Me | SO₂CF₃ | |
| 2-512 | CH₂SOCH₃ | Me | SO₂CF₃ | |
| 2-513 | CH₂SO₂CH₃ | Me | SO₂CF₃ | |
| 2-514 | CH₂SCH₂CH₃ | Me | SO₂CF₃ | |
| 2-515 | CH₂SOCH₂CH₃ | Me | SO₂CF₃ | |
| 2-516 | CH₂SO₂CH₂CH₃ | Me | SO₂CF₃ | |
| 2-517 | CH₂CH₂SCH₃ | Me | SO₂CF₃ | |
| 2-518 | CH₂CH₂SOCH₃ | Me | SO₂CF₃ | |
| 2-519 | CH₂CH₂SO₂CH₃ | Me | SO₂CF₃ | |
| 2-520 | CH₂CH₂SCH₂CH₃ | Me | SO₂CF₃ | |
| 2-521 | CH₂CH₂SOCH₂CH₃ | Me | SO₂CF₃ | |
| 2-522 | CH₂CH₂SO₂CH₂CH₃ | Me | SO₂CF₃ | |
| 2-523 | CH₂CH₂SCF₃ | Me | SO₂CF₃ | |
| 2-524 | CH₂CH₂SOCF₃ | Me | SO₂CF₃ | |
| 2-525 | CH₂CH₂SO₂CF₃ | Me | SO₂CF₃ | |
| 2-526 | CH₂Ph | Me | SO₂CF₃ | |
| 2-527 | CH₂C≡CH | Me | SO₂CF₃ | |
| 2-528 | CH₂C≡CCH₃ | Me | SO₂CF₃ | |
| 2-529 | CH₂C≡N | Me | SO₂CF₃ | |
| 2-530 | CH₂CH═CH₂ | Me | SO₂CF₃ | |
| 2-531 | CH₂CH═CHCH₃ | Me | SO₂CF₃ | |
| 2-532 | CH₂CH═C(CH₃)₃ | Me | SO₂CF₃ | |
| 2-533 | CH₂OCH₃ | Me | SO₂CF₃ | |
| 2-534 | CH₂CH₂OCH₃ | Me | SO₂CF₃ | |
| 2-535 | CH₂OCH₂CH₃ | Me | SO₂CF₃ | |
| 2-536 | CH₂CH₂OCH₂CH₃ | Me | SO₂CF₃ | |
| 2-537 | Et | Et | SO₂CF₃ | |
| 2-538 | n-Pr | Et | SO₂CF₃ | |
| 2-539 | i-Pr | Et | SO₂CF₃ | |
| 2-540 | c-Pr | Et | SO₂CF₃ | |
| 2-541 | n-Bu | Et | SO₂CF₃ | |
| 2-542 | n-Pen | Et | SO₂CF₃ | |
| 2-543 | CH₂CF₃ | Et | SO₂CF₃ | |
| 2-544 | CH₂C₂F₅ | Et | SO₂CF₃ | |
| 2-545 | CH₂CHF₂ | Et | SO₂CF₃ | |
| 2-546 | CH₂CF₂CHF₂ | Et | SO₂CF₃ | |
| 2-547 | CH₂SCH₃ | Et | SO₂CF₃ | |
| 2-548 | CH₂SOCH₃ | Et | SO₂CF₃ | |
| 2-549 | CH₂SO₂CH₃ | Et | SO₂CF₃ | |
| 2-550 | CH₂SCH₂CH₃ | Et | SO₂CF₃ | |
| 2-551 | CH₂SOCH₂CH₃ | Et | SO₂CF₃ | |
| 2-552 | CH₂SO₂CH₂CH₃ | Et | SO₂CF₃ | |
| 2-553 | CH₂CH₂SCH₃ | Et | SO₂CF₃ | |
| 2-554 | CH₂CH₂SOCH₃ | Et | SO₂CF₃ | |
| 2-555 | CH₂CH₂SO₂CH₃ | Et | SO₂CF₃ | |
| 2-556 | CH₂CH₂SCH₂CH₃ | Et | SO₂CF₃ | |
| 2-557 | CH₂CH₂SOCH₂CH₃ | Et | SO₂CF₃ | |
| 2-558 | CH₂CH₂SO₂CH₂CH₃ | Et | SO₂CF₃ | |
| 2-559 | CH₂CH₂SCF₃ | Et | SO₂CF₃ | |
| 2-560 | CH₂CH₂SOCF₃ | Et | SO₂CF₃ | |
| 2-561 | CH₂CH₂SO₂CF₃ | Et | SO₂CF₃ | |
| 2-562 | CH₂Ph | Et | SO₂CF₃ | |
| 2-563 | CH₂C≡CH | Et | SO₂CF₃ | |
| 2-564 | CH₂C≡CCH₃ | Et | SO₂CF₃ | |
| 2-565 | CH₂C≡N | Et | SO₂CF₃ | |
| 2-566 | CH₂CH═CH₂ | Et | SO₂CF₃ | |
| 2-567 | CH₂CH═CHCH₃ | Et | SO₂CF₃ | |
| 2-568 | CH₂CH═C(CH₃)₃ | Et | SO₂CF₃ | |
| 2-569 | CH₂OCH₃ | Et | SO₂CF₃ | |
| 2-570 | CH₂CH₂OCH₃ | Et | SO₂CF₃ | |
| 2-571 | CH₂OCH₂CH₃ | Et | SO₂CF₃ | |
| 2-572 | CH₂CH₂OCH₂CH₃ | Et | SO₂CF₃ | |
| 2-573 | H | Ac | SO₂CF₃ | |
| 2-574 | Me | Ac | SO₂CF₃ | |
| 2-575 | Et | Ac | SO₂CF₃ | |
| 2-576 | n-Pr | Ac | SO₂CF₃ | |
| 2-577 | i-Pr | Ac | SO₂CF₃ | |
| 2-578 | c-Pr | Ac | SO₂CF₃ | |
| 2-579 | n-Bu | Ac | SO₂CF₃ | |
| 2-580 | n-Pen | Ac | SO₂CF₃ | |
| 2-581 | CH₂CF₃ | Ac | SO₂CF₃ | |
| 2-582 | CH₂C₂F₅ | Ac | SO₂CF₃ | |
| 2-583 | CH₂CHF₂ | Ac | SO₂CF₃ | |
| 2-584 | CH₂CF₂CHF₂ | Ac | SO₂CF₃ | |
| 2-585 | CH₂SCH₃ | Ac | SO₂CF₃ | |
| 2-586 | CH₂SOCH₃ | Ac | SO₂CF₃ | |
| 2-587 | CH₂SO₂CH₃ | Ac | SO₂CF₃ | |
| 2-588 | CH₂SCH₂CH₃ | Ac | SO₂CF₃ | |
| 2-589 | CH₂SOCH₂CH₃ | Ac | SO₂CF₃ | |
| 2-590 | CH₂SO₂CH₂CH₃ | Ac | SO₂CF₃ | |
| 2-591 | CH₂CH₂SCH₃ | Ac | SO₂CF₃ | |
| 2-592 | CH₂CH₂SOCH₃ | Ac | SO₂CF₃ | |
| 2-593 | CH₂CH₂SO₂CH₃ | Ac | SO₂CF₃ | |
| 2-594 | CH₂CH₂SCH₂CH₃ | Ac | SO₂CF₃ | |
| 2-595 | CH₂CH₂SOCH₂CH₃ | Ac | SO₂CF₃ | |
| 2-596 | CH₂CH₂SO₂CH₂CH₃ | Ac | SO₂CF₃ | |
| 2-597 | CH₂CH₂SCF₃ | Ac | SO₂CF₃ | |
| 2-598 | CH₂CH₂SOCF₃ | Ac | SO₂CF₃ | |
| 2-599 | CH₂CH₂SO₂CF₃ | Ac | SO₂CF₃ | |
| 2-600 | CH₂Ph | Ac | SO₂CF₃ | |
| 2-601 | CH₂C≡CH | Ac | SO₂CF₃ | |
| 2-602 | CH₂C≡CCH₃ | Ac | SO₂CF₃ | |
| 2-603 | CH₂C≡N | Ac | SO₂CF₃ | |
| 2-604 | CH₂CH═CH₂ | Ac | SO₂CF₃ | |
| 2-605 | CH₂CH═CHCH₃ | Ac | SO₂CF₃ | |
| 2-606 | CH₂CH═C(CH₃)₃ | Ac | SO₂CF₃ | |
| 2-607 | CH₂OCH₃ | Ac | SO₂CF₃ | |
| 2-608 | CH₂CH₂OCH₃ | Ac | SO₂CF₃ | |
| 2-609 | CH₂OCH₂CH₃ | Ac | SO₂CF₃ | |
| 2-610 | CH₂CH₂OCH₂CH₃ | Ac | SO₂CF₃ | |
| 2-611 | H | CO₂Me | SO₂CF₃ | |
| 2-612 | Me | CO₂Me | SO₂CF₃ | |
| 2-613 | Et | CO₂Me | SO₂CF₃ | |
| 2-614 | n-Pr | CO₂Me | SO₂CF₃ | |
| 2-615 | i-Pr | CO₂Me | SO₂CF₃ | |
| 2-616 | c-Pr | CO₂Me | SO₂CF₃ | |
| 2-617 | n-Bu | CO₂Me | SO₂CF₃ | |
| 2-618 | n-Pen | CO₂Me | SO₂CF₃ | |
| 2-619 | CH₂CF₃ | CO₂Me | SO₂CF₃ | |
| 2-620 | CH₂C₂F₅ | CO₂Me | SO₂CF₃ | |
| 2-621 | CH₂CHF₂ | CO₂Me | SO₂CF₃ | |
| 2-622 | CH₂CF₂CHF₂ | CO₂Me | SO₂CF₃ | |
| 2-623 | CH₂SCH₃ | CO₂Me | SO₂CF₃ | |
| 2-624 | CH₂SOCH₃ | CO₂Me | SO₂CF₃ | |
| 2-625 | CH₂SO₂CH₃ | CO₂Me | SO₂CF₃ | |
| 2-626 | CH₂SCH₂CH₃ | CO₂Me | SO₂CF₃ | |
| 2-627 | CH₂SOCH₂CH₃ | CO₂Me | SO₂CF₃ | |
| 2-628 | CH₂SO₂CH₂CH₃ | CO₂Me | SO₂CF₃ | |
| 2-629 | CH₂CH₂SCH₃ | CO₂Me | SO₂CF₃ | |
| 2-630 | CH₂CH₂SOCH₃ | CO₂Me | SO₂CF₃ | |
| 2-631 | CH₂CH₂SO₂CH₃ | CO₂Me | SO₂CF₃ | |
| 2-632 | CH₂CH₂SCH₂CH₃ | CO₂Me | SO₂CF₃ | |
| 2-633 | CH₂CH₂SOCH₂CH₃ | CO₂Me | SO₂CF₃ | |
| 2-634 | CH₂CH₂SO₂CH₂CH₃ | CO₂Me | SO₂CF₃ | |
| 2-635 | CH₂CH₂SCF₃ | CO₂Me | SO₂CF₃ | |
| 2-636 | CH₂CH₂SOCF₃ | CO₂Me | SO₂CF₃ | |
| 2-637 | CH₂CH₂SO₂CF₃ | CO₂Me | SO₂CF₃ | |
| 2-638 | CH₂Ph | CO₂Me | SO₂CF₃ | |
| 2-639 | CH₂C≡CH | CO₂Me | SO₂CF₃ | |
| 2-640 | CH₂C≡CCH₃ | CO₂Me | SO₂CF₃ | |
| 2-641 | CH₂C≡N | CO₂Me | SO₂CF₃ | |
| 2-642 | CH₂CH═CH₂ | CO₂Me | SO₂CF₃ | |
| 2-643 | CH₂CH═CHCH₃ | CO₂Me | SO₂CF₃ | |
| 2-644 | CH₂CH═C(CH₃)₃ | CO₂Me | SO₂CF₃ | |
| 2-645 | CH₂OCH₃ | CO₂Me | SO₂CF₃ | |
| 2-646 | CH₂CH₂OCH₃ | CO₂Me | SO₂CF₃ | |
| 2-647 | CH₂OCH₂CH₃ | CO₂Me | SO₂CF₃ | |
| 2-648 | CH₂CH₂OCH₂CH₃ | CO₂Me | SO₂CF₃ | |
| 2-649 | H | CO₂Et | SO₂CF₃ | |
| 2-650 | Me | CO₂Et | SO₂CF₃ | |

TABLE 2-continued

| Compound No. | R³ | R⁴ | R⁵ | Physical property |
|---|---|---|---|---|
| 2-651 | Et | CO₂Et | SO₂CF₃ | |
| 2-652 | n-Pr | CO₂Et | SO₂CF₃ | |
| 2-653 | i-Pr | CO₂Et | SO₂CF₃ | |
| 2-654 | c-Pr | CO₂Et | SO₂CF₃ | |
| 2-655 | n-Bu | CO₂Et | SO₂CF₃ | |
| 2-656 | n-Pen | CO₂Et | SO₂CF₃ | |
| 2-657 | CH₂CF₃ | CO₂Et | SO₂CF₃ | |
| 2-658 | CH₂C₂F₅ | CO₂Et | SO₂CF₃ | |
| 2-659 | CH₂CHF₂ | CO₂Et | SO₂CF₃ | |
| 2-660 | CH₂CF₂CHF₂ | CO₂Et | SO₂CF₃ | |
| 2-661 | CH₂SCH₃ | CO₂Et | SO₂CF₃ | |
| 2-662 | CH₂SOCH₃ | CO₂Et | SO₂CF₃ | |
| 2-663 | CH₂SO₂CH₃ | CO₂Et | SO₂CF₃ | |
| 2-664 | CH₂SCH₂CH₃ | CO₂Et | SO₂CF₃ | |
| 2-665 | CH₂SOCH₂CH₃ | CO₂Et | SO₂CF₃ | |
| 2-666 | CH₂SO₂CH₂CH₃ | CO₂Et | SO₂CF₃ | |
| 2-667 | CH₂CH₂SCH₃ | CO₂Et | SO₂CF₃ | |
| 2-668 | CH₂CH₂SOCH₃ | CO₂Et | SO₂CF₃ | |
| 2-669 | CH₂CH₂SO₂CH₃ | CO₂Et | SO₂CF₃ | |
| 2-670 | CH₂CH₂SCH₂CH₃ | CO₂Et | SO₂CF₃ | |
| 2-671 | CH₂CH₂SOCH₂CH₃ | CO₂Et | SO₂CF₃ | |
| 2-672 | CH₂CH₂SO₂CH₂CH₃ | CO₂Et | SO₂CF₃ | |
| 2-673 | CH₂CH₂SCF₃ | CO₂Et | SO₂CF₃ | |
| 2-674 | CH₂CH₂SOCF₃ | CO₂Et | SO₂CF₃ | |
| 2-675 | CH₂CH₂SO₂CF₃ | CO₂Et | SO₂CF₃ | |
| 2-676 | CH₂Ph | CO₂Et | SO₂CF₃ | |
| 2-677 | CH₂C≡CH | CO₂Et | SO₂CF₃ | |
| 2-678 | CH₂C≡CCH₃ | CO₂Et | SO₂CF₃ | |
| 2-679 | CH₂C≡N | CO₂Et | SO₂CF₃ | |
| 2-680 | CH₂CH=CH₂ | CO₂Et | SO₂CF₃ | |
| 2-681 | CH₂CH=CHCH₃ | CO₂Et | SO₂CF₃ | |
| 2-682 | CH₂CH=C(CH₃)₃ | CO₂Et | SO₂CF₃ | |
| 2-683 | CH₂OCH₃ | CO₂Et | SO₂CF₃ | |
| 2-684 | CH₂CH₂OCH₃ | CO₂Et | SO₂CF₃ | |
| 2-685 | CH₂OCH₂CH₃ | CO₂Et | SO₂CF₃ | |
| 2-686 | CH₂CH₂OCH₂CH₃ | CO₂Et | SO₂CF₃ | |
| 2-687 | H | COCF₃ | SO₂CF₃ | |
| 2-688 | Me | COCF₃ | SO₂CF₃ | |
| 2-689 | Et | COCF₃ | SO₂CF₃ | |
| 2-690 | n-Pr | COCF₃ | SO₂CF₃ | |
| 2-691 | i-Pr | COCF₃ | SO₂CF₃ | |
| 2-692 | c-Pr | COCF₃ | SO₂CF₃ | |
| 2-693 | n-Bu | COCF₃ | SO₂CF₃ | |
| 2-694 | n-Pen | COCF₃ | SO₂CF₃ | |
| 2-695 | CH₂CF₃ | COCF₃ | SO₂CF₃ | |
| 2-696 | CH₂C₂F₅ | COCF₃ | SO₂CF₃ | |
| 2-697 | CH₂CHF₂ | COCF₃ | SO₂CF₃ | |
| 2-698 | CH₂CF₂CHF₂ | COCF₃ | SO₂CF₃ | |
| 2-699 | CH₂SCH₃ | COCF₃ | SO₂CF₃ | |
| 2-700 | CH₂SOCH₃ | COCF₃ | SO₂CF₃ | |
| 2-701 | CH₂SO₂CH₃ | COCF₃ | SO₂CF₃ | |
| 2-702 | CH₂SCH₂CH₃ | COCF₃ | SO₂CF₃ | |
| 2-703 | CH₂SOCH₂CH₃ | COCF₃ | SO₂CF₃ | |
| 2-704 | CH₂SO₂CH₂CH₃ | COCF₃ | SO₂CF₃ | |
| 2-705 | CH₂CH₂SCH₃ | COCF₃ | SO₂CF₃ | |
| 2-706 | CH₂CH₂SOCH₃ | COCF₃ | SO₂CF₃ | |
| 2-707 | CH₂CH₂SO₂CH₃ | COCF₃ | SO₂CF₃ | |
| 2-708 | CH₂CH₂SCH₂CH₃ | COCF₃ | SO₂CF₃ | |
| 2-709 | CH₂CH₂SOCH₂CH₃ | COCF₃ | SO₂CF₃ | |
| 2-710 | CH₂CH₂SO₂CH₂CH₃ | COCF₃ | SO₂CF₃ | |
| 2-711 | CH₂CH₂SCF₃ | COCF₃ | SO₂CF₃ | |
| 2-712 | CH₂CH₂SOCF₃ | COCF₃ | SO₂CF₃ | |
| 2-713 | CH₂CH₂SO₂CF₃ | COCF₃ | SO₂CF₃ | |
| 2-714 | CH₂Ph | COCF₃ | SO₂CF₃ | |
| 2-715 | CH₂C≡CH | COCF₃ | SO₂CF₃ | |
| 2-716 | CH₂C≡CCH₃ | COCF₃ | SO₂CF₃ | |
| 2-717 | CH₂C≡N | COCF₃ | SO₂CF₃ | |
| 2-718 | CH₂CH=CH₂ | COCF₃ | SO₂CF₃ | |
| 2-719 | CH₂CH=CHCH₃ | COCF₃ | SO₂CF₃ | |
| 2-720 | CH₂CH=C(CH₃)₃ | COCF₃ | SO₂CF₃ | |
| 2-721 | CH₂OCH₃ | COCF₃ | SO₂CF₃ | |
| 2-722 | CH₂CH₂OCH₃ | COCF₃ | SO₂CF₃ | |
| 2-723 | CH₂OCH₂CH₃ | COCF₃ | SO₂CF₃ | |
| 2-724 | CH₂CH₂OCH₂CH₃ | COCF₃ | SO₂CF₃ | |
| 2-725 | H | CSOMe | SO₂CF₃ | |
| 2-726 | Me | CSOMe | SO₂CF₃ | |
| 2-727 | Et | CSOMe | SO₂CF₃ | |
| 2-728 | n-Pr | CSOMe | SO₂CF₃ | |
| 2-729 | i-Pr | CSOMe | SO₂CF₃ | |
| 2-730 | c-Pr | CSOMe | SO₂CF₃ | |
| 2-731 | n-Bu | CSOMe | SO₂CF₃ | |
| 2-732 | n-Pen | CSOMe | SO₂CF₃ | |
| 2-733 | CH₂CF₃ | CSOMe | SO₂CF₃ | |
| 2-734 | CH₂C₂F₅ | CSOMe | SO₂CF₃ | |
| 2-735 | CH₂CHF₂ | CSOMe | SO₂CF₃ | |
| 2-736 | CH₂CF₂CHF₂ | CSOMe | SO₂CF₃ | |
| 2-737 | CH₂SCH₃ | CSOMe | SO₂CF₃ | |
| 2-738 | CH₂SOCH₃ | CSOMe | SO₂CF₃ | |
| 2-739 | CH₂SO₂CH₃ | CSOMe | SO₂CF₃ | |
| 2-740 | CH₂SCH₂CH₃ | CSOMe | SO₂CF₃ | |
| 2-741 | CH₂SOCH₂CH₃ | CSOMe | SO₂CF₃ | |
| 2-742 | CH₂SO₂CH₂CH₃ | CSOMe | SO₂CF₃ | |
| 2-743 | CH₂CH₂SCH₃ | CSOMe | SO₂CF₃ | |
| 2-744 | CH₂CH₂SOCH₃ | CSOMe | SO₂CF₃ | |
| 2-745 | CH₂CH₂SO₂CH₃ | CSOMe | SO₂CF₃ | |
| 2-746 | CH₂CH₂SCH₂CH₃ | CSOMe | SO₂CF₃ | |
| 2-747 | CH₂CH₂SOCH₂CH₃ | CSOMe | SO₂CF₃ | |
| 2-748 | CH₂CH₂SO₂CH₂CH₃ | CSOMe | SO₂CF₃ | |
| 2-749 | CH₂CH₂SCF₃ | CSOMe | SO₂CF₃ | |
| 2-750 | CH₂CH₂SOCF₃ | CSOMe | SO₂CF₃ | |
| 2-751 | CH₂CH₂SO₂CF₃ | CSOMe | SO₂CF₃ | |
| 2-752 | CH₂Ph | CSOMe | SO₂CF₃ | |
| 2-753 | CH₂C≡CH | CSOMe | SO₂CF₃ | |
| 2-754 | CH₂C≡CCH₃ | CSOMe | SO₂CF₃ | |
| 2-755 | CH₂C≡N | CSOMe | SO₂CF₃ | |
| 2-756 | CH₂CH=CH₂ | CSOMe | SO₂CF₃ | |
| 2-757 | CH₂CH=CHCH₃ | CSOMe | SO₂CF₃ | |
| 2-758 | CH₂CH=C(CH₃)₃ | CSOMe | SO₂CF₃ | |
| 2-759 | CH₂OCH₃ | CSOMe | SO₂CF₃ | |
| 2-760 | CH₂CH₂OCH₃ | CSOMe | SO₂CF₃ | |
| 2-761 | CH₂OCH₂CH₃ | CSOMe | SO₂CF₃ | |
| 2-762 | CH₂CH₂OCH₂CH₃ | CSOMe | SO₂CF₃ | |
| 2-763 | H | CSOEt | SO₂CF₃ | |
| 2-764 | Me | CSOEt | SO₂CF₃ | |
| 2-765 | Et | CSOEt | SO₂CF₃ | |
| 2-766 | n-Pr | CSOEt | SO₂CF₃ | |
| 2-767 | i-Pr | CSOEt | SO₂CF₃ | |
| 2-768 | c-Pr | CSOEt | SO₂CF₃ | |
| 2-769 | n-Bu | CSOEt | SO₂CF₃ | |
| 2-770 | n-Pen | CSOEt | SO₂CF₃ | |
| 2-771 | CH₂CF₃ | CSOEt | SO₂CF₃ | |
| 2-772 | CH₂C₂F₅ | CSOEt | SO₂CF₃ | |
| 2-773 | CH₂CHF₂ | CSOEt | SO₂CF₃ | |
| 2-774 | CH₂CF₂CHF₂ | CSOEt | SO₂CF₃ | |
| 2-775 | CH₂SCH₃ | CSOEt | SO₂CF₃ | |
| 2-776 | CH₂SOCH₃ | CSOEt | SO₂CF₃ | |
| 2-777 | CH₂SO₂CH₃ | CSOEt | SO₂CF₃ | |
| 2-778 | CH₂SCH₂CH₃ | CSOEt | SO₂CF₃ | |
| 2-779 | CH₂SOCH₂CH₃ | CSOEt | SO₂CF₃ | |
| 2-780 | CH₂SO₂CH₂CH₃ | CSOEt | SO₂CF₃ | |
| 2-781 | CH₂CH₂SCH₃ | CSOEt | SO₂CF₃ | |
| 2-782 | CH₂CH₂SOCH₃ | CSOEt | SO₂CF₃ | |
| 2-783 | CH₂CH₂SO₂CH₃ | CSOEt | SO₂CF₃ | |
| 2-784 | CH₂CH₂SCH₂CH₃ | CSOEt | SO₂CF₃ | |
| 2-785 | CH₂CH₂SOCH₂CH₃ | CSOEt | SO₂CF₃ | |
| 2-786 | CH₂CH₂SO₂CH₂CH₃ | CSOEt | SO₂CF₃ | |
| 2-787 | CH₂CH₂SCF₃ | CSOEt | SO₂CF₃ | |
| 2-788 | CH₂CH₂SOCF₃ | CSOEt | SO₂CF₃ | |
| 2-789 | CH₂CH₂SO₂CF₃ | CSOEt | SO₂CF₃ | |
| 2-790 | CH₂Ph | CSOEt | SO₂CF₃ | |
| 2-791 | CH₂C≡CH | CSOEt | SO₂CF₃ | |
| 2-792 | CH₂C≡CCH₃ | CSOEt | SO₂CF₃ | |
| 2-793 | CH₂C≡N | CSOEt | SO₂CF₃ | |
| 2-794 | CH₂CH=CH₂ | CSOEt | SO₂CF₃ | |
| 2-795 | CH₂CH=CHCH₃ | CSOEt | SO₂CF₃ | |
| 2-796 | CH₂CH=C(CH₃)₃ | CSOEt | SO₂CF₃ | |
| 2-797 | CH₂OCH₃ | CSOEt | SO₂CF₃ | |
| 2-798 | CH₂CH₂OCH₃ | CSOEt | SO₂CF₃ | |
| 2-799 | CH₂OCH₂CH₃ | CSOEt | SO₂CF₃ | |
| 2-800 | CH₂CH₂OCH₂CH₃ | CSOEt | SO₂CF₃ | |
| 2-801 | H | CSN(Me)₂ | SO₂CF₃ | |
| 2-802 | Me | CSN(Me)₂ | SO₂CF₃ | |
| 2-803 | Et | CSN(Me)₂ | SO₂CF₃ | |
| 2-804 | n-Pr | CSN(Me)₂ | SO₂CF₃ | |

TABLE 2-continued

| Compound No. | R³ | R⁴ | R⁵ | Physical property |
|---|---|---|---|---|
| 2-805 | i-Pr | CSN(Me)₂ | SO₂CF₃ | |
| 2-806 | c-Pr | CSN(Me)₂ | SO₂CF₃ | |
| 2-807 | n-Bu | CSN(Me)₂ | SO₂CF₃ | |
| 2-808 | n-Pen | CSN(Me)₂ | SO₂CF₃ | |
| 2-809 | CH₂CF₃ | CSN(Me)₂ | SO₂CF₃ | |
| 2-810 | CH₂C₂F₅ | CSN(Me)₂ | SO₂CF₃ | |
| 2-811 | CH₂CHF₂ | CSN(Me)₂ | SO₂CF₃ | |
| 2-812 | CH₂CF₂CHF₂ | CSN(Me)₂ | SO₂CF₃ | |
| 2-813 | CH₂SCH₃ | CSN(Me)₂ | SO₂CF₃ | |
| 2-814 | CH₂SOCH₃ | CSN(Me)₂ | SO₂CF₃ | |
| 2-815 | CH₂SO₂CH₃ | CSN(Me)₂ | SO₂CF₃ | |
| 2-816 | CH₂SCH₂CH₃ | CSN(Me)₂ | SO₂CF₃ | |
| 2-817 | CH₂SOCH₂CH₃ | CSN(Me)₂ | SO₂CF₃ | |
| 2-818 | CH₂SO₂CH₂CH₃ | CSN(Me)₂ | SO₂CF₃ | |
| 2-819 | CH₂CH₂SCH₃ | CSN(Me)₂ | SO₂CF₃ | |
| 2-820 | CH₂CH₂SOCH₃ | CSN(Me)₂ | SO₂CF₃ | |
| 2-821 | CH₂CH₂SO₂CH₃ | CSN(Me)₂ | SO₂CF₃ | |
| 2-822 | CH₂CH₂SCH₂CH₃ | CSN(Me)₂ | SO₂CF₃ | |
| 2-823 | CH₂CH₂SOCH₂CH₃ | CSN(Me)₂ | SO₂CF₃ | |
| 2-824 | CH₂CH₂SO₂CH₂CH₃ | CSN(Me)₂ | SO₂CF₃ | |
| 2-825 | CH₂CH₂SCF₃ | CSN(Me)₂ | SO₂CF₃ | |
| 2-826 | CH₂CH₂SOCF₃ | CSN(Me)₂ | SO₂CF₃ | |
| 2-827 | CH₂CH₂SO₂CF₃ | CSN(Me)₂ | SO₂CF₃ | |
| 2-828 | CH₂Ph | CSN(Me)₂ | SO₂CF₃ | |
| 2-829 | CH₂C≡CH | CSN(Me)₂ | SO₂CF₃ | |
| 2-830 | CH₂C≡CCH₃ | CSN(Me)₂ | SO₂CF₃ | |
| 2-831 | CH₂C≡N | CSN(Me)₂ | SO₂CF₃ | |
| 2-832 | CH₂CH=CH₂ | CSN(Me)₂ | SO₂CF₃ | |
| 2-833 | CH₂CH=CHCH₃ | CSN(Me)₂ | SO₂CF₃ | |
| 2-834 | CH₂CH=C(CH₃)₃ | CSN(Me)₂ | SO₂CF₃ | |
| 2-835 | CH₂OCH₃ | CSN(Me)₂ | SO₂CF₃ | |
| 2-836 | CH₂CH₂OCH₃ | CSN(Me)₂ | SO₂CF₃ | |
| 2-837 | CH₂OCH₂CH₃ | CSN(Me)₂ | SO₂CF₃ | |
| 2-838 | CH₂CH₂OCH₂CH₃ | CSN(Me)₂ | SO₂CF₃ | |
| 2-839 | H | CSNHEt | SO₂CF₃ | |
| 2-840 | Me | CSNHEt | SO₂CF₃ | |
| 2-841 | Et | CSNHEt | SO₂CF₃ | |
| 2-842 | n-Pr | CSNHEt | SO₂CF₃ | |
| 2-843 | i-Pr | CSNHEt | SO₂CF₃ | |
| 2-844 | c-Pr | CSNHEt | SO₂CF₃ | |
| 2-845 | n-Bu | CSNHEt | SO₂CF₃ | |
| 2-846 | n-Pen | CSNHEt | SO₂CF₃ | |
| 2-847 | CH₂CF₃ | CSNHEt | SO₂CF₃ | |
| 2-848 | CH₂C₂F₅ | CSNHEt | SO₂CF₃ | |
| 2-849 | CH₂CHF₂ | CSNHEt | SO₂CF₃ | |
| 2-850 | CH₂CF₂CHF₂ | CSNHEt | SO₂CF₃ | |
| 2-851 | CH₂SCH₃ | CSNHEt | SO₂CF₃ | |
| 2-852 | CH₂SOCH₃ | CSNHEt | SO₂CF₃ | |
| 2-853 | CH₂SO₂CH₃ | CSNHEt | SO₂CF₃ | |
| 2-854 | CH₂SCH₂CH₃ | CSNHEt | SO₂CF₃ | |
| 2-855 | CH₂SOCH₂CH₃ | CSNHEt | SO₂CF₃ | |
| 2-856 | CH₂SO₂CH₂CH₃ | CSNHEt | SO₂CF₃ | |
| 2-857 | CH₂CH₂SCH₃ | CSNHEt | SO₂CF₃ | |
| 2-858 | CH₂CH₂SOCH₃ | CSNHEt | SO₂CF₃ | |
| 2-859 | CH₂CH₂SO₂CH₃ | CSNHEt | SO₂CF₃ | |
| 2-860 | CH₂CH₂SCH₂CH₃ | CSNHEt | SO₂CF₃ | |
| 2-861 | CH₂CH₂SOCH₂CH₃ | CSNHEt | SO₂CF₃ | |
| 2-862 | CH₂CH₂SO₂CH₂CH₃ | CSNHEt | SO₂CF₃ | |
| 2-863 | CH₂CH₂SCF₃ | CSNHEt | SO₂CF₃ | |
| 2-864 | CH₂CH₂SOCF₃ | CSNHEt | SO₂CF₃ | |
| 2-865 | CH₂CH₂SO₂CF₃ | CSNHEt | SO₂CF₃ | |
| 2-866 | CH₂Ph | CSNHEt | SO₂CF₃ | |
| 2-867 | CH₂C≡CH | CSNHEt | SO₂CF₃ | |
| 2-868 | CH₂C≡CCH₃ | CSNHEt | SO₂CF₃ | |
| 2-869 | CH₂C≡N | CSNHEt | SO₂CF₃ | |
| 2-870 | CH₂CH=CH₂ | CSNHEt | SO₂CF₃ | |
| 2-871 | CH₂CH=CHCH₃ | CSNHEt | SO₂CF₃ | |
| 2-872 | CH₂CH=C(CH₃)₃ | CSNHEt | SO₂CF₃ | |
| 2-873 | CH₂OCH₃ | CSNHEt | SO₂CF₃ | |
| 2-874 | CH₂CH₂OCH₃ | CSNHEt | SO₂CF₃ | |
| 2-875 | CH₂OCH₂CH₃ | CSNHEt | SO₂CF₃ | |
| 2-876 | CH₂CH₂OCH₂CH₃ | CSNHEt | SO₂CF₃ | |
| 2-877 | H | SO₂Me | SO₂CF₃ | |
| 2-878 | Me | SO₂Me | SO₂CF₃ | |
| 2-879 | Et | SO₂Me | SO₂CF₃ | |
| 2-880 | n-Pr | SO₂Me | SO₂CF₃ | |
| 2-881 | i-Pr | SO₂Me | SO₂CF₃ | |
| 2-882 | c-Pr | SO₂Me | SO₂CF₃ | |
| 2-883 | n-Bu | SO₂Me | SO₂CF₃ | |
| 2-884 | n-Pen | SO₂Me | SO₂CF₃ | |
| 2-885 | CH₂CF₃ | SO₂Me | SO₂CF₃ | |
| 2-886 | CH₂C₂F₅ | SO₂Me | SO₂CF₃ | |
| 2-887 | CH₂CHF₂ | SO₂Me | SO₂CF₃ | |
| 2-888 | CH₂CF₂CHF₂ | SO₂Me | SO₂CF₃ | |
| 2-889 | CH₂SCH₃ | SO₂Me | SO₂CF₃ | |
| 2-890 | CH₂SOCH₃ | SO₂Me | SO₂CF₃ | |
| 2-891 | CH₂SO₂CH₃ | SO₂Me | SO₂CF₃ | |
| 2-892 | CH₂SCH₂CH₃ | SO₂Me | SO₂CF₃ | |
| 2-893 | CH₂SOCH₂CH₃ | SO₂Me | SO₂CF₃ | |
| 2-894 | CH₂SO₂CH₂CH₃ | SO₂Me | SO₂CF₃ | |
| 2-895 | CH₂CH₂SCH₃ | SO₂Me | SO₂CF₃ | |
| 2-896 | CH₂CH₂SOCH₃ | SO₂Me | SO₂CF₃ | |
| 2-897 | CH₂CH₂SO₂CH₃ | SO₂Me | SO₂CF₃ | |
| 2-898 | CH₂CH₂SCH₂CH₃ | SO₂Me | SO₂CF₃ | |
| 2-899 | CH₂CH₂SOCH₂CH₃ | SO₂Me | SO₂CF₃ | |
| 2-900 | CH₂CH₂SO₂CH₂CH₃ | SO₂Me | SO₂CF₃ | |
| 2-901 | CH₂CH₂SCF₃ | SO₂Me | SO₂CF₃ | |
| 2-902 | CH₂CH₂SOCF₃ | SO₂Me | SO₂CF₃ | |
| 2-903 | CH₂CH₂SO₂CF₃ | SO₂Me | SO₂CF₃ | |
| 2-904 | CH₂Ph | SO₂Me | SO₂CF₃ | |
| 2-905 | CH₂C≡CH | SO₂Me | SO₂CF₃ | |
| 2-906 | CH₂C≡CCH₃ | SO₂Me | SO₂CF₃ | |
| 2-907 | CH₂C≡N | SO₂Me | SO₂CF₃ | |
| 2-908 | CH₂CH=CH₂ | SO₂Me | SO₂CF₃ | |
| 2-909 | CH₂CH=CHCH₃ | SO₂Me | SO₂CF₃ | |
| 2-910 | CH₂CH=C(CH₃)₃ | SO₂Me | SO₂CF₃ | |
| 2-911 | CH₂OCH₃ | SO₂Me | SO₂CF₃ | |
| 2-912 | CH₂CH₂OCH₃ | SO₂Me | SO₂CF₃ | |
| 2-913 | CH₂OCH₂CH₃ | SO₂Me | SO₂CF₃ | |
| 2-914 | CH₂CH₂OCH₂CH₃ | SO₂Me | SO₂CF₃ | |
| 2-915 | n-Pr | CH₂OCH₃ | SCF₃ | |
| 2-916 | CH₂CF₃ | CH₂OCH₃ | SCF₃ | 91-92 |
| 2-917 | CH₂C₂F₅ | CH₂OCH₃ | SCF₃ | |
| 2-918 | CH₂CHF₂ | CH₂OCH₃ | SCF₃ | |
| 2-919 | CH₂CF₂CHF₂ | CH₂OCH₃ | SCF₃ | |
| 2-920 | n-Pr | CH₂OCH₃ | SO₂CF₃ | |
| 2-921 | CH₂CF₃ | CH₂OCH₃ | SO₂CF₃ | |
| 2-922 | CH₂C₂F₅ | CH₂OCH₃ | SO₂CF₃ | |
| 2-923 | CH₂CHF₂ | CH₂OCH₃ | SO₂CF₃ | |
| 2-924 | CH₂CF₂CHF₂ | CH₂OCH₃ | SO₂CF₃ | |

[Chem. 12]

(1B-1)

TABLE 3

| Compound No. | R³ | R⁴ | R⁵ | Physical property |
|---|---|---|---|---|
| 3-1 | H | H | CF₃ | |
| 3-2 | Me | H | CF₃ | |
| 3-3 | Et | H | CF₃ | 105-106 |
| 3-4 | n-Pr | H | CF₃ | |

TABLE 3-continued

| Compound No. | R³ | R⁴ | R⁵ | Physical property |
|---|---|---|---|---|
| 3-5 | i-Pr | H | CF₃ | |
| 3-6 | c-Pr | H | CF₃ | |
| 3-7 | n-Bu | H | CF₃ | |
| 3-8 | n-Pen | H | CF₃ | |
| 3-9 | CH₂CF₃ | H | CF₃ | 86-87 |
| 3-10 | CH₂C₂F₅ | H | CF₃ | |
| 3-11 | CH₂CHF₂ | H | CF₃ | |
| 3-12 | CH₂CF₂CHF₂ | H | CF₃ | |
| 3-13 | CH₂SCH₃ | H | CF₃ | |
| 3-14 | CH₂SOCH₃ | H | CF₃ | |
| 3-15 | CH₂SO₂CH₃ | H | CF₃ | |
| 3-16 | CH₂SCH₂CH₃ | H | CF₃ | |
| 3-17 | CH₂SOCH₂CH₃ | H | CF₃ | |
| 3-18 | CH₂SO₂CH₂CH₃ | H | CF₃ | |
| 3-19 | CH₂CH₂SCH₃ | H | CF₃ | |
| 3-20 | CH₂CH₂SOCH₃ | H | CF₃ | |
| 3-21 | CH₂CH₂SO₂CH₃ | H | CF₃ | |
| 3-22 | CH₂CH₂SCH₂CH₃ | H | CF₃ | |
| 3-23 | CH₂CH₂SOCH₂CH₃ | H | CF₃ | |
| 3-24 | CH₂CH₂SO₂CH₂CH₃ | H | CF₃ | |
| 3-25 | CH₂CH₂SCF₃ | H | CF₃ | |
| 3-26 | CH₂CH₂SOCF₃ | H | CF₃ | |
| 3-27 | CH₂CH₂SO₂CF₃ | H | CF₃ | |
| 3-28 | CH₂Ph | H | CF₃ | |
| 3-29 | CH₂C≡CH | H | CF₃ | |
| 3-30 | CH₂C≡CCH₃ | H | CF₃ | |
| 3-31 | CH₂C≡N | H | CF₃ | |
| 3-32 | CH₂CH=CH₂ | H | CF₃ | |
| 3-33 | CH₂CH=CHCH₃ | H | CF₃ | |
| 3-34 | CH₂CH=C(CH₃)₃ | H | CF₃ | |
| 3-35 | CH₂OCH₃ | H | CF₃ | |
| 3-36 | CH₂CH₂OCH₃ | H | CF₃ | |
| 3-37 | CH₂OCH₂CH₃ | H | CF₃ | |
| 3-38 | CH₂CH₂OCH₂CH₃ | H | CF₃ | |
| 3-39 | Ph | H | CF₃ | |
| 3-40 | 4-SMePh | H | CF₃ | |
| 3-41 | 4-CF₃Ph | H | CF₃ | |
| 3-42 | 2-F,4-Cl—Ph | H | CF₃ | |
| 3-43 | Me | Me | CF₃ | |
| 3-44 | Et | Me | CF₃ | |
| 3-45 | n-Pr | Me | CF₃ | |
| 3-46 | i-Pr | Me | CF₃ | |
| 3-47 | c-Pr | Me | CF₃ | |
| 3-48 | n-Bu | Me | CF₃ | |
| 3-49 | n-Pen | Me | CF₃ | |
| 3-50 | CH₂CF₃ | Me | CF₃ | 110-111 |
| 3-51 | CH₂C₂F₅ | Me | CF₃ | |
| 3-52 | CH₂CHF₂ | Me | CF₃ | |
| 3-53 | CH₂CF₂CHF₂ | Me | CF₃ | |
| 3-54 | CH₂SCH₃ | Me | CF₃ | |
| 3-55 | CH₂SOCH₃ | Me | CF₃ | |
| 3-56 | CH₂SO₂CH₃ | Me | CF₃ | |
| 3-57 | CH₂SCH₂CH₃ | Me | CF₃ | |
| 3-58 | CH₂SOCH₂CH₃ | Me | CF₃ | |
| 3-59 | CH₂SO₂CH₂CH₃ | Me | CF₃ | |
| 3-60 | CH₂CH₂SCH₃ | Me | CF₃ | |
| 3-61 | CH₂CH₂SOCH₃ | Me | CF₃ | |
| 3-62 | CH₂CH₂SO₂CH₃ | Me | CF₃ | |
| 3-63 | CH₂CH₂SCH₂CH₃ | Me | CF₃ | |
| 3-64 | CH₂CH₂SOCH₂CH₃ | Me | CF₃ | |
| 3-65 | CH₂CH₂SO₂CH₂CH₃ | Me | CF₃ | |
| 3-66 | CH₂CH₂SCF₃ | Me | CF₃ | |
| 3-67 | CH₂CH₂SOCF₃ | Me | CF₃ | |
| 3-68 | CH₂CH₂SO₂CF₃ | Me | CF₃ | |
| 3-69 | CH₂Ph | Me | CF₃ | |
| 3-70 | CH₂C≡CH | Me | CF₃ | |
| 3-71 | CH₂C≡CCH₃ | Me | CF₃ | |
| 3-72 | CH₂C≡N | Me | CF₃ | |
| 3-73 | CH₂CH=CH₂ | Me | CF₃ | |
| 3-74 | CH₂CH=CHCH₃ | Me | CF₃ | |
| 3-75 | CH₂CH=C(CH₃)₃ | Me | CF₃ | |
| 3-76 | CH₂OCH₃ | Me | CF₃ | |
| 3-77 | CH₂CH₂OCH₃ | Me | CF₃ | |
| 3-78 | CH₂OCH₂CH₃ | Me | CF₃ | |
| 3-79 | CH₂CH₂OCH₂CH₃ | Me | CF₃ | |
| 3-80 | Et | Et | CF₃ | |
| 3-81 | n-Pr | Et | CF₃ | |
| 3-82 | i-Pr | Et | CF₃ | |
| 3-83 | c-Pr | Et | CF₃ | |
| 3-84 | n-Bu | Et | CF₃ | |
| 3-85 | n-Pen | Et | CF₃ | |
| 3-86 | CH₂CF₃ | Et | CF₃ | |
| 3-87 | CH₂C₂F₅ | Et | CF₃ | |
| 3-88 | CH₂CHF₂ | Et | CF₃ | |
| 3-89 | CH₂CF₂CHF₂ | Et | CF₃ | |
| 3-90 | CH₂SCH₃ | Et | CF₃ | |
| 3-91 | CH₂SOCH₃ | Et | CF₃ | |
| 3-92 | CH₂SO₂CH₃ | Et | CF₃ | |
| 3-93 | CH₂SCH₂CH₃ | Et | CF₃ | |
| 3-94 | CH₂SOCH₂CH₃ | Et | CF₃ | |
| 3-95 | CH₂SO₂CH₂CH₃ | Et | CF₃ | |
| 3-96 | CH₂CH₂SCH₃ | Et | CF₃ | |
| 3-97 | CH₂CH₂SOCH₃ | Et | CF₃ | |
| 3-98 | CH₂CH₂SO₂CH₃ | Et | CF₃ | |
| 3-99 | CH₂CH₂SCH₂CH₃ | Et | CF₃ | |
| 3-100 | CH₂CH₂SOCH₂CH₃ | Et | CF₃ | |
| 3-101 | CH₂CH₂SO₂CH₂CH₃ | Et | CF₃ | |
| 3-102 | CH₂CH₂SCF₃ | Et | CF₃ | |
| 3-103 | CH₂CH₂SOCF₃ | Et | CF₃ | |
| 3-104 | CH₂CH₂SO₂CF₃ | Et | CF₃ | |
| 3-105 | CH₂Ph | Et | CF₃ | |
| 3-106 | CH₂C≡CH | Et | CF₃ | |
| 3-107 | CH₂C≡CCH₃ | Et | CF₃ | |
| 3-108 | CH₂C≡N | Et | CF₃ | |
| 3-109 | CH₂CH=CH₂ | Et | CF₃ | |
| 3-110 | CH₂CH=CHCH₃ | Et | CF₃ | |
| 3-111 | CH₂CH=C(CH₃)₃ | Et | CF₃ | |
| 3-112 | CH₂OCH₃ | Et | CF₃ | |
| 3-113 | CH₂CH₂OCH₃ | Et | CF₃ | |
| 3-114 | CH₂OCH₂CH₃ | Et | CF₃ | |
| 3-115 | CH₂CH₂OCH₂CH₃ | Et | CF₃ | |
| 3-116 | H | Ac | CF₄ | 245-246 |
| 3-117 | Me | Ac | CF₃ | |
| 3-118 | Et | Ac | CF₃ | 211-212 |
| 3-119 | n-Pr | Ac | CF₃ | |
| 3-120 | i-Pr | Ac | CF₃ | |
| 3-121 | c-Pr | Ac | CF₃ | |
| 3-122 | n-Bu | Ac | CF₃ | |
| 3-123 | n-Pen | Ac | CF₃ | |
| 3-124 | CH₂CF₃ | Ac | CF₃ | |
| 3-125 | CH₂C₂F₅ | Ac | CF₃ | |
| 3-126 | CH₂CHF₂ | Ac | CF₃ | |
| 3-127 | CH₂CF₂CHF₂ | Ac | CF₃ | |
| 3-128 | CH₂SCH₃ | Ac | CF₃ | |
| 3-129 | CH₂SOCH₃ | Ac | CF₃ | |
| 3-130 | CH₂SO₂CH₃ | Ac | CF₃ | |
| 3-131 | CH₂SCH₂CH₃ | Ac | CF₃ | |
| 3-132 | CH₂SOCH₂CH₃ | Ac | CF₃ | |
| 3-133 | CH₂SO₂CH₂CH₃ | Ac | CF₃ | |
| 3-134 | CH₂CH₂SCH₃ | Ac | CF₃ | |
| 3-135 | CH₂CH₂SOCH₃ | Ac | CF₃ | |
| 3-136 | CH₂CH₂SO₂CH₃ | Ac | CF₃ | |
| 3-137 | CH₂CH₂SCH₂CH₃ | Ac | CF₃ | |
| 3-138 | CH₂CH₂SOCH₂CH₃ | Ac | CF₃ | |
| 3-139 | CH₂CH₂SO₂CH₂CH₃ | Ac | CF₃ | |
| 3-140 | CH₂CH₂SCF₃ | Ac | CF₃ | |
| 3-141 | CH₂CH₂SOCF₃ | Ac | CF₃ | |
| 3-142 | CH₂CH₂SO₂CF₃ | Ac | CF₃ | |
| 3-143 | CH₂Ph | Ac | CF₃ | |
| 3-144 | CH₂C≡CH | Ac | CF₃ | |
| 3-145 | CH₂C≡CCH₃ | Ac | CF₃ | |
| 3-146 | CH₂C≡N | Ac | CF₃ | |
| 3-147 | CH₂CH=CH₂ | Ac | CF₃ | |
| 3-148 | CH₂CH=CHCH₃ | Ac | CF₃ | |
| 3-149 | CH₂CH=C(CH₃)₃ | Ac | CF₃ | |
| 3-150 | CH₂OCH₃ | Ac | CF₃ | |
| 3-151 | CH₂CH₂OCH₃ | Ac | CF₃ | |
| 3-152 | CH₂OCH₂CH₃ | Ac | CF₃ | |
| 3-153 | CH₂CH₂OCH₂CH₃ | Ac | CF₃ | |
| 3-154 | H | CO₂Me | CF₃ | 78-79 |
| 3-155 | Me | CO₂Me | CF₃ | |
| 3-156 | Et | CO₂Me | CF₃ | |
| 3-157 | n-Pr | CO₂Me | CF₃ | |
| 3-158 | i-Pr | CO₂Me | CF₃ | |

TABLE 3-continued

| Compound No. | $R^3$ | $R^4$ | $R^5$ | Physical property |
|---|---|---|---|---|
| 3-159 | c-Pr | $CO_2Me$ | $CF_3$ | |
| 3-160 | n-Bu | $CO_2Me$ | $CF_3$ | |
| 3-161 | n-Pen | $CO_2Me$ | $CF_3$ | |
| 3-162 | $CH_2CF_3$ | $CO_2Me$ | $CF_3$ | |
| 3-163 | $CH_2C_2F_5$ | $CO_2Me$ | $CF_3$ | |
| 3-164 | $CH_2CHF_2$ | $CO_2Me$ | $CF_3$ | |
| 3-165 | $CH_2CF_2CHF_2$ | $CO_2Me$ | $CF_3$ | |
| 3-166 | $CH_2SCH_3$ | $CO_2Me$ | $CF_3$ | |
| 3-167 | $CH_2SOCH_3$ | $CO_2Me$ | $CF_3$ | |
| 3-168 | $CH_2SO_2CH_3$ | $CO_2Me$ | $CF_3$ | |
| 3-169 | $CH_2SCH_2CH_3$ | $CO_2Me$ | $CF_3$ | |
| 3-170 | $CH_2SOCH_2CH_3$ | $CO_2Me$ | $CF_3$ | |
| 3-171 | $CH_2SO_2CH_2CH_3$ | $CO_2Me$ | $CF_3$ | |
| 3-172 | $CH_2CH_2SCH_3$ | $CO_2Me$ | $CF_3$ | |
| 3-173 | $CH_2CH_2SOCH_3$ | $CO_2Me$ | $CF_3$ | |
| 3-174 | $CH_2CH_2SO_2CH_3$ | $CO_2Me$ | $CF_3$ | |
| 3-175 | $CH_2CH_2SCH_2CH_3$ | $CO_2Me$ | $CF_3$ | |
| 3-176 | $CH_2CH_2SOCH_2CH_3$ | $CO_2Me$ | $CF_3$ | |
| 3-177 | $CH_2CH_2SO_2CH_2CH_3$ | $CO_2Me$ | $CF_3$ | |
| 3-178 | $CH_2CH_2SCF_3$ | $CO_2Me$ | $CF_3$ | |
| 3-179 | $CH_2CH_2SOCF_3$ | $CO_2Me$ | $CF_3$ | |
| 3-180 | $CH_2CH_2SO_2CF_3$ | $CO_2Me$ | $CF_3$ | |
| 3-181 | $CH_2Ph$ | $CO_2Me$ | $CF_3$ | |
| 3-182 | $CH_2C{\equiv}CH$ | $CO_2Me$ | $CF_3$ | |
| 3-183 | $CH_2C{\equiv}CCH_3$ | $CO_2Me$ | $CF_3$ | |
| 3-184 | $CH_2C{\equiv}N$ | $CO_2Me$ | $CF_3$ | |
| 3-185 | $CH_2CH{=}CH_2$ | $CO_2Me$ | $CF_3$ | |
| 3-186 | $CH_2CH{=}CHCH_3$ | $CO_2Me$ | $CF_3$ | |
| 3-187 | $CH_2CH{=}C(CH_3)_3$ | $CO_2Me$ | $CF_3$ | |
| 3-188 | $CH_2OCH_3$ | $CO_2Me$ | $CF_3$ | |
| 3-189 | $CH_2CH_2OCH_3$ | $CO_2Me$ | $CF_3$ | |
| 3-190 | $CH_2OCH_2CH_3$ | $CO_2Me$ | $CF_3$ | |
| 3-191 | $CH_2CH_2OCH_2CH_3$ | $CO_2Me$ | $CF_3$ | |
| 3-192 | H | $CO_2Et$ | $CF_3$ | |
| 3-193 | Me | $CO_2Et$ | $CF_3$ | |
| 3-194 | Et | $CO_2Et$ | $CF_3$ | |
| 3-195 | n-Pr | $CO_2Et$ | $CF_3$ | |
| 3-196 | i-Pr | $CO_2Et$ | $CF_3$ | |
| 3-197 | c-Pr | $CO_2Et$ | $CF_3$ | |
| 3-198 | n-Bu | $CO_2Et$ | $CF_3$ | |
| 3-199 | n-Pen | $CO_2Et$ | $CF_3$ | |
| 3-200 | $CH_2CF_3$ | $CO_2Et$ | $CF_3$ | |
| 3-201 | $CH_2C_2F_5$ | $CO_2Et$ | $CF_3$ | |
| 3-202 | $CH_2CHF_2$ | $CO_2Et$ | $CF_3$ | |
| 3-203 | $CH_2CF_2CHF_2$ | $CO_2Et$ | $CF_3$ | |
| 3-204 | $CH_2SCH_3$ | $CO_2Et$ | $CF_3$ | |
| 3-205 | $CH_2SOCH_3$ | $CO_2Et$ | $CF_3$ | |
| 3-206 | $CH_2SO_2CH_3$ | $CO_2Et$ | $CF_3$ | |
| 3-207 | $CH_2SCH_2CH_3$ | $CO_2Et$ | $CF_3$ | |
| 3-208 | $CH_2SOCH_2CH_3$ | $CO_2Et$ | $CF_3$ | |
| 3-209 | $CH_2SO_2CH_2CH_3$ | $CO_2Et$ | $CF_3$ | |
| 3-210 | $CH_2CH_2SCH_3$ | $CO_2Et$ | $CF_3$ | |
| 3-211 | $CH_2CH_2SOCH_3$ | $CO_2Et$ | $CF_3$ | |
| 3-212 | $CH_2CH_2SO_2CH_3$ | $CO_2Et$ | $CF_3$ | |
| 3-213 | $CH_2CH_2SCH_2CH_3$ | $CO_2Et$ | $CF_3$ | |
| 3-214 | $CH_2CH_2SOCH_2CH_3$ | $CO_2Et$ | $CF_3$ | |
| 3-215 | $CH_2CH_2SO_2CH_2CH_3$ | $CO_2Et$ | $CF_3$ | |
| 3-216 | $CH_2CH_2SCF_3$ | $CO_2Et$ | $CF_3$ | |
| 3-217 | $CH_2CH_2SOCF_3$ | $CO_2Et$ | $CF_3$ | |
| 3-218 | $CH_2CH_2SO_2CF_3$ | $CO_2Et$ | $CF_3$ | |
| 3-219 | $CH_2Ph$ | $CO_2Et$ | $CF_3$ | |
| 3-220 | $CH_2C{\equiv}CH$ | $CO_2Et$ | $CF_3$ | |
| 3-221 | $CH_2C{\equiv}CCH_3$ | $CO_2Et$ | $CF_3$ | |
| 3-222 | $CH_2C{\equiv}N$ | $CO_2Et$ | $CF_3$ | |
| 3-223 | $CH_2CH{=}CH_2$ | $CO_2Et$ | $CF_3$ | |
| 3-224 | $CH_2CH{=}CHCH_3$ | $CO_2Et$ | $CF_3$ | |
| 3-225 | $CH_2CH{=}C(CH_3)_3$ | $CO_2Et$ | $CF_3$ | |
| 3-226 | $CH_2OCH_3$ | $CO_2Et$ | $CF_3$ | |
| 3-227 | $CH_2CH_2OCH_3$ | $CO_2Et$ | $CF_3$ | |
| 3-228 | $CH_2OCH_2CH_3$ | $CO_2Et$ | $CF_3$ | |
| 3-229 | $CH_2CH_2OCH_2CH_3$ | $CO_2Et$ | $CF_3$ | |
| 3-230 | H | $COCF_3$ | $CF_3$ | |
| 3-231 | Me | $COCF_3$ | $CF_3$ | |
| 3-232 | Et | $COCF_3$ | $CF_3$ | |
| 3-233 | n-Pr | $COCF_3$ | $CF_3$ | |
| 3-234 | i-Pr | $COCF_3$ | $CF_3$ | |
| 3-235 | c-Pr | $COCF_3$ | $CF_3$ | |
| 3-236 | n-Bu | $COCF_3$ | $CF_3$ | |
| 3-237 | n-Pen | $COCF_3$ | $CF_3$ | |
| 3-238 | $CH_2CF_3$ | $COCF_3$ | $CF_3$ | |
| 3-239 | $CH_2C_2F_5$ | $COCF_3$ | $CF_3$ | |
| 3-240 | $CH_2CHF_2$ | $COCF_3$ | $CF_3$ | |
| 3-241 | $CH_2CF_2CHF_2$ | $COCF_3$ | $CF_3$ | |
| 3-242 | $CH_2SCH_3$ | $COCF_3$ | $CF_3$ | |
| 3-243 | $CH_2SOCH_3$ | $COCF_3$ | $CF_3$ | |
| 3-244 | $CH_2SO_2CH_3$ | $COCF_3$ | $CF_3$ | |
| 3-245 | $CH_2SCH_2CH_3$ | $COCF_3$ | $CF_3$ | |
| 3-246 | $CH_2SOCH_2CH_3$ | $COCF_3$ | $CF_3$ | |
| 3-247 | $CH_2SO_2CH_2CH_3$ | $COCF_3$ | $CF_3$ | |
| 3-248 | $CH_2CH_2SCH_3$ | $COCF_3$ | $CF_3$ | |
| 3-249 | $CH_2CH_2SOCH_3$ | $COCF_3$ | $CF_3$ | |
| 3-250 | $CH_2CH_2SO_2CH_3$ | $COCF_3$ | $CF_3$ | |
| 3-251 | $CH_2CH_2SCH_2CH_3$ | $COCF_3$ | $CF_3$ | |
| 3-252 | $CH_2CH_2SOCH_2CH_3$ | $COCF_3$ | $CF_3$ | |
| 3-253 | $CH_2CH_2SO_2CH_2CH_3$ | $COCF_3$ | $CF_3$ | |
| 3-254 | $CH_2CH_2SCF_3$ | $COCF_3$ | $CF_3$ | |
| 3-255 | $CH_2CH_2SOCF_3$ | $COCF_3$ | $CF_3$ | |
| 3-256 | $CH_2CH_2SO_2CF_3$ | $COCF_3$ | $CF_3$ | |
| 3-257 | $CH_2Ph$ | $COCF_3$ | $CF_3$ | |
| 3-258 | $CH_2C{\equiv}CH$ | $COCF_3$ | $CF_3$ | |
| 3-259 | $CH_2C{\equiv}CCH_3$ | $COCF_3$ | $CF_3$ | |
| 3-260 | $CH_2C{\equiv}N$ | $COCF_3$ | $CF_3$ | |
| 3-261 | $CH_2CH{=}CH_2$ | $COCF_3$ | $CF_3$ | |
| 3-262 | $CH_2CH{=}CHCH_3$ | $COCF_3$ | $CF_3$ | |
| 3-263 | $CH_2CH{=}C(CH_3)_3$ | $COCF_3$ | $CF_3$ | |
| 3-264 | $CH_2OCH_3$ | $COCF_3$ | $CF_3$ | |
| 3-265 | $CH_2CH_2OCH_3$ | $COCF_3$ | $CF_3$ | |
| 3-266 | $CH_2OCH_2CH_3$ | $COCF_3$ | $CF_3$ | |
| 3-267 | $CH_2CH_2OCH_2CH_3$ | $COCF_3$ | $CF_3$ | |
| 3-268 | H | $COCF_3$ | $CF_3$ | |
| 3-269 | Me | CSOMe | $CF_3$ | |
| 3-270 | Et | CSOMe | $CF_3$ | |
| 3-271 | n-Pr | CSOMe | $CF_3$ | |
| 3-272 | i-Pr | CSOMe | $CF_3$ | |
| 3-273 | c-Pr | CSOMe | $CF_3$ | |
| 3-274 | n-Bu | CSOMe | $CF_3$ | |
| 3-275 | n-Pen | CSOMe | $CF_3$ | |
| 3-276 | $CH_2CF_3$ | CSOMe | $CF_3$ | |
| 3-277 | $CH_2C_2F_5$ | CSOMe | $CF_3$ | |
| 3-278 | $CH_2CHF_2$ | CSOMe | $CF_3$ | |
| 3-279 | $CH_2CF_2CHF_2$ | CSOMe | $CF_3$ | |
| 3-280 | $CH_2SCH_3$ | CSOMe | $CF_3$ | |
| 3-281 | $CH_2SOCH_3$ | CSOMe | $CF_3$ | |
| 3-282 | $CH_2SO_2CH_3$ | CSOMe | $CF_3$ | |
| 3-283 | $CH_2SCH_2CH_3$ | CSOMe | $CF_3$ | |
| 3-284 | $CH_2SOCH_2CH_3$ | CSOMe | $CF_3$ | |
| 3-285 | $CH_2SO_2CH_2CH_3$ | CSOMe | $CF_3$ | |
| 3-286 | $CH_2CH_2SCH_3$ | CSOMe | $CF_3$ | |
| 3-287 | $CH_2CH_2SOCH_3$ | CSOMe | $CF_3$ | |
| 3-288 | $CH_2CH_2SO_2CH_3$ | CSOMe | $CF_3$ | |
| 3-289 | $CH_2CH_2SCH_2CH_3$ | CSOMe | $CF_3$ | |
| 3-290 | $CH_2CH_2SOCH_2CH_3$ | CSOMe | $CF_3$ | |
| 3-291 | $CH_2CH_2SO_2CH_2CH_3$ | CSOMe | $CF_3$ | |
| 3-292 | $CH_2CH_2SCF_3$ | CSOMe | $CF_3$ | |
| 3-293 | $CH_2CH_2SOCF_3$ | CSOMe | $CF_3$ | |
| 3-294 | $CH_2CH_2SO_2CF_3$ | CSOMe | $CF_3$ | |
| 3-295 | $CH_2Ph$ | CSOMe | $CF_3$ | |
| 3-296 | $CH_2C{\equiv}CH$ | CSOMe | $CF_3$ | |
| 3-297 | $CH_2C{\equiv}CCH_3$ | CSOMe | $CF_3$ | |
| 3-298 | $CH_2C{\equiv}N$ | CSOMe | $CF_3$ | |
| 3-299 | $CH_2CH{=}CH_2$ | CSOMe | $CF_3$ | |
| 3-300 | $CH_2CH{=}CHCH_3$ | CSOMe | $CF_3$ | |
| 3-301 | $CH_2CH{=}C(CH_3)_3$ | CSOMe | $CF_3$ | |
| 3-302 | $CH_2OCH_3$ | CSOMe | $CF_3$ | |
| 3-303 | $CH_2CH_2OCH_3$ | CSOMe | $CF_3$ | |
| 3-304 | $CH_2OCH_2CH_3$ | CSOMe | $CF_3$ | |
| 3-305 | $CH_2CH_2OCH_2CH_3$ | CSOMe | $CF_3$ | |
| 3-306 | H | CSOEt | $CF_3$ | 130-131 |
| 3-307 | Me | CSOEt | $CF_3$ | |
| 3-308 | Et | CSOEt | $CF_3$ | |
| 3-309 | n-Pr | CSOEt | $CF_3$ | |
| 3-310 | i-Pr | CSOEt | $CF_3$ | |
| 3-311 | c-Pr | CSOEt | $CF_3$ | |
| 3-312 | n-Bu | CSOEt | $CF_3$ | |

TABLE 3-continued

| Compound No. | R³ | R⁴ | R⁵ | Physical property |
|---|---|---|---|---|
| 3-313 | n-Pen | CSOEt | CF₃ | |
| 3-314 | CH₂CF₃ | CSOEt | CF₃ | |
| 3-315 | CH₂C₂F₅ | CSOEt | CF₃ | |
| 3-316 | CH₂CHF₂ | CSOEt | CF₃ | |
| 3-317 | CH₂CF₂CHF₂ | CSOEt | CF₃ | |
| 3-318 | CH₂SCH₃ | CSOEt | CF₃ | |
| 3-319 | CH₂SOCH₃ | CSOEt | CF₃ | |
| 3-320 | CH₂SO₂CH₃ | CSOEt | CF₃ | |
| 3-321 | CH₂SCH₂CH₃ | CSOEt | CF₃ | |
| 3-322 | CH₂SOCH₂CH₃ | CSOEt | CF₃ | |
| 3-323 | CH₂SO₂CH₂CH₃ | CSOEt | CF₃ | |
| 3-324 | CH₂CH₂SCH₃ | CSOEt | CF₃ | |
| 3-325 | CH₂CH₂SOCH₃ | CSOEt | CF₃ | |
| 3-326 | CH₂CH₂SO₂CH₃ | CSOEt | CF₃ | |
| 3-327 | CH₂CH₂SCH₂CH₃ | CSOEt | CF₃ | |
| 3-328 | CH₂CH₂SOCH₂CH₃ | CSOEt | CF₃ | |
| 3-329 | CH₂CH₂SO₂CH₂CH₃ | CSOEt | CF₃ | |
| 3-330 | CH₂CH₂SCF₃ | CSOEt | CF₃ | |
| 3-331 | CH₂CH₂SOCF₃ | CSOEt | CF₃ | |
| 3-332 | CH₂CH₂SO₂CF₃ | CSOEt | CF₃ | |
| 3-333 | CH₂Ph | CSOEt | CF₃ | |
| 3-334 | CH₂C≡CH | CSOEt | CF₃ | |
| 3-335 | CH₂C≡CCH₃ | CSOEt | CF₃ | |
| 3-336 | CH₂C≡N | CSOEt | CF₃ | |
| 3-337 | CH₂CH=CH₂ | CSOEt | CF₃ | |
| 3-338 | CH₂CH=CHCH₃ | CSOEt | CF₃ | |
| 3-339 | CH₂CH=C(CH₃)₃ | CSOEt | CF₃ | |
| 3-340 | CH₂OCH₃ | CSOEt | CF₃ | |
| 3-341 | CH₂CH₂OCH₃ | CSOEt | CF₃ | |
| 3-342 | CH₂OCH₂CH₃ | CSOEt | CF₃ | |
| 3-343 | CH₂CH₂OCH₂CH₃ | CSOEt | CF₃ | |
| 3-344 | H | CSN(Me)₂ | CF₃ | |
| 3-345 | Me | CSN(Me)₂ | CF₃ | |
| 3-346 | Et | CSN(Me)₂ | CF₃ | |
| 3-347 | n-Pr | CSN(Me)₂ | CF₃ | |
| 3-348 | i-Pr | CSN(Me)₂ | CF₃ | |
| 3-349 | c-Pr | CSN(Me)₂ | CF₃ | |
| 3-350 | n-Bu | CSN(Me)₂ | CF₃ | |
| 3-351 | n-Pen | CSN(Me)₂ | CF₃ | |
| 3-352 | CH₂CF₃ | CSN(Me)₂ | CF₃ | |
| 3-353 | CH₂C₂F₅ | CSN(Me)₂ | CF₃ | |
| 3-354 | CH₂CHF₂ | CSN(Me)₂ | CF₃ | |
| 3-355 | CH₂CF₂CHF₂ | CSN(Me)₂ | CF₃ | |
| 3-356 | CH₂SCH₃ | CSN(Me)₂ | CF₃ | |
| 3-357 | CH₂SOCH₃ | CSN(Me)₂ | CF₃ | |
| 3-358 | CH₂SO₂CH₃ | CSN(Me)₂ | CF₃ | |
| 3-359 | CH₂SCH₂CH₃ | CSN(Me)₂ | CF₃ | |
| 3-360 | CH₂SOCH₂CH₃ | CSN(Me)₂ | CF₃ | |
| 3-361 | CH₂SO₂CH₂CH₃ | CSN(Me)₂ | CF₃ | |
| 3-362 | CH₂CH₂SCH₃ | CSN(Me)₂ | CF₃ | |
| 3-363 | CH₂CH₂SOCH₃ | CSN(Me)₂ | CF₃ | |
| 3-364 | CH₂CH₂SO₂CH₃ | CSN(Me)₂ | CF₃ | |
| 3-365 | CH₂CH₂SCH₂CH₃ | CSN(Me)₂ | CF₃ | |
| 3-366 | CH₂CH₂SOCH₂CH₃ | CSN(Me)₂ | CF₃ | |
| 3-367 | CH₂CH₂SO₂CH₂CH₃ | CSN(Me)₂ | CF₃ | |
| 3-368 | CH₂CH₂SCF₃ | CSN(Me)₂ | CF₃ | |
| 3-369 | CH₂CH₂SOCF₃ | CSN(Me)₂ | CF₃ | |
| 3-370 | CH₂CH₂SO₂CF₃ | CSN(Me)₂ | CF₃ | |
| 3-371 | CH₂Ph | CSN(Me)₂ | CF₃ | |
| 3-372 | CH₂C≡CH | CSN(Me)₂ | CF₃ | |
| 3-373 | CH₂C≡CCH₃ | CSN(Me)₂ | CF₃ | |
| 3-374 | CH₂C≡N | CSN(Me)₂ | CF₃ | |
| 3-375 | CH₂CH=CH₂ | CSN(Me)₂ | CF₃ | |
| 3-376 | CH₂CH=CHCH₃ | CSN(Me)₂ | CF₃ | |
| 3-377 | CH₂CH=C(CH₃)₃ | CSN(Me)₂ | CF₃ | |
| 3-378 | CH₂OCH₃ | CSN(Me)₂ | CF₃ | |
| 3-379 | CH₂CH₂OCH₃ | CSN(Me)₂ | CF₃ | |
| 3-380 | CH₂OCH₂CH₃ | CSN(Me)₂ | CF₃ | |
| 3-381 | CH₂CH₂OCH₂CH₃ | CSN(Me)₂ | CF₃ | |
| 3-382 | H | CSNHEt | CF₃ | |
| 3-383 | Me | CSNHEt | CF₃ | |
| 3-384 | Et | CSNHEt | CF₃ | |
| 3-385 | n-Pr | CSNHEt | CF₃ | |
| 3-386 | i-Pr | CSNHEt | CF₃ | |
| 3-387 | c-Pr | CSNHEt | CF₃ | |
| 3-388 | n-Bu | CSNHEt | CF₃ | |
| 3-389 | n-Pen | CSNHEt | CF₃ | |
| 3-390 | CH₂CF₃ | CSNHEt | CF₃ | |
| 3-391 | CH₂C₂F₅ | CSNHEt | CF₃ | |
| 3-392 | CH₂CHF₂ | CSNHEt | CF₃ | |
| 3-393 | CH₂CF₂CHF₂ | CSNHEt | CF₃ | |
| 3-394 | CH₂SCH₃ | CSNHEt | CF₃ | |
| 3-395 | CH₂SOCH₃ | CSNHEt | CF₃ | |
| 3-396 | CH₂SO₂CH₃ | CSNHEt | CF₃ | |
| 3-397 | CH₂SCH₂CH₃ | CSNHEt | CF₃ | |
| 3-398 | CH₂SOCH₂CH₃ | CSNHEt | CF₃ | |
| 3-399 | CH₂SO₂CH₂CH₃ | CSNHEt | CF₃ | |
| 3-400 | CH₂CH₂SCH₃ | CSNHEt | CF₃ | |
| 3-401 | CH₂CH₂SOCH₃ | CSNHEt | CF₃ | |
| 3-402 | CH₂CH₂SO₂CH₃ | CSNHEt | CF₃ | |
| 3-403 | CH₂CH₂SCH₂CH₃ | CSNHEt | CF₃ | |
| 3-404 | CH₂CH₂SOCH₂CH₃ | CSNHEt | CF₃ | |
| 3-405 | CH₂CH₂SO₂CH₂CH₃ | CSNHEt | CF₃ | |
| 3-406 | CH₂CH₂SCF₃ | CSNHEt | CF₃ | |
| 3-407 | CH₂CH₂SOCF₃ | CSNHEt | CF₃ | |
| 3-408 | CH₂CH₂SO₂CF₃ | CSNHEt | CF₃ | |
| 3-409 | CH₂Ph | CSNHEt | CF₃ | |
| 3-410 | CH₂C≡CH | CSNHEt | CF₃ | |
| 3-411 | CH₂C≡CCH₃ | CSNHEt | CF₃ | |
| 3-412 | CH₂C≡N | CSNHEt | CF₃ | |
| 3-413 | CH₂CH=CH₂ | CSNHEt | CF₃ | |
| 3-414 | CH₂CH=CHCH₃ | CSNHEt | CF₃ | |
| 3-415 | CH₂CH=C(CH₃)₃ | CSNHEt | CF₃ | |
| 3-416 | CH₂OCH₃ | CSNHEt | CF₃ | |
| 3-417 | CH₂CH₂OCH₃ | CSNHEt | CF₃ | |
| 3-418 | CH₂OCH₂CH₃ | CSNHEt | CF₃ | |
| 3-419 | CH₂CH₂OCH₂CH₃ | CSNHEt | CF₃ | |
| 3-420 | H | SO₂Me | CF₃ | |
| 3-421 | Me | SO₂Me | CF₃ | |
| 3-422 | Et | SO₂Me | CF₃ | |
| 3-423 | n-Pr | SO₂Me | CF₃ | |
| 3-424 | i-Pr | SO₂Me | CF₃ | |
| 3-425 | c-Pr | SO₂Me | CF₃ | |
| 3-426 | n-Bu | SO₂Me | CF₃ | |
| 3-427 | n-Pen | SO₂Me | CF₃ | |
| 3-428 | CH₂CF₃ | SO₂Me | CF₃ | |
| 3-429 | CH₂C₂F₅ | SO₂Me | CF₃ | |
| 3-430 | CH₂CHF₂ | SO₂Me | CF₃ | |
| 3-431 | CH₂CF₂CHF₂ | SO₂Me | CF₃ | |
| 3-432 | CH₂SCH₃ | SO₂Me | CF₃ | |
| 3-433 | CH₂SOCH₃ | SO₂Me | CF₃ | |
| 3-434 | CH₂SO₂CH₃ | SO₂Me | CF₃ | |
| 3-435 | CH₂SCH₂CH₃ | SO₂Me | CF₃ | |
| 3-436 | CH₂SOCH₂CH₃ | SO₂Me | CF₃ | |
| 3-437 | CH₂SO₂CH₂CH₃ | SO₂Me | CF₃ | |
| 3-438 | CH₂CH₂SCH₃ | SO₂Me | CF₃ | |
| 3-439 | CH₂CH₂SOCH₃ | SO₂Me | CF₃ | |
| 3-440 | CH₂CH₂SO₂CH₃ | SO₂Me | CF₃ | |
| 3-441 | CH₂CH₂SCH₂CH₃ | SO₂Me | CF₃ | |
| 3-442 | CH₂CH₂SOCH₂CH₃ | SO₂Me | CF₃ | |
| 3-443 | CH₂CH₂SO₂CH₂CH₃ | SO₂Me | CF₃ | |
| 3-444 | CH₂CH₂SCF₃ | SO₂Me | CF₃ | |
| 3-445 | CH₂CH₂SOCF₃ | SO₂Me | CF₃ | |
| 3-446 | CH₂CH₂SO₂CF₃ | SO₂Me | CF₃ | |
| 3-447 | CH₂Ph | SO₂Me | CF₃ | |
| 3-448 | CH₂C≡CH | SO₂Me | CF₃ | |
| 3-449 | CH₂C≡CCH₃ | SO₂Me | CF₃ | |
| 3-450 | CH₂C≡N | SO₂Me | CF₃ | |
| 3-451 | CH₂CH=CH₂ | SO₂Me | CF₃ | |
| 3-452 | CH₂CH=CHCH₃ | SO₂Me | CF₃ | |
| 3-453 | CH₂CH=C(CH₃)₃ | SO₂Me | CF₃ | |
| 3-454 | CH₂OCH₃ | SO₂Me | CF₃ | |
| 3-455 | CH₂CH₂OCH₃ | SO₂Me | CF₃ | |
| 3-456 | CH₂OCH₂CH₃ | SO₂Me | CF₃ | |
| 3-457 | CH₂CH₂OCH₂CH₃ | SO₂Me | CF₃ | |

[Chem. 13]

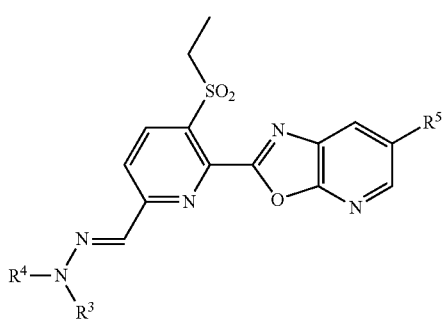

(1B-2)

TABLE 4

| Compound No. | R³ | R⁴ | R⁵ | Physical property |
|---|---|---|---|---|
| 4-1 | H | H | $SCF_3$ | 182-183 |
| 4-2 | Me | H | $SCF_3$ | |
| 4-3 | Et | H | $SCF_3$ | |
| 4-4 | n-Pr | H | $SCF_3$ | |
| 4-5 | i-Pr | H | $SCF_3$ | |
| 4-6 | c-Pr | H | $SCF_3$ | |
| 4-7 | n-Bu | H | $SCF_3$ | |
| 4-8 | n-Pen | H | $SCF_3$ | |
| 4-9 | $CH_2CF_3$ | H | $SCF_3$ | 175-176 |
| 4-10 | $CH_2C_2F_5$ | H | $SCF_3$ | |
| 4-11 | $CH_2CHF_2$ | H | $SCF_3$ | |
| 4-12 | $CH_2CF_2CHF_2$ | H | $SCF_3$ | |
| 4-13 | $CH_2SCH_3$ | H | $SCF_3$ | |
| 4-14 | $CH_2SOCH_3$ | H | $SCF_3$ | |
| 4-15 | $CH_2SO_2CH_3$ | H | $SCF_3$ | |
| 4-16 | $CH_2SCH_2CH_3$ | H | $SCF_3$ | |
| 4-17 | $CH_2SOCH_2CH_3$ | H | $SCF_3$ | |
| 4-18 | $CH_2SO_2CH_2CH_3$ | H | $SCF_3$ | |
| 4-19 | $CH_2CH_2SCH_3$ | H | $SCF_3$ | |
| 4-20 | $CH_2CH_2SOCH_3$ | H | $SCF_3$ | |
| 4-21 | $CH_2CH_2SO_2CH_3$ | H | $SCF_3$ | |
| 4-22 | $CH_2CH_2SCH_2CH_3$ | H | $SCF_3$ | |
| 4-23 | $CH_2CH_2SOCH_2CH_3$ | H | $SCF_3$ | |
| 4-24 | $CH_2CH_2SO_2CH_2CH_3$ | H | $SCF_3$ | |
| 4-25 | $CH_2CH_2SCF_3$ | H | $SCF_3$ | |
| 4-26 | $CH_2CH_2SOCF_3$ | H | $SCF_3$ | |
| 4-27 | $CH_2CH_2SO_2CF_3$ | H | $SCF_3$ | |
| 4-28 | $CH_2Ph$ | H | $SCF_3$ | |
| 4-29 | $CH_2C{\equiv}CH$ | H | $SCF_3$ | |
| 4-30 | $CH_2C{\equiv}CCH_3$ | H | $SCF_3$ | |
| 4-31 | $CH_2C{\equiv}N$ | H | $SCF_3$ | |
| 4-32 | $CH_2CH{=}CH_2$ | H | $SCF_3$ | |
| 4-33 | $CH_2CH{=}CHCH_3$ | H | $SCF_3$ | |
| 4-34 | $CH_2CH{=}C(CH_3)_3$ | H | $SCF_3$ | |
| 4-35 | $CH_2OCH_3$ | H | $SCF_3$ | |
| 4-36 | $CH_2CH_2OCH_3$ | H | $SCF_3$ | |
| 4-37 | $CH_2OCH_2CH_3$ | H | $SCF_3$ | |
| 4-38 | $CH_2CH_2OCH_2CH_3$ | H | $SCF_3$ | |
| 4-39 | Ph | H | $SCF_3$ | |
| 4-40 | 4-SMePh | H | $SCF_3$ | |
| 4-41 | $4\text{-}CF_3Ph$ | H | $SCF_3$ | |
| 4-42 | 2-F,4-Cl—Ph | H | $SCF_3$ | |
| 4-43 | Me | Me | $SCF_3$ | |
| 4-44 | Et | Me | $SCF_3$ | |
| 4-45 | n-Pr | Me | $SCF_3$ | |
| 4-46 | i-Pr | Me | $SCF_3$ | |
| 4-47 | c-Pr | Me | $SCF_3$ | |
| 4-48 | n-Bu | Me | $SCF_3$ | |
| 4-49 | n-Pen | Me | $SCF_3$ | |
| 4-50 | $CH_2CF_3$ | Me | $SCF_3$ | |
| 4-51 | $CH_2C_2F_5$ | Me | $SCF_3$ | |
| 4-52 | $CH_2CHF_2$ | Me | $SCF_3$ | |
| 4-53 | $CH_2CF_2CHF_2$ | Me | $SCF_3$ | |
| 4-54 | $CH_2SCH_3$ | Me | $SCF_3$ | |
| 4-55 | $CH_2SOCH_3$ | Me | $SCF_3$ | |
| 4-56 | $CH_2SO_2CH_3$ | Me | $SCF_3$ | |
| 4-57 | $CH_2SCH_2CH_3$ | Me | $SCF_3$ | |
| 4-58 | $CH_2SOCH_2CH_3$ | Me | $SCF_3$ | |
| 4-59 | $CH_2SO_2CH_2CH_3$ | Me | $SCF_3$ | |
| 4-60 | $CH_2CH_2SCH_3$ | Me | $SCF_3$ | |
| 4-61 | $CH_2CH_2SOCH_3$ | Me | $SCF_3$ | |
| 4-62 | $CH_2CH_2SO_2CH_3$ | Me | $SCF_3$ | |
| 4-63 | $CH_2CH_2SCH_2CH_3$ | Me | $SCF_3$ | |
| 4-64 | $CH_2CH_2SOCH_2CH_3$ | Me | $SCF_3$ | |
| 4-65 | $CH_2CH_2SO_2CH_2CH_3$ | Me | $SCF_3$ | |
| 4-66 | $CH_2CH_2SCF_3$ | Me | $SCF_3$ | |
| 4-67 | $CH_2CH_2SOCF_3$ | Me | $SCF_3$ | |
| 4-68 | $CH_2CH_2SO_2CF_3$ | Me | $SCF_3$ | |
| 4-69 | $CH_2Ph$ | Me | $SCF_3$ | |
| 4-70 | $CH_2C{\equiv}CH$ | Me | $SCF_3$ | |
| 4-71 | $CH_2C{\equiv}CCH_3$ | Me | $SCF_3$ | |
| 4-72 | $CH_2C{\equiv}N$ | Me | $SCF_3$ | |
| 4-73 | $CH_2CH{=}CH_2$ | Me | $SCF_3$ | |
| 4-74 | $CH_2CH{=}CHCH_3$ | Me | $SCF_3$ | |
| 4-75 | $CH_2CH{=}C(CH_3)_3$ | Me | $SCF_3$ | |
| 4-76 | $CH_2OCH_3$ | Me | $SCF_3$ | |
| 4-77 | $CH_2CH_2OCH_3$ | Me | $SCF_3$ | |
| 4-78 | $CH_2OCH_2CH_3$ | Me | $SCF_3$ | |
| 4-79 | $CH_2CH_2OCH_2CH_3$ | Me | $SCF_3$ | |
| 4-80 | Et | Et | $SCF_3$ | |
| 4-81 | n-Pr | Et | $SCF_3$ | |
| 4-82 | i-Pr | Et | $SCF_3$ | |
| 4-83 | c-Pr | Et | $SCF_3$ | |
| 4-84 | n-Bu | Et | $SCF_3$ | |
| 4-85 | n-Pen | Et | $SCF_3$ | |
| 4-86 | $CH_2CF_3$ | Et | $SCF_3$ | |
| 4-87 | $CH_2C_2F_5$ | Et | $SCF_3$ | |
| 4-88 | $CH_2CHF_2$ | Et | $SCF_3$ | |
| 4-89 | $CH_2CF_2CHF_2$ | Et | $SCF_3$ | |
| 4-90 | $CH_2SCH_3$ | Et | $SCF_3$ | |
| 4-91 | $CH_2SOCH_3$ | Et | $SCF_3$ | |
| 4-92 | $CH_2SO_2CH_3$ | Et | $SCF_3$ | |
| 4-93 | $CH_2SCH_2CH_3$ | Et | $SCF_3$ | |
| 4-94 | $CH_2SOCH_2CH_3$ | Et | $SCF_3$ | |
| 4-95 | $CH_2SO_2CH_2CH_3$ | Et | $SCF_3$ | |
| 4-96 | $CH_2CH_2SCH_3$ | Et | $SCF_3$ | |
| 4-97 | $CH_2CH_2SOCH_3$ | Et | $SCF_3$ | |
| 4-98 | $CH_2CH_2SO_2CH_3$ | Et | $SCF_3$ | |
| 4-99 | $CH_2CH_2SCH_2CH_3$ | Et | $SCF_3$ | |
| 4-100 | $CH_2CH_2SOCH_2CH_3$ | Et | $SCF_3$ | |
| 4-101 | $CH_2CH_2SO_2CH_2CH_3$ | Et | $SCF_3$ | |
| 4-102 | $CH_2CH_2SCF_3$ | Et | $SCF_3$ | |
| 4-103 | $CH_2CH_2SOCF_3$ | Et | $SCF_3$ | |
| 4-104 | $CH_2CH_2SO_2CF_3$ | Et | $SCF_3$ | |
| 4-105 | $CH_2Ph$ | Et | $SCF_3$ | |
| 4-106 | $CH_2C{\equiv}CH$ | Et | $SCF_3$ | |
| 4-107 | $CH_2C{\equiv}CCH_3$ | Et | $SCF_3$ | |
| 4-108 | $CH_2C{\equiv}N$ | Et | $SCF_3$ | |
| 4-109 | $CH_2CH{=}CH_2$ | Et | $SCF_3$ | |
| 4-110 | $CH_2CH{=}CHCH_3$ | Et | $SCF_3$ | |
| 4-111 | $CH_2CH{=}C(CH_3)_3$ | Et | $SCF_3$ | |
| 4-112 | $CH_2OCH_3$ | Et | $SCF_3$ | |
| 4-113 | $CH_2CH_2OCH_3$ | Et | $SCF_3$ | |
| 4-114 | $CH_2OCH_2CH_3$ | Et | $SCF_3$ | |
| 4-115 | $CH_2CH_2OCH_2CH_3$ | Et | $SCF_3$ | |
| 4-116 | H | Ac | $SCF_3$ | |
| 4-117 | Me | Ac | $SCF_3$ | |
| 4-118 | Et | Ac | $SCF_3$ | |
| 4-119 | n-Pr | Ac | $SCF_3$ | |
| 4-120 | i-Pr | Ac | $SCF_3$ | |
| 4-121 | c-Pr | Ac | $SCF_3$ | |
| 4-122 | n-Bu | Ac | $SCF_3$ | |
| 4-123 | n-Pen | Ac | $SCF_3$ | |
| 4-124 | $CH_2CF_3$ | Ac | $SCF_3$ | |
| 4-125 | $CH_2C_2F_5$ | Ac | $SCF_3$ | |
| 4-126 | $CH_2CHF_2$ | Ac | $SCF_3$ | |
| 4-127 | $CH_2CF_2CHF_2$ | Ac | $SCF_3$ | |
| 4-128 | $CH_2SCH_3$ | Ac | $SCF_3$ | |
| 4-129 | $CH_2SOCH_3$ | Ac | $SCF_3$ | |
| 4-130 | $CH_2SO_2CH_3$ | Ac | $SCF_3$ | |
| 4-131 | $CH_2SCH_2CH_3$ | Ac | $SCF_3$ | |
| 4-132 | $CH_2SOCH_2CH_3$ | Ac | $SCF_3$ | |

TABLE 4-continued

| Compound No. | R³ | R⁴ | R⁵ | Physical property |
|---|---|---|---|---|
| 4-133 | CH₂SO₂CH₂CH₃ | Ac | SCF₃ | |
| 4-134 | CH₂CH₂SCH₃ | Ac | SCF₃ | |
| 4-135 | CH₂CH₂SOCH₃ | Ac | SCF₃ | |
| 4-136 | CH₂CH₂SO₂CH₃ | Ac | SCF₃ | |
| 4-137 | CH₂CH₂SCH₂CH₃ | Ac | SCF₃ | |
| 4-138 | CH₂CH₂SOCH₂CH₃ | Ac | SCF₃ | |
| 4-139 | CH₂CH₂SO₂CH₂CH₃ | Ac | SCF₃ | |
| 4-140 | CH₂CH₂SCF₃ | Ac | SCF₃ | |
| 4-141 | CH₂CH₂SOCF₃ | Ac | SCF₃ | |
| 4-142 | CH₂CH₂SO₂CF₃ | Ac | SCF₃ | |
| 4-143 | CH₂Ph | Ac | SCF₃ | |
| 4-144 | CH₂C≡CH | Ac | SCF₃ | |
| 4-145 | CH₂C≡CCH₃ | Ac | SCF₃ | |
| 4-146 | CH₂C≡N | Ac | SCF₃ | |
| 4-147 | CH₂CH=CH₂ | Ac | SCF₃ | |
| 4-148 | CH₂CH=CHCH₃ | Ac | SCF₃ | |
| 4-149 | CH₂CH=C(CH₃)₃ | Ac | SCF₃ | |
| 4-150 | CH₂OCH₃ | Ac | SCF₃ | |
| 4-151 | CH₂CH₂OCH₃ | Ac | SCF₃ | |
| 4-152 | CH₂OCH₂CH₃ | Ac | SCF₃ | |
| 4-153 | CH₂CH₂OCH₂CH₃ | Ac | SCF₃ | |
| 4-154 | H | CO₂Me | SCF₃ | |
| 4-155 | Me | CO₂Me | SCF₃ | |
| 4-156 | Et | CO₂Me | SCF₃ | |
| 4-157 | n-Pr | CO₂Me | SCF₃ | |
| 4-158 | i-Pr | CO₂Me | SCF₃ | |
| 4-159 | c-Pr | CO₂Me | SCF₃ | |
| 4-160 | n-Bu | CO₂Me | SCF₃ | |
| 4-161 | n-Pen | CO₂Me | SCF₃ | |
| 4-162 | CH₂CF₃ | CO₂Me | SCF₃ | |
| 4-163 | CH₂C₂F₅ | CO₂Me | SCF₃ | |
| 4-164 | CH₂CHF₂ | CO₂Me | SCF₃ | |
| 4-165 | CH₂CF₂CHF₂ | CO₂Me | SCF₃ | |
| 4-166 | CH₂SCH₃ | CO₂Me | SCF₃ | |
| 4-167 | CH₂SOCH₃ | CO₂Me | SCF₃ | |
| 4-168 | CH₂SO₂CH₃ | CO₂Me | SCF₃ | |
| 4-169 | CH₂SCH₂CH₃ | CO₂Me | SCF₃ | |
| 4-170 | CH₂SOCH₂CH₃ | CO₂Me | SCF₃ | |
| 4-171 | CH₂SO₂CH₂CH₃ | CO₂Me | SCF₃ | |
| 4-172 | CH₂CH₂SCH₃ | CO₂Me | SCF₃ | |
| 4-173 | CH₂CH₂SOCH₃ | CO₂Me | SCF₃ | |
| 4-174 | CH₂CH₂SO₂CH₃ | CO₂Me | SCF₃ | |
| 4-175 | CH₂CH₂SCH₂CH₃ | CO₂Me | SCF₃ | |
| 4-176 | CH₂CH₂SOCH₂CH₃ | CO₂Me | SCF₃ | |
| 4-177 | CH₂CH₂SO₂CH₂CH₃ | CO₂Me | SCF₃ | |
| 4-178 | CH₂CH₂SCF₃ | CO₂Me | SCF₃ | |
| 4-179 | CH₂CH₂SOCF₃ | CO₂Me | SCF₃ | |
| 4-180 | CH₂CH₂SO₂CF₃ | CO₂Me | SCF₃ | |
| 4-181 | CH₂Ph | CO₂Me | SCF₃ | |
| 4-182 | CH₂C≡CH | CO₂Me | SCF₃ | |
| 4-183 | CH₂C≡CCH₃ | CO₂Me | SCF₃ | |
| 4-184 | CH₂C≡N | CO₂Me | SCF₃ | |
| 4-185 | CH₂CH=CH₂ | CO₂Me | SCF₃ | |
| 4-186 | CH₂CH=CHCH₃ | CO₂Me | SCF₃ | |
| 4-187 | CH₂CH=C(CH₃)₃ | CO₂Me | SCF₃ | |
| 4-188 | CH₂OCH₃ | CO₂Me | SCF₃ | |
| 4-189 | CH₂CH₂OCH₃ | CO₂Me | SCF₃ | |
| 4-190 | CH₂OCH₂CH₃ | CO₂Me | SCF₃ | |
| 4-191 | CH₂CH₂OCH₂CH₃ | CO₂Me | SCF₃ | |
| 4-192 | H | CO₂Et | SCF₃ | |
| 4-193 | Me | CO₂Et | SCF₃ | |
| 4-194 | Et | CO₂Et | SCF₃ | |
| 4-195 | n-Pr | CO₂Et | SCF₃ | |
| 4-196 | i-Pr | CO₂Et | SCF₃ | |
| 4-197 | c-Pr | CO₂Et | SCF₃ | |
| 4-198 | n-Bu | CO₂Et | SCF₃ | |
| 4-199 | n-Pen | CO₂Et | SCF₃ | |
| 4-200 | CH₂CF₃ | CO₂Et | SCF₃ | |
| 4-201 | CH₂C₂F₅ | CO₂Et | SCF₃ | |
| 4-202 | CH₂CHF₂ | CO₂Et | SCF₃ | |
| 4-203 | CH₂CF₂CHF₂ | CO₂Et | SCF₃ | |
| 4-204 | CH₂SCH₃ | CO₂Et | SCF₃ | |
| 4-205 | CH₂SOCH₃ | CO₂Et | SCF₃ | |
| 4-206 | CH₂SO₂CH₃ | CO₂Et | SCF₃ | |
| 4-207 | CH₂SCH₂CH₃ | CO₂Et | SCF₃ | |
| 4-208 | CH₂SOCH₂CH₃ | CO₂Et | SCF₃ | |
| 4-209 | CH₂SO₂CH₂CH₃ | CO₂Et | SCF₃ | |
| 4-210 | CH₂CH₂SCH₃ | CO₂Et | SCF₃ | |
| 4-211 | CH₂CH₂SOCH₃ | CO₂Et | SCF₃ | |
| 4-212 | CH₂CH₂SO₂CH₃ | CO₂Et | SCF₃ | |
| 4-213 | CH₂CH₂SCH₂CH₃ | CO₂Et | SCF₃ | |
| 4-214 | CH₂CH₂SOCH₂CH₃ | CO₂Et | SCF₃ | |
| 4-215 | CH₂CH₂SO₂CH₂CH₃ | CO₂Et | SCF₃ | |
| 4-216 | CH₂CH₂SCF₃ | CO₂Et | SCF₃ | |
| 4-217 | CH₂CH₂SOCF₃ | CO₂Et | SCF₃ | |
| 4-218 | CH₂CH₂SO₂CF₃ | CO₂Et | SCF₃ | |
| 4-219 | CH₂Ph | CO₂Et | SCF₃ | |
| 4-220 | CH₂C≡CH | CO₂Et | SCF₃ | |
| 4-221 | CH₂C≡CCH₃ | CO₂Et | SCF₃ | |
| 4-222 | CH₂C≡N | CO₂Et | SCF₃ | |
| 4-223 | CH₂CH=CH₂ | CO₂Et | SCF₃ | |
| 4-224 | CH₂CH=CHCH₃ | CO₂Et | SCF₃ | |
| 4-225 | CH₂CH=C(CH₃)₃ | CO₂Et | SCF₃ | |
| 4-226 | CH₂OCH₃ | CO₂Et | SCF₃ | |
| 4-227 | CH₂CH₂OCH₃ | CO₂Et | SCF₃ | |
| 4-228 | CH₂OCH₂CH₃ | CO₂Et | SCF₃ | |
| 4-229 | CH₂CH₂OCH₂CH₃ | CO₂Et | SCF₃ | |
| 4-230 | H | COCF₃ | SCF₃ | |
| 4-231 | Me | COCF₃ | SCF₃ | |
| 4-232 | Et | COCF₃ | SCF₃ | |
| 4-233 | n-Pr | COCF₃ | SCF₃ | |
| 4-234 | i-Pr | COCF₃ | SCF₃ | |
| 4-235 | c-Pr | COCF₃ | SCF₃ | |
| 4-236 | n-Bu | COCF₃ | SCF₃ | |
| 4-237 | n-Pen | COCF₃ | SCF₃ | |
| 4-238 | CH₂CF₃ | COCF₃ | SCF₃ | |
| 4-239 | CH₂C₂F₅ | COCF₃ | SCF₃ | |
| 4-240 | CH₂CHF₂ | COCF₃ | SCF₃ | |
| 4-241 | CH₂CF₂CHF₂ | COCF₃ | SCF₃ | |
| 4-242 | CH₂SCH₃ | COCF₃ | SCF₃ | |
| 4-243 | CH₂SOCH₃ | COCF₃ | SCF₃ | |
| 4-244 | CH₂SO₂CH₃ | COCF₃ | SCF₃ | |
| 4-245 | CH₂SCH₂CH₃ | COCF₃ | SCF₃ | |
| 4-246 | CH₂SOCH₂CH₃ | COCF₃ | SCF₃ | |
| 4-247 | CH₂SO₂CH₂CH₃ | COCF₃ | SCF₃ | |
| 4-248 | CH₂CH₂SCH₃ | COCF₃ | SCF₃ | |
| 4-249 | CH₂CH₂SOCH₃ | COCF₃ | SCF₃ | |
| 4-250 | CH₂CH₂SO₂CH₃ | COCF₃ | SCF₃ | |
| 4-251 | CH₂CH₂SCH₂CH₃ | COCF₃ | SCF₃ | |
| 4-252 | CH₂CH₂SOCH₂CH₃ | COCF₃ | SCF₃ | |
| 4-253 | CH₂CH₂SO₂CH₂CH₃ | COCF₃ | SCF₃ | |
| 4-254 | CH₂CH₂SCF₃ | COCF₃ | SCF₃ | |
| 4-255 | CH₂CH₂SOCF₃ | COCF₃ | SCF₃ | |
| 4-256 | CH₂CH₂SO₂CF₃ | COCF₃ | SCF₃ | |
| 4-257 | CH₂Ph | COCF₃ | SCF₃ | |
| 4-258 | CH₂C≡CH | COCF₃ | SCF₃ | |
| 4-259 | CH₂C≡CCH₃ | COCF₃ | SCF₃ | |
| 4-260 | CH₂C≡N | COCF₃ | SCF₃ | |
| 4-261 | CH₂CH=CH₂ | COCF₃ | SCF₃ | |
| 4-262 | CH₂CH=CHCH₃ | COCF₃ | SCF₃ | |
| 4-263 | CH₂CH=C(CH₃)₃ | COCF₃ | SCF₃ | |
| 4-264 | CH₂OCH₃ | COCF₃ | SCF₃ | |
| 4-265 | CH₂CH₂OCH₃ | COCF₃ | SCF₃ | |
| 4-266 | CH₂OCH₂CH₃ | COCF₃ | SCF₃ | |
| 4-267 | CH₂CH₂OCH₂CH₃ | COCF₃ | SCF₃ | |
| 4-268 | H | CSOMe | SCF₃ | |
| 4-269 | Me | CSOMe | SCF₃ | |
| 4-270 | Et | CSOMe | SCF₃ | |
| 4-271 | n-Pr | CSOMe | SCF₃ | |
| 4-272 | i-Pr | CSOMe | SCF₃ | |
| 4-273 | c-Pr | CSOMe | SCF₃ | |
| 4-274 | n-Bu | CSOMe | SCF₃ | |
| 4-275 | n-Pen | CSOMe | SCF₃ | |
| 4-276 | CH₂CF₃ | CSOMe | SCF₃ | |
| 4-277 | CH₂C₂F₅ | CSOMe | SCF₃ | |
| 4-278 | CH₂CHF₂ | CSOMe | SCF₃ | |
| 4-279 | CH₂CF₂CHF₂ | CSOMe | SCF₃ | |
| 4-280 | CH₂SCH₃ | CSOMe | SCF₃ | |
| 4-281 | CH₂SOCH₃ | CSOMe | SCF₃ | |
| 4-282 | CH₂SO₂CH₃ | CSOMe | SCF₃ | |
| 4-283 | CH₂SCH₂CH₃ | CSOMe | SCF₃ | |
| 4-284 | CH₂SOCH₂CH₃ | CSOMe | SCF₃ | |
| 4-285 | CH₂SO₂CH₂CH₃ | CSOMe | SCF₃ | |
| 4-286 | CH₂CH₂SCH₃ | CSOMe | SCF₃ | |

TABLE 4-continued

| Compound No. | R³ | R⁴ | R⁵ | Physical property |
|---|---|---|---|---|
| 4-287 | $CH_2CH_2SOCH_3$ | CSOMe | $SCF_3$ | |
| 4-288 | $CH_2CH_2SO_2CH_3$ | CSOMe | $SCF_3$ | |
| 4-289 | $CH_2CH_2SCH_2CH_3$ | CSOMe | $SCF_3$ | |
| 4-290 | $CH_2CH_2SOCH_2CH_3$ | CSOMe | $SCF_3$ | |
| 4-291 | $CH_2CH_2SO_2CH_2CH_3$ | CSOMe | $SCF_3$ | |
| 4-292 | $CH_2CH_2SCF_3$ | CSOMe | $SCF_3$ | |
| 4-293 | $CH_2CH_2SOCF_3$ | CSOMe | $SCF_3$ | |
| 4-294 | $CH_2CH_2SO_2CF_3$ | CSOMe | $SCF_3$ | |
| 4-295 | $CH_2Ph$ | CSOMe | $SCF_3$ | |
| 4-296 | $CH_2C{\equiv}CH$ | CSOMe | $SCF_3$ | |
| 4-297 | $CH_2C{\equiv}CCH_3$ | CSOMe | $SCF_3$ | |
| 4-298 | $CH_2C{\equiv}N$ | CSOMe | $SCF_3$ | |
| 4-299 | $CH_2CH{=}CH_2$ | CSOMe | $SCF_3$ | |
| 4-300 | $CH_2CH{=}CHCH_3$ | CSOMe | $SCF_3$ | |
| 4-301 | $CH_2CH{=}C(CH_3)_3$ | CSOMe | $SCF_3$ | |
| 4-302 | $CH_2OCH_3$ | CSOMe | $SCF_3$ | |
| 4-303 | $CH_2CH_2OCH_3$ | CSOMe | $SCF_3$ | |
| 4-304 | $CH_2OCH_2CH_3$ | CSOMe | $SCF_3$ | |
| 4-305 | $CH_2CH_2OCH_2CH_3$ | CSOMe | $SCF_3$ | |
| 4-306 | H | CSOEt | $SCF_3$ | |
| 4-307 | Me | CSOEt | $SCF_3$ | |
| 4-308 | Et | CSOEt | $SCF_3$ | |
| 4-309 | n-Pr | CSOEt | $SCF_3$ | |
| 4-310 | i-Pr | CSOEt | $SCF_3$ | |
| 4-311 | c-Pr | CSOEt | $SCF_3$ | |
| 4-312 | n-Bu | CSOEt | $SCF_3$ | |
| 4-313 | n-Pen | CSOEt | $SCF_3$ | |
| 4-314 | $CH_2CF_3$ | CSOEt | $SCF_3$ | |
| 4-315 | $CH_2C_2F_5$ | CSOEt | $SCF_3$ | |
| 4-316 | $CH_2CHF_2$ | CSOEt | $SCF_3$ | |
| 4-317 | $CH_2CF_2CHF_2$ | CSOEt | $SCF_3$ | |
| 4-318 | $CH_2SCH_3$ | CSOEt | $SCF_3$ | |
| 4-319 | $CH_2SOCH_3$ | CSOEt | $SCF_3$ | |
| 4-320 | $CH_2SO_2CH_3$ | CSOEt | $SCF_3$ | |
| 4-321 | $CH_2SCH_2CH_3$ | CSOEt | $SCF_3$ | |
| 4-322 | $CH_2SOCH_2CH_3$ | CSOEt | $SCF_3$ | |
| 4-323 | $CH_2SO_2CH_2CH_3$ | CSOEt | $SCF_3$ | |
| 4-324 | $CH_2CH_2SCH_3$ | CSOEt | $SCF_3$ | |
| 4-325 | $CH_2CH_2SOCH_3$ | CSOEt | $SCF_3$ | |
| 4-326 | $CH_2CH_2SO_2CH_3$ | CSOEt | $SCF_3$ | |
| 4-327 | $CH_2CH_2SCH_2CH_3$ | CSOEt | $SCF_3$ | |
| 4-328 | $CH_2CH_2SOCH_2CH_3$ | CSOEt | $SCF_3$ | |
| 4-329 | $CH_2CH_2SO_2CH_2CH_3$ | CSOEt | $SCF_3$ | |
| 4-330 | $CH_2CH_2SCF_3$ | CSOEt | $SCF_3$ | |
| 4-331 | $CH_2CH_2SOCF_3$ | CSOEt | $SCF_3$ | |
| 4-332 | $CH_2CH_2SO_2CF_3$ | CSOEt | $SCF_3$ | |
| 4-333 | $CH_2Ph$ | CSOEt | $SCF_3$ | |
| 4-334 | $CH_2C{\equiv}CH$ | CSOEt | $SCF_3$ | |
| 4-335 | $CH_2C{\equiv}CCH_3$ | CSOEt | $SCF_3$ | |
| 4-336 | $CH_2C{\equiv}N$ | CSOEt | $SCF_3$ | |
| 4-337 | $CH_2CH{=}CH_2$ | CSOEt | $SCF_3$ | |
| 4-338 | $CH_2CH{=}CHCH_3$ | CSOEt | $SCF_3$ | |
| 4-339 | $CH_2CH{=}C(CH_3)_3$ | CSOEt | $SCF_3$ | |
| 4-340 | $CH_2OCH_3$ | CSOEt | $SCF_3$ | |
| 4-341 | $CH_2CH_2OCH_3$ | CSOEt | $SCF_3$ | |
| 4-342 | $CH_2OCH_2CH_3$ | CSOEt | $SCF_3$ | |
| 4-343 | $CH_2CH_2OCH_2CH_3$ | CSOEt | $SCF_3$ | |
| 4-344 | H | $CSN(Me)_2$ | $SCF_3$ | |
| 4-345 | Me | $CSN(Me)_2$ | $SCF_3$ | |
| 4-346 | Et | $CSN(Me)_2$ | $SCF_3$ | |
| 4-347 | n-Pr | $CSN(Me)_2$ | $SCF_3$ | |
| 4-348 | i-Pr | $CSN(Me)_2$ | $SCF_3$ | |
| 4-349 | c-Pr | $CSN(Me)_2$ | $SCF_3$ | |
| 4-350 | n-Bu | $CSN(Me)_2$ | $SCF_3$ | |
| 4-351 | n-Pen | $CSN(Me)_2$ | $SCF_3$ | |
| 4-352 | $CH_2CF_3$ | $CSN(Me)_2$ | $SCF_3$ | |
| 4-353 | $CH_2C_2F_5$ | $CSN(Me)_2$ | $SCF_3$ | |
| 4-354 | $CH_2CHF_2$ | $CSN(Me)_2$ | $SCF_3$ | |
| 4-355 | $CH_2CF_2CHF_2$ | $CSN(Me)_2$ | $SCF_3$ | |
| 4-356 | $CH_2SCH_3$ | $CSN(Me)_2$ | $SCF_3$ | |
| 4-357 | $CH_2SOCH_3$ | $CSN(Me)_2$ | $SCF_3$ | |
| 4-358 | $CH_2SO_2CH_3$ | $CSN(Me)_2$ | $SCF_3$ | |
| 4-359 | $CH_2SCH_2CH_3$ | $CSN(Me)_2$ | $SCF_3$ | |
| 4-360 | $CH_2SOCH_2CH_3$ | $CSN(Me)_2$ | $SCF_3$ | |
| 4-361 | $CH_2SO_2CH_2CH_3$ | $CSN(Me)_2$ | $SCF_3$ | |
| 4-362 | $CH_2CH_2SCH_3$ | $CSN(Me)_2$ | $SCF_3$ | |
| 4-363 | $CH_2CH_2SOCH_3$ | $CSN(Me)_2$ | $SCF_3$ | |
| 4-364 | $CH_2CH_2SO_2CH_3$ | $CSN(Me)_2$ | $SCF_3$ | |
| 4-365 | $CH_2CH_2SCH_2CH_3$ | $CSN(Me)_2$ | $SCF_3$ | |
| 4-366 | $CH_2CH_2SOCH_2CH_3$ | $CSN(Me)_2$ | $SCF_3$ | |
| 4-367 | $CH_2CH_2SO_2CH_2CH_3$ | $CSN(Me)_2$ | $SCF_3$ | |
| 4-368 | $CH_2CH_2SCF_3$ | $CSN(Me)_2$ | $SCF_3$ | |
| 4-369 | $CH_2CH_2SOCF_3$ | $CSN(Me)_2$ | $SCF_3$ | |
| 4-370 | $CH_2CH_2SO_2CF_3$ | $CSN(Me)_2$ | $SCF_3$ | |
| 4-371 | $CH_2Ph$ | $CSN(Me)_2$ | $SCF_3$ | |
| 4-372 | $CH_2C{\equiv}CH$ | $CSN(Me)_2$ | $SCF_3$ | |
| 4-373 | $CH_2C{\equiv}CCH_3$ | $CSN(Me)_2$ | $SCF_3$ | |
| 4-374 | $CH_2C{\equiv}N$ | $CSN(Me)_2$ | $SCF_3$ | |
| 4-375 | $CH_2CH{=}CH_2$ | $CSN(Me)_2$ | $SCF_3$ | |
| 4-376 | $CH_2CH{=}CHCH_3$ | $CSN(Me)_2$ | $SCF_3$ | |
| 4-377 | $CH_2CH{=}C(CH_3)_3$ | $CSN(Me)_2$ | $SCF_3$ | |
| 4-378 | $CH_2OCH_3$ | $CSN(Me)_2$ | $SCF_3$ | |
| 4-379 | $CH_2CH_2OCH_3$ | $CSN(Me)_2$ | $SCF_3$ | |
| 4-380 | $CH_2OCH_2CH_3$ | $CSN(Me)_2$ | $SCF_3$ | |
| 4-381 | $CH_2CH_2OCH_2CH_3$ | $CSN(Me)_2$ | $SCF_3$ | |
| 4-382 | H | CSNHEt | $SCF_3$ | |
| 4-383 | Me | CSNHEt | $SCF_3$ | |
| 4-384 | Et | CSNHEt | $SCF_3$ | |
| 4-385 | n-Pr | CSNHEt | $SCF_3$ | |
| 4-386 | i-Pr | CSNHEt | $SCF_3$ | |
| 4-387 | c-Pr | CSNHEt | $SCF_3$ | |
| 4-388 | n-Bu | CSNHEt | $SCF_3$ | |
| 4-389 | n-Pen | CSNHEt | $SCF_3$ | |
| 4-390 | $CH_2CF_3$ | CSNHEt | $SCF_3$ | |
| 4-391 | $CH_2C_2F_5$ | CSNHEt | $SCF_3$ | |
| 4-392 | $CH_2CHF_2$ | CSNHEt | $SCF_3$ | |
| 4-393 | $CH_2CF_2CHF_2$ | CSNHEt | $SCF_3$ | |
| 4-394 | $CH_2SCH_3$ | CSNHEt | $SCF_3$ | |
| 4-395 | $CH_2SOCH_3$ | CSNHEt | $SCF_3$ | |
| 4-396 | $CH_2SO_2CH_3$ | CSNHEt | $SCF_3$ | |
| 4-397 | $CH_2SCH_2CH_3$ | CSNHEt | $SCF_3$ | |
| 4-398 | $CH_2SOCH_2CH_3$ | CSNHEt | $SCF_3$ | |
| 4-399 | $CH_2SO_2CH_2CH_3$ | CSNHEt | $SCF_3$ | |
| 4-400 | $CH_2CH_2SCH_3$ | CSNHEt | $SCF_3$ | |
| 4-401 | $CH_2CH_2SOCH_3$ | CSNHEt | $SCF_3$ | |
| 4-402 | $CH_2CH_2SO_2CH_3$ | CSNHEt | $SCF_3$ | |
| 4-403 | $CH_2CH_2SCH_2CH_3$ | CSNHEt | $SCF_3$ | |
| 4-404 | $CH_2CH_2SOCH_2CH_3$ | CSNHEt | $SCF_3$ | |
| 4-405 | $CH_2CH_2SO_2CH_2CH_3$ | CSNHEt | $SCF_3$ | |
| 4-406 | $CH_2CH_2SCF_3$ | CSNHEt | $SCF_3$ | |
| 4-407 | $CH_2CH_2SOCF_3$ | CSNHEt | $SCF_3$ | |
| 4-408 | $CH_2CH_2SO_2CF_3$ | CSNHEt | $SCF_3$ | |
| 4-409 | $CH_2Ph$ | CSNHEt | $SCF_3$ | |
| 4-410 | $CH_2C{\equiv}CH$ | CSNHEt | $SCF_3$ | |
| 4-411 | $CH_2C{\equiv}CCH_3$ | CSNHEt | $SCF_3$ | |
| 4-412 | $CH_2C{\equiv}N$ | CSNHEt | $SCF_3$ | |
| 4-413 | $CH_2CH{=}CH_2$ | CSNHEt | $SCF_3$ | |
| 4-414 | $CH_2CH{=}CHCH_3$ | CSNHEt | $SCF_3$ | |
| 4-415 | $CH_2CH{=}C(CH_3)_3$ | CSNHEt | $SCF_3$ | |
| 4-416 | $CH_2OCH_3$ | CSNHEt | $SCF_3$ | |
| 4-417 | $CH_2CH_2OCH_3$ | CSNHEt | $SCF_3$ | |
| 4-418 | $CH_2OCH_2CH_3$ | CSNHEt | $SCF_3$ | |
| 4-419 | $CH_2CH_2OCH_2CH_3$ | CSNHEt | $SCF_3$ | |
| 4-420 | H | $SO_2Me$ | $SCF_3$ | |
| 4-421 | Me | $SO_2Me$ | $SCF_3$ | |
| 4-422 | Et | $SO_2Me$ | $SCF_3$ | |
| 4-423 | n-Pr | $SO_2Me$ | $SCF_3$ | |
| 4-424 | i-Pr | $SO_2Me$ | $SCF_3$ | |
| 4-425 | c-Pr | $SO_2Me$ | $SCF_3$ | |
| 4-426 | n-Bu | $SO_2Me$ | $SCF_3$ | |
| 4-427 | n-Pen | $SO_2Me$ | $SCF_3$ | |
| 4-428 | $CH_2CF_3$ | $SO_2Me$ | $SCF_3$ | |
| 4-429 | $CH_2C_2F_5$ | $SO_2Me$ | $SCF_3$ | |
| 4-430 | $CH_2CHF_2$ | $SO_2Me$ | $SCF_3$ | |
| 4-431 | $CH_2CF_2CHF_2$ | $SO_2Me$ | $SCF_3$ | |
| 4-432 | $CH_2SCH_3$ | $SO_2Me$ | $SCF_3$ | |
| 4-433 | $CH_2SOCH_3$ | $SO_2Me$ | $SCF_3$ | |
| 4-434 | $CH_2SO_2CH_3$ | $SO_2Me$ | $SCF_3$ | |
| 4-435 | $CH_2SCH_2CH_3$ | $SO_2Me$ | $SCF_3$ | |
| 4-436 | $CH_2SOCH_2CH_3$ | $SO_2Me$ | $SCF_3$ | |
| 4-437 | $CH_2SO_2CH_2CH_3$ | $SO_2Me$ | $SCF_3$ | |
| 4-438 | $CH_2CH_2SCH_3$ | $SO_2Me$ | $SCF_3$ | |
| 4-439 | $CH_2CH_2SOCH_3$ | $SO_2Me$ | $SCF_3$ | |
| 4-440 | $CH_2CH_2SO_2CH_3$ | $SO_2Me$ | $SCF_3$ | |

TABLE 4-continued

| Compound No. | $R^3$ | $R^4$ | $R^5$ | Physical property |
|---|---|---|---|---|
| 4-441 | $CH_2CH_2SCH_2CH_3$ | $SO_2Me$ | $SCF_3$ | |
| 4-442 | $CH_2CH_2SOCH_2CH_3$ | $SO_2Me$ | $SCF_3$ | |
| 4-443 | $CH_2CH_2SO_2CH_2CH_3$ | $SO_2Me$ | $SCF_3$ | |
| 4-444 | $CH_2CH_2SCF_3$ | $SO_2Me$ | $SCF_3$ | |
| 4-445 | $CH_2CH_2SOCF_3$ | $SO_2Me$ | $SCF_3$ | |
| 4-446 | $CH_2CH_2SO_2CF_3$ | $SO_2Me$ | $SCF_3$ | |
| 4-447 | $CH_2Ph$ | $SO_2Me$ | $SCF_3$ | |
| 4-448 | $CH_2C\equiv CH$ | $SO_2Me$ | $SCF_3$ | |
| 4-449 | $CH_2C\equiv CCH_3$ | $SO_2Me$ | $SCF_3$ | |
| 4-450 | $CH_2C\equiv N$ | $SO_2Me$ | $SCF_3$ | |
| 4-451 | $CH_2CH=CH_2$ | $SO_2Me$ | $SCF_3$ | |
| 4-452 | $CH_2CH=CHCH_3$ | $SO_2Me$ | $SCF_3$ | |
| 4-453 | $CH_2CH=C(CH_3)_3$ | $SO_2Me$ | $SCF_3$ | |
| 4-454 | $CH_2OCH_3$ | $SO_2Me$ | $SCF_3$ | |
| 4-455 | $CH_2CH_2OCH_3$ | $SO_2Me$ | $SCF_3$ | |
| 4-456 | $CH_2OCH_2CH_3$ | $SO_2Me$ | $SCF_3$ | |
| 4-457 | $CH_2CH_2OCH_2CH_3$ | $SO_2Me$ | $SCF_3$ | |
| 4-458 | H | H | $OCF_3$ | |
| 4-459 | Me | H | $OCF_3$ | |
| 4-460 | Et | H | $OCF_3$ | 81-82 |
| 4-461 | n-Pr | H | $OCF_3$ | |
| 4-462 | i-Pr | H | $OCF_3$ | |
| 4-463 | c-Pr | H | $OCF_3$ | |
| 4-464 | n-Bu | H | $OCF_3$ | |
| 4-465 | n-Pen | H | $OCF_3$ | |
| 4-466 | $CH_2CF_3$ | H | $OCF_3$ | 162-163 |
| 4-467 | $CH_2C_2F_5$ | H | $OCF_3$ | |
| 4-468 | $CH_2CHF_2$ | H | $OCF_3$ | |
| 4-469 | $CH_2CF_2CHF_2$ | H | $OCF_3$ | |
| 4-470 | $CH_2SCH_3$ | H | $OCF_3$ | |
| 4-471 | $CH_2SOCH_3$ | H | $OCF_3$ | |
| 4-472 | $CH_2SO_2CH_3$ | H | $OCF_3$ | |
| 4-473 | $CH_2SCH_2CH_3$ | H | $OCF_3$ | |
| 4-474 | $CH_2SOCH_2CH_3$ | H | $OCF_3$ | |
| 4-475 | $CH_2SO_2CH_2CH_3$ | H | $OCF_3$ | |
| 4-476 | $CH_2CH_2SCH_3$ | H | $OCF_3$ | |
| 4-477 | $CH_2CH_2SOCH_3$ | H | $OCF_3$ | |
| 4-478 | $CH_2CH_2SO_2CH_3$ | H | $OCF_3$ | |
| 4-479 | $CH_2CH_2SCH_2CH_3$ | H | $OCF_3$ | |
| 4-480 | $CH_2CH_2SOCH_2CH_3$ | H | $OCF_3$ | |
| 4-481 | $CH_2CH_2SO_2CH_2CH_3$ | H | $OCF_3$ | |
| 4-482 | $CH_2CH_2SCF_3$ | H | $OCF_3$ | |
| 4-483 | $CH_2CH_2SOCF_3$ | H | $OCF_3$ | |
| 4-484 | $CH_2CH_2SO_2CF_3$ | H | $OCF_3$ | |
| 4-485 | $CH_2Ph$ | H | $OCF_3$ | |
| 4-486 | $CH_2C\equiv CH$ | H | $OCF_3$ | |
| 4-487 | $CH_2C\equiv CCH_3$ | H | $OCF_3$ | |
| 4-488 | $CH_2C\equiv N$ | H | $OCF_3$ | |
| 4-489 | $CH_2CH=CH_2$ | H | $OCF_3$ | |
| 4-490 | $CH_2CH=CHCH_3$ | H | $OCF_3$ | |
| 4-491 | $CH_2CH=C(CH_3)_3$ | H | $OCF_3$ | |
| 4-492 | $CH_2OCH_3$ | H | $OCF_3$ | |
| 4-493 | $CH_2CH_2OCH_3$ | H | $OCF_3$ | |
| 4-494 | $CH_2OCH_2CH_3$ | H | $OCF_3$ | |
| 4-495 | $CH_2CH_2OCH_2CH_3$ | H | $OCF_3$ | |
| 4-496 | Ph | H | $OCF_3$ | |
| 4-497 | 4-SMePh | H | $OCF_3$ | |
| 4-498 | $4\text{-}CF_3Ph$ | H | $OCF_3$ | |
| 4-499 | 2-F,4-Cl—Ph | H | $OCF_3$ | |
| 4-500 | Me | Me | $OCF_3$ | |
| 4-501 | Et | Me | $OCF_3$ | |
| 4-502 | n-Pr | Me | $OCF_3$ | |
| 4-503 | i-Pr | Me | $OCF_3$ | |
| 4-504 | c-Pr | Me | $OCF_3$ | |
| 4-505 | n-Bu | Me | $OCF_3$ | |
| 4-506 | n-Pen | Me | $OCF_3$ | |
| 4-507 | $CH_2CF_3$ | Me | $OCF_3$ | |
| 4-508 | $CH_2C_2F_5$ | Me | $OCF_3$ | |
| 4-509 | $CH_2CHF_2$ | Me | $OCF_3$ | |
| 4-510 | $CH_2CF_2CHF_2$ | Me | $OCF_3$ | |
| 4-511 | $CH_2SCH_3$ | Me | $OCF_3$ | |
| 4-512 | $CH_2SOCH_3$ | Me | $OCF_3$ | |
| 4-513 | $CH_2SO_2CH_3$ | Me | $OCF_3$ | |
| 4-514 | $CH_2SCH_2CH_3$ | Me | $OCF_3$ | |
| 4-515 | $CH_2SOCH_2CH_3$ | Me | $OCF_3$ | |
| 4-516 | $CH_2SO_2CH_2CH_3$ | Me | $OCF_3$ | |
| 4-517 | $CH_2CH_2SCH_3$ | Me | $OCF_3$ | |
| 4-518 | $CH_2CH_2SOCH_3$ | Me | $OCF_3$ | |
| 4-519 | $CH_2CH_2SO_2CH_3$ | Me | $OCF_3$ | |
| 4-520 | $CH_2CH_2SCH_2CH_3$ | Me | $OCF_3$ | |
| 4-521 | $CH_2CH_2SOCH_2CH_3$ | Me | $OCF_3$ | |
| 4-522 | $CH_2CH_2SO_2CH_2CH_3$ | Me | $OCF_3$ | |
| 4-523 | $CH_2CH_2SCF_3$ | Me | $OCF_3$ | |
| 4-524 | $CH_2CH_2SOCF_3$ | Me | $OCF_3$ | |
| 4-525 | $CH_2CH_2SO_2CF_3$ | Me | $OCF_3$ | |
| 4-526 | $CH_2Ph$ | Me | $OCF_3$ | |
| 4-527 | $CH_2C\equiv CH$ | Me | $OCF_3$ | |
| 4-528 | $CH_2C\equiv CCH_3$ | Me | $OCF_3$ | |
| 4-529 | $CH_2C\equiv N$ | Me | $OCF_3$ | |
| 4-530 | $CH_2CH=CH_2$ | Me | $OCF_3$ | |
| 4-531 | $CH_2CH=CHCH_3$ | Me | $OCF_3$ | |
| 4-532 | $CH_2CH=C(CH_3)_3$ | Me | $OCF_3$ | |
| 4-533 | $CH_2OCH_3$ | Me | $OCF_3$ | |
| 4-534 | $CH_2CH_2OCH_3$ | Me | $OCF_3$ | |
| 4-535 | $CH_2OCH_2CH_3$ | Me | $OCF_3$ | |
| 4-536 | $CH_2CH_2OCH_2CH_3$ | Me | $OCF_3$ | |
| 4-537 | Et | Et | $OCF_3$ | |
| 4-538 | n-Pr | Et | $OCF_3$ | |
| 4-539 | i-Pr | Et | $OCF_3$ | |
| 4-540 | c-Pr | Et | $OCF_3$ | |
| 4-541 | n-Bu | Et | $OCF_3$ | |
| 4-542 | n-Pen | Et | $OCF_3$ | |
| 4-543 | $CH_2CF_3$ | Et | $OCF_3$ | |
| 4-544 | $CH_2C_2F_5$ | Et | $OCF_3$ | |
| 4-545 | $CH_2CHF_2$ | Et | $OCF_3$ | |
| 4-546 | $CH_2CF_2CHF_2$ | Et | $OCF_3$ | |
| 4-547 | $CH_2SCH_3$ | Et | $OCF_3$ | |
| 4-548 | $CH_2SOCH_3$ | Et | $OCF_3$ | |
| 4-549 | $CH_2SO_2CH_3$ | Et | $OCF_3$ | |
| 4-550 | $CH_2SCH_2CH_3$ | Et | $OCF_3$ | |
| 4-551 | $CH_2SOCH_2CH_3$ | Et | $OCF_3$ | |
| 4-552 | $CH_2SO_2CH_2CH_3$ | Et | $OCF_3$ | |
| 4-553 | $CH_2CH_2SCH_3$ | Et | $OCF_3$ | |
| 4-554 | $CH_2CH_2SOCH_3$ | Et | $OCF_3$ | |
| 4-555 | $CH_2CH_2SO_2CH_3$ | Et | $OCF_3$ | |
| 4-556 | $CH_2CH_2SCH_2CH_3$ | Et | $OCF_3$ | |
| 4-557 | $CH_2CH_2SOCH_2CH_3$ | Et | $OCF_3$ | |
| 4-558 | $CH_2CH_2SO_2CH_2CH_3$ | Et | $OCF_3$ | |
| 4-559 | $CH_2CH_2SCF_3$ | Et | $OCF_3$ | |
| 4-560 | $CH_2CH_2SOCF_3$ | Et | $OCF_3$ | |
| 4-561 | $CH_2CH_2SO_2CF_3$ | Et | $OCF_3$ | |
| 4-562 | $CH_2Ph$ | Et | $OCF_3$ | |
| 4-563 | $CH_2C\equiv CH$ | Et | $OCF_3$ | |
| 4-564 | $CH_2C\equiv CCH_3$ | Et | $OCF_3$ | |
| 4-565 | $CH_2C\equiv N$ | Et | $OCF_3$ | |
| 4-566 | $CH_2CH=CH_2$ | Et | $OCF_3$ | |
| 4-567 | $CH_2CH=CHCH_3$ | Et | $OCF_3$ | |
| 4-568 | $CH_2CH=C(CH_3)_3$ | Et | $OCF_3$ | |
| 4-569 | $CH_2OCH_3$ | Et | $OCF_3$ | |
| 4-570 | $CH_2CH_2OCH_3$ | Et | $OCF_3$ | |
| 4-571 | $CH_2OCH_2CH_3$ | Et | $OCF_3$ | |
| 4-572 | $CH_2CH_2OCH_2CH_3$ | Et | $OCF_3$ | |
| 4-573 | H | Ac | $OCF_3$ | 198-199 |
| 4-574 | Me | Ac | $OCF_3$ | |
| 4-575 | Et | Ac | $OCF_3$ | 160-161 |
| 4-576 | n-Pr | Ac | $OCF_3$ | |
| 4-577 | i-Pr | Ac | $OCF_3$ | |
| 4-578 | c-Pr | Ac | $OCF_3$ | |
| 4-579 | n-Bu | Ac | $OCF_3$ | |
| 4-580 | n-Pen | Ac | $OCF_3$ | |
| 4-581 | $CH_2CF_3$ | Ac | $OCF_3$ | |
| 4-582 | $CH_2C_2F_5$ | Ac | $OCF_3$ | |
| 4-583 | $CH_2CHF_2$ | Ac | $OCF_3$ | |
| 4-584 | $CH_2CF_2CHF_2$ | Ac | $OCF_3$ | |
| 4-585 | $CH_2SCH_3$ | Ac | $OCF_3$ | |
| 4-586 | $CH_2SOCH_3$ | Ac | $OCF_3$ | |
| 4-587 | $CH_2SO_2CH_3$ | Ac | $OCF_3$ | |
| 4-588 | $CH_2SCH_2CH_3$ | Ac | $OCF_3$ | |
| 4-589 | $CH_2SOCH_2CH_3$ | Ac | $OCF_3$ | |
| 4-590 | $CH_2SO_2CH_2CH_3$ | Ac | $OCF_3$ | |
| 4-591 | $CH_2CH_2SCH_3$ | Ac | $OCF_3$ | |
| 4-592 | $CH_2CH_2SOCH_3$ | Ac | $OCF_3$ | |
| 4-593 | $CH_2CH_2SO_2CH_3$ | Ac | $OCF_3$ | |
| 4-594 | $CH_2CH_2SCH_2CH_3$ | Ac | $OCF_3$ | |

TABLE 4-continued

| Compound No. | R³ | R⁴ | R⁵ | Physical property |
|---|---|---|---|---|
| 4-595 | CH₂CH₂SOCH₂CH₃ | Ac | OCF₃ | |
| 4-596 | CH₂CH₂SO₂CH₂CH₃ | Ac | OCF₃ | |
| 4-597 | CH₂CH₂SCF₃ | Ac | OCF₃ | |
| 4-598 | CH₂CH₂SOCF₃ | Ac | OCF₃ | |
| 4-599 | CH₂CH₂SO₂CF₃ | Ac | OCF₃ | |
| 4-600 | CH₂Ph | Ac | OCF₃ | |
| 4-601 | CH₂C≡CH | Ac | OCF₃ | |
| 4-602 | CH₂C≡CCH₃ | Ac | OCF₃ | |
| 4-603 | CH₂C≡N | Ac | OCF₃ | |
| 4-604 | CH₂CH═CH₂ | Ac | OCF₃ | |
| 4-605 | CH₂CH═CHCH₃ | Ac | OCF₃ | |
| 4-606 | CH₂CH═C(CH₃)₃ | Ac | OCF₃ | |
| 4-607 | CH₂OCH₃ | Ac | OCF₃ | |
| 4-608 | CH₂CH₂OCH₃ | Ac | OCF₃ | |
| 4-609 | CH₂OCH₂CH₃ | Ac | OCF₃ | |
| 4-610 | CH₂CH₂OCH₂CH₃ | Ac | OCF₃ | |
| 4-611 | H | CO₂Me | OCF₃ | 219-220 |
| 4-612 | Me | CO₂Me | OCF₃ | |
| 4-613 | Et | CO₂Me | OCF₃ | |
| 4-614 | n-Pr | CO₂Me | OCF₃ | |
| 4-615 | i-Pr | CO₂Me | OCF₃ | |
| 4-616 | c-Pr | CO₂Me | OCF₃ | |
| 4-617 | n-Bu | CO₂Me | OCF₃ | |
| 4-618 | n-Pen | CO₂Me | OCF₃ | |
| 4-619 | CH₂CF₃ | CO₂Me | OCF₃ | |
| 4-620 | CH₂C₂F₅ | CO₂Me | OCF₃ | |
| 4-621 | CH₂CHF₂ | CO₂Me | OCF₃ | |
| 4-622 | CH₂CF₂CHF₂ | CO₂Me | OCF₃ | |
| 4-623 | CH₂SCH₃ | CO₂Me | OCF₃ | |
| 4-624 | CH₂SOCH₃ | CO₂Me | OCF₃ | |
| 4-625 | CH₂SO₂CH₃ | CO₂Me | OCF₃ | |
| 4-626 | CH₂SCH₂CH₃ | CO₂Me | OCF₃ | |
| 4-627 | CH₂SOCH₂CH₃ | CO₂Me | OCF₃ | |
| 4-628 | CH₂SO₂CH₂CH₃ | CO₂Me | OCF₃ | |
| 4-629 | CH₂CH₂SCH₃ | CO₂Me | OCF₃ | |
| 4-630 | CH₂CH₂SOCH₃ | CO₂Me | OCF₃ | |
| 4-631 | CH₂CH₂SO₂CH₃ | CO₂Me | OCF₃ | |
| 4-632 | CH₂CH₂SCH₂CH₃ | CO₂Me | OCF₃ | |
| 4-633 | CH₂CH₂SOCH₂CH₃ | CO₂Me | OCF₃ | |
| 4-634 | CH₂CH₂SO₂CH₂CH₃ | CO₂Me | OCF₃ | |
| 4-635 | CH₂CH₂SCF₃ | CO₂Me | OCF₃ | |
| 4-636 | CH₂CH₂SOCF₃ | CO₂Me | OCF₃ | |
| 4-637 | CH₂CH₂SO₂CF₃ | CO₂Me | OCF₃ | |
| 4-638 | CH₂Ph | CO₂Me | OCF₃ | |
| 4-639 | CH₂C≡CH | CO₂Me | OCF₃ | |
| 4-640 | CH₂C≡CCH₃ | CO₂Me | OCF₃ | |
| 4-641 | CH₂C≡N | CO₂Me | OCF₃ | |
| 4-642 | CH₂CH═CH₂ | CO₂Me | OCF₃ | |
| 4-643 | CH₂CH═CHCH₃ | CO₂Me | OCF₃ | |
| 4-644 | CH₂CH═C(CH₃)₃ | CO₂Me | OCF₃ | |
| 4-645 | CH₂OCH₃ | CO₂Me | OCF₃ | |
| 4-646 | CH₂CH₂OCH₃ | CO₂Me | OCF₃ | |
| 4-647 | CH₂OCH₂CH₃ | CO₂Me | OCF₃ | |
| 4-648 | CH₂CH₂OCH₂CH₃ | CO₂Me | OCF₃ | |
| 4-649 | H | CO₂Et | OCF₃ | |
| 4-650 | Me | CO₂Et | OCF₃ | |
| 4-651 | Et | CO₂Et | OCF₃ | |
| 4-652 | n-Pr | CO₂Et | OCF₃ | |
| 4-653 | i-Pr | CO₂Et | OCF₃ | |
| 4-654 | c-Pr | CO₂Et | OCF₃ | |
| 4-655 | n-Bu | CO₂Et | OCF₃ | |
| 4-656 | n-Pen | CO₂Et | OCF₃ | |
| 4-657 | CH₂CF₃ | CO₂Et | OCF₃ | |
| 4-658 | CH₂C₂F₅ | CO₂Et | OCF₃ | |
| 4-659 | CH₂CHF₂ | CO₂Et | OCF₃ | |
| 4-660 | CH₂CF₂CHF₂ | CO₂Et | OCF₃ | |
| 4-661 | CH₂SCH₃ | CO₂Et | OCF₃ | |
| 4-662 | CH₂SOCH₃ | CO₂Et | OCF₃ | |
| 4-663 | CH₂SO₂CH₃ | CO₂Et | OCF₃ | |
| 4-664 | CH₂SCH₂CH₃ | CO₂Et | OCF₃ | |
| 4-665 | CH₂SOCH₂CH₃ | CO₂Et | OCF₃ | |
| 4-666 | CH₂SO₂CH₂CH₃ | CO₂Et | OCF₃ | |
| 4-667 | CH₂CH₂SCH₃ | CO₂Et | OCF₃ | |
| 4-668 | CH₂CH₂SOCH₃ | CO₂Et | OCF₃ | |
| 4-669 | CH₂CH₂SO₂CH₃ | CO₂Et | OCF₃ | |
| 4-670 | CH₂CH₂SCH₂CH₃ | CO₂Et | OCF₃ | |
| 4-671 | CH₂CH₂SOCH₂CH₃ | CO₂Et | OCF₃ | |
| 4-672 | CH₂CH₂SO₂CH₂CH₃ | CO₂Et | OCF₃ | |
| 4-673 | CH₂CH₂SCF₃ | CO₂Et | OCF₃ | |
| 4-674 | CH₂CH₂SOCF₃ | CO₂Et | OCF₃ | |
| 4-675 | CH₂CH₂SO₂CF₃ | CO₂Et | OCF₃ | |
| 4-676 | CH₂Ph | CO₂Et | OCF₃ | |
| 4-677 | CH₂C≡CH | CO₂Et | OCF₃ | |
| 4-678 | CH₂C≡CCH₃ | CO₂Et | OCF₃ | |
| 4-679 | CH₂C≡N | CO₂Et | OCF₃ | |
| 4-680 | CH₂CH═CH₂ | CO₂Et | OCF₃ | |
| 4-681 | CH₂CH═CHCH₃ | CO₂Et | OCF₃ | |
| 4-682 | CH₂CH═C(CH₃)₃ | CO₂Et | OCF₃ | |
| 4-683 | CH₂OCH₃ | CO₂Et | OCF₃ | |
| 4-684 | CH₂CH₂OCH₃ | CO₂Et | OCF₃ | |
| 4-685 | CH₂OCH₂CH₃ | CO₂Et | OCF₃ | |
| 4-686 | CH₂CH₂OCH₂CH₃ | CO₂Et | OCF₃ | |
| 4-687 | H | COCF₃ | OCF₃ | |
| 4-688 | Me | COCF₃ | OCF₃ | |
| 4-689 | Et | COCF₃ | OCF₃ | |
| 4-690 | n-Pr | COCF₃ | OCF₃ | |
| 4-691 | i-Pr | COCF₃ | OCF₃ | |
| 4-692 | c-Pr | COCF₃ | OCF₃ | |
| 4-693 | n-Bu | COCF₃ | OCF₃ | |
| 4-694 | n-Pen | COCF₃ | OCF₃ | |
| 4-695 | CH₂CF₃ | COCF₃ | OCF₃ | |
| 4-696 | CH₂C₂F₅ | COCF₃ | OCF₃ | |
| 4-697 | CH₂CHF₂ | COCF₃ | OCF₃ | |
| 4-698 | CH₂CF₂CHF₂ | COCF₃ | OCF₃ | |
| 4-699 | CH₂SCH₃ | COCF₃ | OCF₃ | |
| 4-700 | CH₂SOCH₃ | COCF₃ | OCF₃ | |
| 4-701 | CH₂SO₂CH₃ | COCF₃ | OCF₃ | |
| 4-702 | CH₂SCH₂CH₃ | COCF₃ | OCF₃ | |
| 4-703 | CH₂SOCH₂CH₃ | COCF₃ | OCF₃ | |
| 4-704 | CH₂SO₂CH₂CH₃ | COCF₃ | OCF₃ | |
| 4-705 | CH₂CH₂SCH₃ | COCF₃ | OCF₃ | |
| 4-706 | CH₂CH₂SOCH₃ | COCF₃ | OCF₃ | |
| 4-707 | CH₂CH₂SO₂CH₃ | COCF₃ | OCF₃ | |
| 4-708 | CH₂CH₂SCH₂CH₃ | COCF₃ | OCF₃ | |
| 4-709 | CH₂CH₂SOCH₂CH₃ | COCF₃ | OCF₃ | |
| 4-710 | CH₂CH₂SO₂CH₂CH₃ | COCF₃ | OCF₃ | |
| 4-711 | CH₂CH₂SCF₃ | COCF₃ | OCF₃ | |
| 4-712 | CH₂CH₂SOCF₃ | COCF₃ | OCF₃ | |
| 4-713 | CH₂CH₂SO₂CF₃ | COCF₃ | OCF₃ | |
| 4-714 | CH₂Ph | COCF₃ | OCF₃ | |
| 4-715 | CH₂C≡CH | COCF₃ | OCF₃ | |
| 4-716 | CH₂C≡CCH₃ | COCF₃ | OCF₃ | |
| 4-717 | CH₂C≡N | COCF₃ | OCF₃ | |
| 4-718 | CH₂CH═CH₂ | COCF₃ | OCF₃ | |
| 4-719 | CH₂CH═CHCH₃ | COCF₃ | OCF₃ | |
| 4-720 | CH₂CH═C(CH₃)₃ | COCF₃ | OCF₃ | |
| 4-721 | CH₂OCH₃ | COCF₃ | OCF₃ | |
| 4-722 | CH₂CH₂OCH₃ | COCF₃ | OCF₃ | |
| 4-723 | CH₂OCH₂CH₃ | COCF₃ | OCF₃ | |
| 4-724 | CH₂CH₂OCH₂CH₃ | COCF₃ | OCF₃ | |
| 4-725 | H | CSOMe | OCF₃ | |
| 4-726 | Me | CSOMe | OCF₃ | |
| 4-727 | Et | CSOMe | OCF₃ | |
| 4-728 | n-Pr | CSOMe | OCF₃ | |
| 4-729 | i-Pr | CSOMe | OCF₃ | |
| 4-730 | c-Pr | CSOMe | OCF₃ | |
| 4-731 | n-Bu | CSOMe | OCF₃ | |
| 4-732 | n-Pen | CSOMe | OCF₃ | |
| 4-733 | CH₂CF₃ | CSOMe | OCF₃ | |
| 4-734 | CH₂C₂F₅ | CSOMe | OCF₃ | |
| 4-735 | CH₂CHF₂ | CSOMe | OCF₃ | |
| 4-736 | CH₂CF₂CHF₂ | CSOMe | OCF₃ | |
| 4-737 | CH₂SCH₃ | CSOMe | OCF₃ | |
| 4-738 | CH₂SOCH₃ | CSOMe | OCF₃ | |
| 4-739 | CH₂SO₂CH₃ | CSOMe | OCF₃ | |
| 4-740 | CH₂SCH₂CH₃ | CSOMe | OCF₃ | |
| 4-741 | CH₂SOCH₂CH₃ | CSOMe | OCF₃ | |
| 4-742 | CH₂SO₂CH₂CH₃ | CSOMe | OCF₃ | |
| 4-743 | CH₂CH₂SCH₃ | CSOMe | OCF₃ | |
| 4-744 | CH₂CH₂SOCH₃ | CSOMe | OCF₃ | |
| 4-745 | CH₂CH₂SO₂CH₃ | CSOMe | OCF₃ | |
| 4-746 | CH₂CH₂SCH₂CH₃ | CSOMe | OCF₃ | |
| 4-747 | CH₂CH₂SOCH₂CH₃ | CSOMe | OCF₃ | |
| 4-748 | CH₂CH₂SO₂CH₂CH₃ | CSOMe | OCF₃ | |

TABLE 4-continued

| Compound No. | R³ | R⁴ | R⁵ | Physical property |
|---|---|---|---|---|
| 4-749 | CH₂CH₂SCF₃ | CSOMe | OCF₃ | |
| 4-750 | CH₂CH₂SOCF₃ | CSOMe | OCF₃ | |
| 4-751 | CH₂CH₂SO₂CF₃ | CSOMe | OCF₃ | |
| 4-752 | CH₂Ph | CSOMe | OCF₃ | |
| 4-753 | CH₂C≡CH | CSOMe | OCF₃ | |
| 4-754 | CH₂C≡CCH₃ | CSOMe | OCF₃ | |
| 4-755 | CH₂C≡N | CSOMe | OCF₃ | |
| 4-756 | CH₂CH=CH₂ | CSOMe | OCF₃ | |
| 4-757 | CH₂CH=CHCH₃ | CSOMe | OCF₃ | |
| 4-758 | CH₂CH=C(CH₃)₃ | CSOMe | OCF₃ | |
| 4-759 | CH₂OCH₃ | CSOMe | OCF₃ | |
| 4-760 | CH₂CH₂OCH₃ | CSOMe | OCF₃ | |
| 4-761 | CH₂OCH₂CH₃ | CSOMe | OCF₃ | |
| 4-762 | CH₂CH₂OCH₂CH₃ | CSOMe | OCF₃ | |
| 4-763 | H | CSOEt | OCF₃ | |
| 4-764 | Me | CSOEt | OCF₃ | |
| 4-765 | Et | CSOEt | OCF₃ | |
| 4-766 | n-Pr | CSOEt | OCF₃ | |
| 4-767 | i-Pr | CSOEt | OCF₃ | |
| 4-768 | c-Pr | CSOEt | OCF₃ | |
| 4-769 | n-Bu | CSOEt | OCF₃ | |
| 4-770 | n-Pen | CSOEt | OCF₃ | |
| 4-771 | CH₂CF₃ | CSOEt | OCF₃ | |
| 4-772 | CH₂C₂F₅ | CSOEt | OCF₃ | |
| 4-773 | CH₂CHF₂ | CSOEt | OCF₃ | |
| 4-774 | CH₂CF₂CHF₂ | CSOEt | OCF₃ | |
| 4-775 | CH₂SCH₃ | CSOEt | OCF₃ | |
| 4-776 | CH₂SOCH₃ | CSOEt | OCF₃ | |
| 4-777 | CH₂SO₂CH₃ | CSOEt | OCF₃ | |
| 4-778 | CH₂SCH₂CH₃ | CSOEt | OCF₃ | |
| 4-779 | CH₂SOCH₂CH₃ | CSOEt | OCF₃ | |
| 4-780 | CH₂SO₂CH₂CH₃ | CSOEt | OCF₃ | |
| 4-781 | CH₂CH₂SCH₃ | CSOEt | OCF₃ | |
| 4-782 | CH₂CH₂SOCH₃ | CSOEt | OCF₃ | |
| 4-783 | CH₂CH₂SO₂CH₃ | CSOEt | OCF₃ | |
| 4-784 | CH₂CH₂SCH₂CH₃ | CSOEt | OCF₃ | |
| 4-785 | CH₂CH₂SOCH₂CH₃ | CSOEt | OCF₃ | |
| 4-786 | CH₂CH₂SO₂CH₂CH₃ | CSOEt | OCF₃ | |
| 4-787 | CH₂CH₂SCF₃ | CSOEt | OCF₃ | |
| 4-788 | CH₂CH₂SOCF₃ | CSOEt | OCF₃ | |
| 4-789 | CH₂CH₂SO₂CF₃ | CSOEt | OCF₃ | |
| 4-790 | CH₂Ph | CSOEt | OCF₃ | |
| 4-791 | CH₂C≡CH | CSOEt | OCF₃ | |
| 4-792 | CH₂C≡CCH₃ | CSOEt | OCF₃ | |
| 4-793 | CH₂C≡N | CSOEt | OCF₃ | |
| 4-794 | CH₂CH=CH₂ | CSOEt | OCF₃ | |
| 4-795 | CH₂CH=CHCH₃ | CSOEt | OCF₃ | |
| 4-796 | CH₂CH=C(CH₃)₃ | CSOEt | OCF₃ | |
| 4-797 | CH₂OCH₃ | CSOEt | OCF₃ | |
| 4-798 | CH₂CH₂OCH₃ | CSOEt | OCF₃ | |
| 4-799 | CH₂OCH₂CH₃ | CSOEt | OCF₃ | |
| 4-800 | CH₂CH₂OCH₂CH₃ | CSOEt | OCF₃ | |
| 4-801 | H | CSN(Me)₂ | OCF₃ | |
| 4-802 | Me | CSN(Me)₂ | OCF₃ | |
| 4-803 | Et | CSN(Me)₂ | OCF₃ | |
| 4-804 | n-Pr | CSN(Me)₂ | OCF₃ | |
| 4-805 | i-Pr | CSN(Me)₂ | OCF₃ | |
| 4-806 | c-Pr | CSN(Me)₂ | OCF₃ | |
| 4-807 | n-Bu | CSN(Me)₂ | OCF₃ | |
| 4-808 | n-Pen | CSN(Me)₂ | OCF₃ | |
| 4-809 | CH₂CF₃ | CSN(Me)₂ | OCF₃ | |
| 4-810 | CH₂C₂F₅ | CSN(Me)₂ | OCF₃ | |
| 4-811 | CH₂CHF₂ | CSN(Me)₂ | OCF₃ | |
| 4-812 | CH₂CF₂CHF₂ | CSN(Me)₂ | OCF₃ | |
| 4-813 | CH₂SCH₃ | CSN(Me)₂ | OCF₃ | |
| 4-814 | CH₂SOCH₃ | CSN(Me)₂ | OCF₃ | |
| 4-815 | CH₂SO₂CH₃ | CSN(Me)₂ | OCF₃ | |
| 4-816 | CH₂SCH₂CH₃ | CSN(Me)₂ | OCF₃ | |
| 4-817 | CH₂SOCH₂CH₃ | CSN(Me)₂ | OCF₃ | |
| 4-818 | CH₂SO₂CH₂CH₃ | CSN(Me)₂ | OCF₃ | |
| 4-819 | CH₂CH₂SCH₃ | CSN(Me)₂ | OCF₃ | |
| 4-820 | CH₂CH₂SOCH₃ | CSN(Me)₂ | OCF₃ | |
| 4-821 | CH₂CH₂SO₂CH₃ | CSN(Me)₂ | OCF₃ | |
| 4-822 | CH₂CH₂SCH₂CH₃ | CSN(Me)₂ | OCF₃ | |
| 4-823 | CH₂CH₂SOCH₂CH₃ | CSN(Me)₂ | OCF₃ | |
| 4-824 | CH₂CH₂SO₂CH₂CH₃ | CSN(Me)₂ | OCF₃ | |
| 4-825 | CH₂CH₂SCF₃ | CSN(Me)₂ | OCF₃ | |
| 4-826 | CH₂CH₂SOCF₃ | CSN(Me)₂ | OCF₃ | |
| 4-827 | CH₂CH₂SO₂CF₃ | CSN(Me)₂ | OCF₃ | |
| 4-828 | CH₂Ph | CSN(Me)₂ | OCF₃ | |
| 4-829 | CH₂C≡CH | CSN(Me)₂ | OCF₃ | |
| 4-830 | CH₂C≡CCH₃ | CSN(Me)₂ | OCF₃ | |
| 4-831 | CH₂C≡N | CSN(Me)₂ | OCF₃ | |
| 4-832 | CH₂CH=CH₂ | CSN(Me)₂ | OCF₃ | |
| 4-833 | CH₂CH=CHCH₃ | CSN(Me)₂ | OCF₃ | |
| 4-834 | CH₂CH=C(CH₃)₃ | CSN(Me)₂ | OCF₃ | |
| 4-835 | CH₂OCH₃ | CSN(Me)₂ | OCF₃ | |
| 4-836 | CH₂CH₂OCH₃ | CSN(Me)₂ | OCF₃ | |
| 4-837 | CH₂OCH₂CH₃ | CSN(Me)₂ | OCF₃ | |
| 4-838 | CH₂CH₂OCH₂CH₃ | CSN(Me)₂ | OCF₃ | |
| 4-839 | H | CSNHEt | OCF₃ | |
| 4-840 | Me | CSNHEt | OCF₃ | |
| 4-841 | Et | CSNHEt | OCF₃ | |
| 4-842 | n-Pr | CSNHEt | OCF₃ | |
| 4-843 | i-Pr | CSNHEt | OCF₃ | |
| 4-844 | c-Pr | CSNHEt | OCF₃ | |
| 4-845 | n-Bu | CSNHEt | OCF₃ | |
| 4-846 | n-Pen | CSNHEt | OCF₃ | |
| 4-847 | CH₂CF₃ | CSNHEt | OCF₃ | |
| 4-848 | CH₂C₂F₅ | CSNHEt | OCF₃ | |
| 4-849 | CH₂CHF₂ | CSNHEt | OCF₃ | |
| 4-850 | CH₂CF₂CHF₂ | CSNHEt | OCF₃ | |
| 4-851 | CH₂SCH₃ | CSNHEt | OCF₃ | |
| 4-852 | CH₂SOCH₃ | CSNHEt | OCF₃ | |
| 4-853 | CH₂SO₂CH₃ | CSNHEt | OCF₃ | |
| 4-854 | CH₂SCH₂CH₃ | CSNHEt | OCF₃ | |
| 4-855 | CH₂SOCH₂CH₃ | CSNHEt | OCF₃ | |
| 4-856 | CH₂SO₂CH₂CH₃ | CSNHEt | OCF₃ | |
| 4-857 | CH₂CH₂SCH₃ | CSNHEt | OCF₃ | |
| 4-858 | CH₂CH₂SOCH₃ | CSNHEt | OCF₃ | |
| 4-859 | CH₂CH₂SO₂CH₃ | CSNHEt | OCF₃ | |
| 4-860 | CH₂CH₂SCH₂CH₃ | CSNHEt | OCF₃ | |
| 4-861 | CH₂CH₂SOCH₂CH₃ | CSNHEt | OCF₃ | |
| 4-862 | CH₂CH₂SO₂CH₂CH₃ | CSNHEt | OCF₃ | |
| 4-863 | CH₂CH₂SCF₃ | CSNHEt | OCF₃ | |
| 4-864 | CH₂CH₂SOCF₃ | CSNHEt | OCF₃ | |
| 4-865 | CH₂CH₂SO₂CF₃ | CSNHEt | OCF₃ | |
| 4-866 | CH₂Ph | CSNHEt | OCF₃ | |
| 4-867 | CH₂C≡CH | CSNHEt | OCF₃ | |
| 4-868 | CH₂C≡CCH₃ | CSNHEt | OCF₃ | |
| 4-869 | CH₂C≡N | CSNHEt | OCF₃ | |
| 4-870 | CH₂CH=CH₂ | CSNHEt | OCF₃ | |
| 4-871 | CH₂CH=CHCH₃ | CSNHEt | OCF₃ | |
| 4-872 | CH₂CH=C(CH₃)₃ | CSNHEt | OCF₃ | |
| 4-873 | CH₂OCH₃ | CSNHEt | OCF₃ | |
| 4-874 | CH₂CH₂OCH₃ | CSNHEt | OCF₃ | |
| 4-875 | CH₂OCH₂CH₃ | CSNHEt | OCF₃ | |
| 4-876 | CH₂CH₂OCH₂CH₃ | CSNHEt | OCF₃ | |
| 4-877 | H | SO₂Me | OCF₃ | |
| 4-878 | Me | SO₂Me | OCF₃ | |
| 4-879 | Et | SO₂Me | OCF₃ | |
| 4-880 | n-Pr | SO₂Me | OCF₃ | |
| 4-881 | i-Pr | SO₂Me | OCF₃ | |
| 4-882 | c-Pr | SO₂Me | OCF₃ | |
| 4-883 | n-Bu | SO₂Me | OCF₃ | |
| 4-884 | n-Pen | SO₂Me | OCF₃ | |
| 4-885 | CH₂CF₃ | SO₂Me | OCF₃ | |
| 4-886 | CH₂C₂F₅ | SO₂Me | OCF₃ | |
| 4-887 | CH₂CHF₂ | SO₂Me | OCF₃ | |
| 4-888 | CH₂CF₂CHF₂ | SO₂Me | OCF₃ | |
| 4-889 | CH₂SCH₃ | SO₂Me | OCF₃ | |
| 4-890 | CH₂SOCH₃ | SO₂Me | OCF₃ | |
| 4-891 | CH₂SO₂CH₃ | SO₂Me | OCF₃ | |
| 4-892 | CH₂SCH₂CH₃ | SO₂Me | OCF₃ | |
| 4-893 | CH₂SOCH₂CH₃ | SO₂Me | OCF₃ | |
| 4-894 | CH₂SO₂CH₂CH₃ | SO₂Me | OCF₃ | |
| 4-895 | CH₂CH₂SCH₃ | SO₂Me | OCF₃ | |
| 4-896 | CH₂CH₂SOCH₃ | SO₂Me | OCF₃ | |
| 4-897 | CH₂CH₂SO₂CH₃ | SO₂Me | OCF₃ | |
| 4-898 | CH₂CH₂SCH₂CH₃ | SO₂Me | OCF₃ | |
| 4-899 | CH₂CH₂SOCH₂CH₃ | SO₂Me | OCF₃ | |
| 4-900 | CH₂CH₂SO₂CH₂CH₃ | SO₂Me | OCF₃ | |
| 4-901 | CH₂CH₂SCF₃ | SO₂Me | OCF₃ | |
| 4-902 | CH₂CH₂SOCF₃ | SO₂Me | OCF₃ | |

TABLE 4-continued

| Compound No. | $R^3$ | $R^4$ | $R^5$ | Physical property |
|---|---|---|---|---|
| 4-903 | $CH_2CH_2SO_2CF_3$ | $SO_2Me$ | $OCF_3$ | |
| 4-904 | $CH_2Ph$ | $SO_2Me$ | $OCF_3$ | |
| 4-905 | $CH_2C\equiv CH$ | $SO_2Me$ | $OCF_3$ | |
| 4-906 | $CH_2C\equiv CCH_3$ | $SO_2Me$ | $OCF_3$ | |
| 4-907 | $CH_2C\equiv N$ | $SO_2Me$ | $OCF_3$ | |
| 4-908 | $CH_2CH=CH_2$ | $SO_2Me$ | $OCF_3$ | |
| 4-909 | $CH_2CH=CHCH_3$ | $SO_2Me$ | $OCF_3$ | |
| 4-910 | $CH_2CH=C(CH_3)_3$ | $SO_2Me$ | $OCF_3$ | |
| 4-911 | $CH_2OCH_3$ | $SO_2Me$ | $OCF_3$ | |
| 4-912 | $CH_2CH_2OCH_3$ | $SO_2Me$ | $OCF_3$ | |
| 4-913 | $CH_2OCH_2CH_3$ | $SO_2Me$ | $OCF_3$ | |
| 4-914 | $CH_2CH_2OCH_2CH_3$ | $SO_2Me$ | $OCF_3$ | |
| 4-915 | $CH_2CF_3$ | H | $SO_2CF_3$ | NMR |
| 4-916 | $CH_2CHF_2$ | H | $SO_2CF_3$ | |

TABLE 5

| Compound No. | $^1$H-NMR data (CDCl$_3$) |
|---|---|
| 1-50 | δ 9.07 (d, 1H), 8.75 (d, 1H), 8.61 (d, 1H), 8.30 (d, 1H), 7.27 (s, 1H), 4.10 (q, 2H), 3.88 (s, 3H), 3.84 (q, 2H), 3.18 (s, 3H), 1.38 (t, 3H) |
| 1-89 | δ 9.08 (d, 1H), 8.75 (d, 1H), 8.56 (d, 1H), 8.30 (d, 1H), 7.37 (s, 1H), 5.90 (t, 1H), 4.06 (q, 2H), 3.88 (s, 3H), 3.85 (q, 2H), 3.63 (q, 2H), 1.38 (t, 3H), 1.27 (t, 3H) |

The insecticide comprising the compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, termites, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*;

the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorios, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae,*

*Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigones, Clovia punctata, Empoasca* spp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa aceta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Meatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorqps oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus* Forskal, *Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;* the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glypto-* termes kodamai, Glyptotermes satsumensis, Cryptotermes domesticus, Odontotermes formosanus, Glyptotermes nakajimai, Pericapritermes nitobei and Reticulitermes speratus;

the species of the order Blattodea such as Periplaneta fuliginosa, Blattella germanica, Blatta orientalis, Periplaneta brunnea, Blattella lituricollis, Periplaneta japonica and Periplaneta americana;

the species of the order Siphonaptera such as Pulex irritans, Ctenocephalides felis and Ceratophyllus gallinae;

the species of the phylum Nematoda such as Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus and Tylenchus semipenetrans; and the species of the phylum Mollusca such as Pomacea canaliculata, Achatina fulica, Meghimatium bilineatum, Lehmannina valentiana, Limax flavus and Acusta despecta sieboldiana.

In addition, the insecticide of the present invention has a strong insecticidal effect on Tuta absoluta as well.

Further, mites and ticks parasitic on animals are also included in the target pests, and the examples include the species of the family Ixodidae such as Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus and Dermacentor taiwanesis; Dermanyssus gallinae; the species of the genus Ornithonyssus such as Ornithonyssus sylviarum and Ornithonyssus bursa; the species of the family Trombiculidae such as Eutrombicula wichmanni, Leptotrombidium akamushi, Leptotrombidium pallidum, Leptotrombidium fuji, Leptotrombidium Cosa, Neotrombicula autumnalis, Eutrombicula alfreddugesi and Helenicula miyagawai; the species of the family Cheyletidae such as Cheyletiella yasguri, Cheyletiella parasitivorax and Cheyletiella blakei; the species of the superfamily Sarcoptoidea such as Psoroptes cuniculi, Chorioptes bovis, Otodectes cynotis, Sarcoptes scabiei and Notoedres cati; and the species of the family Demodicidae such as Demodex canis.

Other target pests include fleas including ectoparasitic wingless insects belonging to the order Siphonaptera, more specifically, the species belonging to the families Pulicidae and Ceratophyllidae. Examples of the species belonging to the family Pulicidae include Ctenocephalides canis, Ctenocephalides felis, Pulex irritans, Echidnophaga gallinacea, Xenopsylla cheopis, Leptopsylla segnis, Nosopsyllus fasciatus and Monopsyllus anisus.

Other target pests include ectoparasites, for example, the species of the suborder Anoplura such as Haematopinus eurysternus, Haematopinus asini, Dalmalinia ovis, Linognathus vituli, Haematopinus suis, Phthirus pubis and Pediculus capitis; the species of the suborder Mallophaga such as Trichodectes canis; and hematophagous Dipteran insect pests such as Tabanus trigonus, Culicoides schultzei and Simulium ornatum. In addition, examples of endoparasites include nematodes such as lungworms, whipworms, nodular worms, endogastric parasitic worms, ascarides and filarial worms; cestodes such as Spirometra erinacei, Diphyllobothrium latum, Dipylidium caninum, Multiceps multiceps, Echinococcus granulosus and Echinococcus multilocularis; trematodes such as Schistosoma japonicum and Fasciola hepatica; and protozoa such as coccidia, Plasmodium, intestinal Sarcocystis, Toxoplasma and Cryptosporidium.

The insecticide comprising the compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the insecticide utilizes so-called penetration and translocation. That is, nursery soil, soil in transplanting holes, plant foot, irrigation water, cultivation water in hydroponics, or the like is treated with the insecticide to allow crops, ornamental flowering plants, etc. to absorb the compound of the present invention through the roots via soil or otherwise.

Examples of useful plants to which the insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., Abies sachalinensis, Picea jezoensis, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The insecticide of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the insecticide of the present invention can be used in combination or used systematically.

In order to control target pests, the insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The insecticide of the present invention is commonly used as a formulation convenient for application, which is prepared in the usual method for preparing agrochemical formulations.

That is, the compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran (THF); aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the insecticide of the present invention can be adjusted as needed, and basically, the amount of the active ingredient compound is appropriately selected from the range of 0.01 to 90 parts by weight in 100 parts by weight of the insecticide. For example, in the case where the insecticide is a dust, a granule, an emulsifiable concentrate or a wettable powder, it is suitable that the amount of the active ingredient compound is 0.01 to 50 parts by weight (0.01 to 50% by weight relative to the total weight of the insecticide).

The application rate of the insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the insecticide of the present invention can be used after mixed with other insecticides, acaricides, nematicides, microbicides, biopesticides and/or the like. Further, the insecticide can be used after mixed with herbicides, plant growth regulators, fertilizers and/or the like depending on the situation.

Examples of such additional insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, prothiophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, diallate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor,* avirulent *Erwinia carotovora* and *Bacillus subtilis*; and biopesticides used as a herbicide, such as *Xanthomonas campestris*. Such a combined use of the insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Production Example 1

Production Method of 2-(3-ethylsulfonyl-5-(2,2,2-trifluoroethyl)hydrazonylpyridin-2-yl)-3-methyl-6-trifluoromethyl-3H-imidazo[4,5-b]pyridine (Compound Number 1-9)

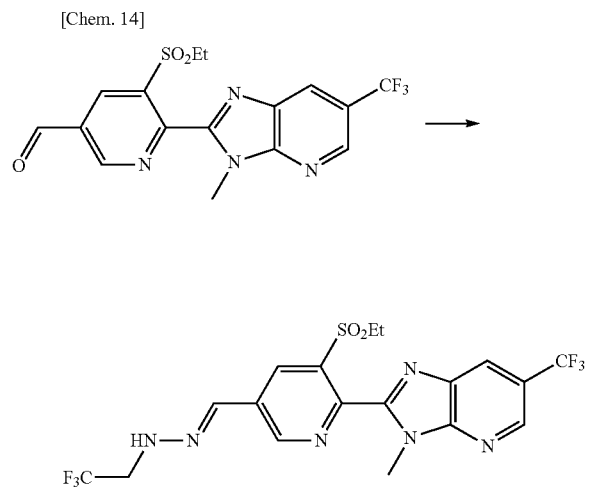

To a chloroform solution (1 mL) of 2-(3-ethylsulfonyl-5-formylpyridin-2-yl)-3-methyl-6-trifluoromethyl-3H-imidazo[4,5-b]pyridine (0.60 g), 2,2,2-trifluoroethyl hydrazine (0.02 mL) and acetic acid (0.015 mL) were added, and the mixture was stirred at room temperature for 4 hours. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.56 g).

Yield: 76%

Production Example 2

Production Method of 2-(3-ethylsulfonyl-5-{acetyl (2,2,2-trifluoroethyl)hydrazonyl}pyridin-2-yl)-3-methyl-6-trifluoromethyl-3H-imidazo[4,5-b]pyridine (Compound Number 1-124)

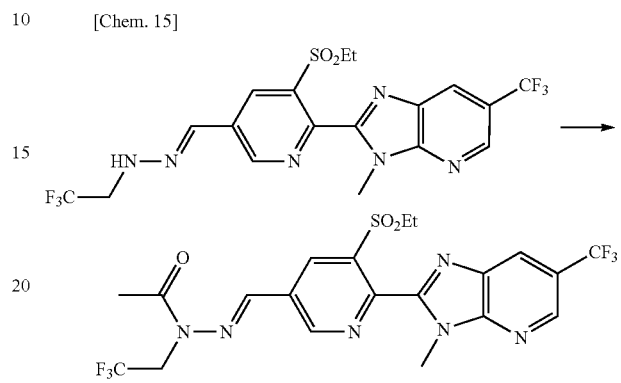

To a chloroform solution (1 mL) of 2-(3-ethylsulfonyl-5-(2,2,2-trifluoroethyl)hydrazonylpyridin-2-yl)-3-methyl-6-trifluoromethyl-3H-imidazo[4,5-b]pyridine (0.30 g), triethylamine (0.045 mL) and acetyl chloride (0.015 mL) were added, and the mixture was stirred at 50° C. for 2 hours. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.32 g).

Yield: 98%

Production Example 3

Production Method of 2-(3-ethylsulfonyl-5-{ethyl(2,2,2-trifluoroethyl)hydrazonyl}pyridin-2-yl)-3-methyl-6-trifluoromethyl-3H-imidazo[4,5-b]pyridine (Compound Number 1-118)

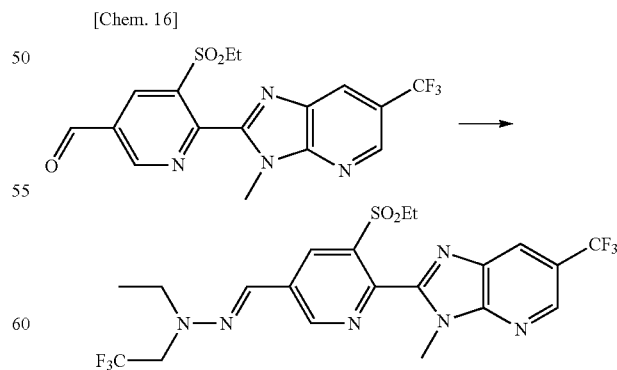

To a CHCl$_3$ solution (1 mL) of 2-(3-ethylsulfonyl-5-formylpyridin-2-yl)-3-methyl-6-trifluoromethyl-3H-imidazo[4,5-b]pyridine (0.04 g), 1-ethyl-1-(2,2,2-trifluoroethyl)hydrazine (0.021 g) and acetic acid (0.010 mL) were added, and the mixture was stirred at room temperature for 1 hour. After the completion of the reaction, water was added, and chloroform extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.038 g).

Yield: 72%

Production Example 4

Production Method of 2-(3-ethylsulfonyl-5-{methyl (2,2,2-trifluoroethyl)hydrazonyl}pyridin-2-yl)-3-methyl-6-trifluoromethyl-3H-imidazo[4,5-b]pyridine (Compound Number 1-116)

[Chem. 17]

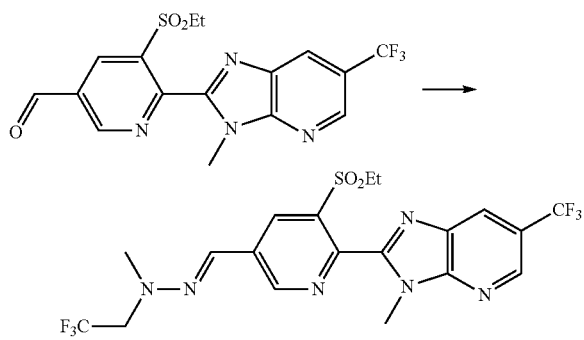

To a chloroform solution (1 mL) of 2-(3-ethylsulfonyl-5-formylpyridin-2-yl)-3-methyl-6-trifluoromethyl-3H-imidazo[4,5-b]pyridine (0.04 g), which was produced by the production method described in Reference Example 3 below, 1-methyl-1-(2,2,2-trifluoroethyl)hydrazine hydrochloride (0.024 g) and pyridine (0.012 mL) were added, and the mixture was stirred at room temperature for 1 hour. After the completion of the reaction, water was added, and chloroform extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.050 g).

Yield: 98%

Production Example 5

Production Method of 2-[3-ethylsulfonyl-5-{(2,2,2-trifluoroethyl)hydrazonyl}pyridin-2-yl]-5-(trifluoromethylthio)benzo[d]oxazole (Compound Number 2-9)

[Chem. 18]

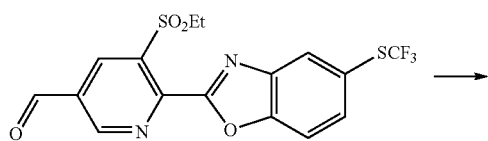

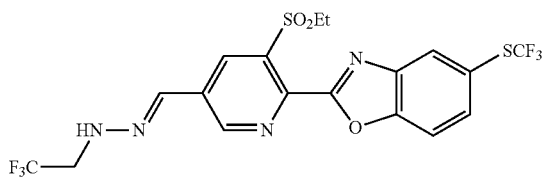

To a chloroform solution (1 mL) of 2-(3-ethylsulfonyl-5-formylpyridin-2-yl)-5-(trifluoromethylthio)benzo[d]oxazole (0.60 g), 2,2,2-trifluoroethyl hydrazine (0.02 mL) and acetic acid (0.015 mL) were added, and the mixture was stirred at room temperature for 4 hours. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.66 g).

Yield: 89%

Production Example 6

Production Method of 2-[3-ethylsulfonyl-5-{acetyl (2,2,2-trifluoroethyl)hydrazonyl}pyridin-2-yl]-5-(trifluoromethylthio)benzo[d]oxazole (Compound Number 2-124)

[Chem. 19]

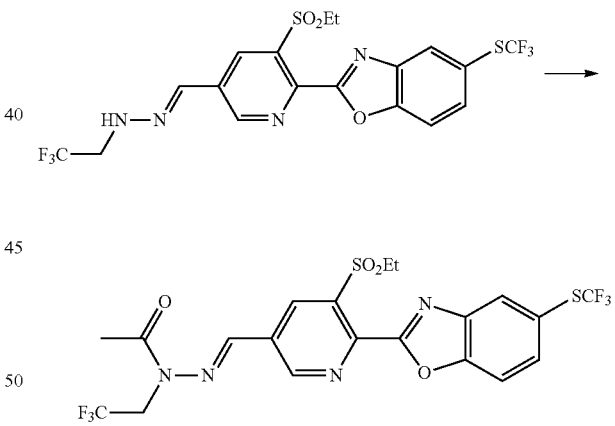

To a chloroform solution (1 mL) of 5-ethylsulfonyl-6-{5-(trifluoromethylthio)benzo[d]oxazol-2-yl}nicotinaldehyde (2,2,2-trifluoroethyl)hydrazone (0.30 g), triethylamine (0.045 mL) and acetyl chloride (0.015 mL) were added, and the mixture was stirred at 50° C. for 2 hours. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.27 g).

Yield: 84%

Production Example 7

Production Method of 2-[3-ethylsulfonyl-5-{ethyl(2,2,2-trifluoroethyl)hydrazonyl}pyridin-2-yl]-5-(trifluoromethylthio)benzo[d]oxazole (Compound Number 2-118)

[Chem. 20]

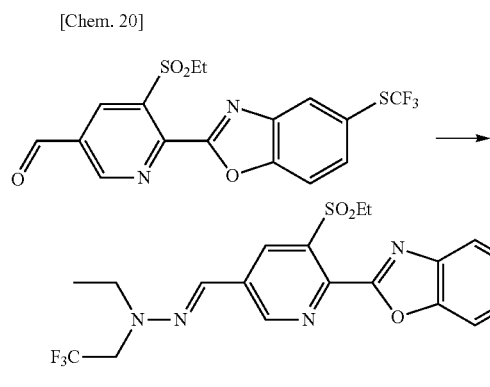

The title compound (0.0207 g) was obtained from 2-(3-ethylsulfonyl-5-formylpyridin-2-yl)-5-(trifluoromethylthio)benzo[d]oxazole (0.04 g) by the production method described in Production Example 3.

Yield: 52%

Production Example 8

Production Method of 2-[3-ethylsulfonyl-5-{methyl(2,2,2-trifluoroethyl)hydrazonyl}pyridin-2-yl]-5-(trifluoromethylthio)benzo[d]oxazole (Compound Number 2-116)

[Chem. 21]

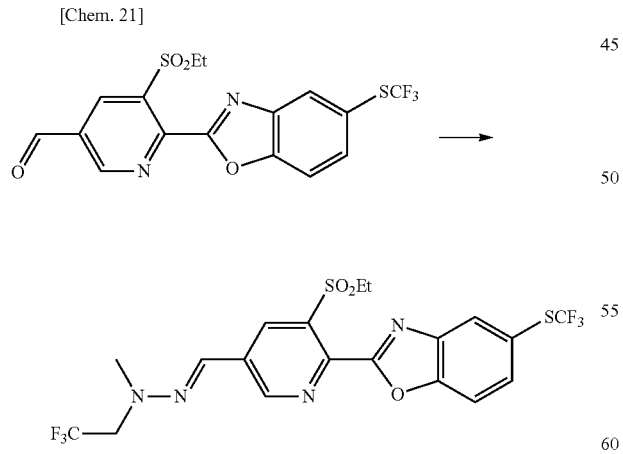

The title compound (0.040 g) was obtained from 2-(3-ethylsulfonyl-5-formylpyridin-2-yl)-5-(trifluoromethylthio)benzo[d]oxazole (0.04 g) by the production method described in Production Example 4.

Yield: 80%

Production Example 9

Production Method of 2-(3-ethylsulfonyl-6-(2,2,2-trifluoroethyl)hydrazonylpyridin-2-yl)-3-methyl-6-trifluoromethyl-3H-imidazo[4,5-b]pyridine

[Chem. 22]

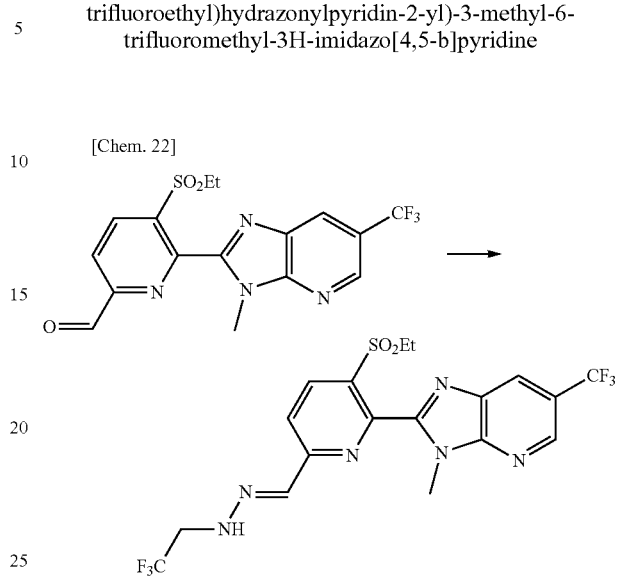

2-(3-Ethylsulfonyl-6-formylpyridin-2-yl)-3-methyl-6-trifluoromethyl-3H-imidazo[4,5-b]pyridine (0.06 g) was reacted according to the production method described in Production Example 1 above to give the title compound (0.037 g).

Yield: 50%

Production Example 10

2-{3-Ethylsulfonyl-6-(2,2,2-trifluoroethylhydrazonyl)pyridin-2-yl}-5-(trifluoromethylthio)benzo[d]oxazole

[Chem. 23]

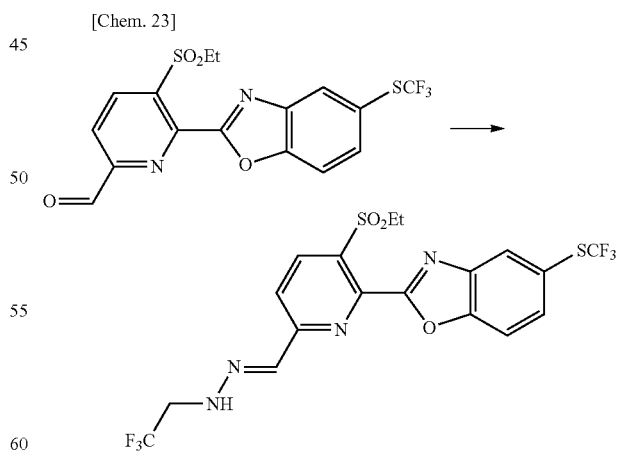

2-(3-Ethylsulfonyl-6-formylpyridin-2-yl)-5-(trifluoromethylthio)benzo[d]oxazole (0.13 g) was reacted according to the production method described in Production Example 1 above to give the title compound (0.11 g).

Yield: 69%

Intermediate Production Example 1

Production Method of 5-chloro-6-ethoxycarbonylpyridine-3-carboxylic acid

[Chem. 24]

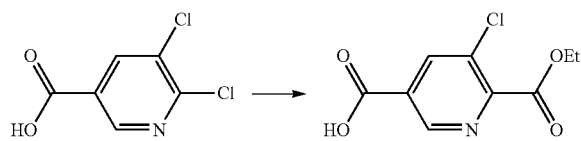

An autoclave was charged with an ethanol (60 mL) solution of 5,6-dichloropyridine-3-carboxylic acid (10 g, 52 mmol). To this, DPPB (1,4-bis(diphenylphosphino)butane) (2.2 g, 10 mol %), triethylamine (14 g, 2.5 Eq) and $PdCl_2$ $(PPh_3)_2$ (911 mg, 2.5 mol %) were added. The atmosphere in the reaction system was replaced with carbon monoxide (CO pressure, 4.0 MPa), and the mixture was stirred at 135° C. for 4 hours. To the reaction mixture, water and 3 N hydrochloric acid were added to acidify the aqueous layer, and ethyl acetate extraction was performed several times. The organic layer was dried over sodium sulfate and then concentrated. The resulting solid was washed with a hexane-ethyl acetate (2:1 (v/v)) mixture to give the desired compound, i.e., 5-chloro-6-ethoxycarbonylpyridine-3-carboxylic acid (10.9 g).

Yield: 76%

Physical property: $^1$H-NMR ($CDCl_3$) δ 9.02 (d, 1H), 8.44 (d, 1H), 4.42 (dd, 2H), 1.33 (t, 3H)

Intermediate Production Example 2

Production Method of 5-chloro-6-ethoxycarbonylpyridine-3-carboxylic acid t-butyl ester

[Chem. 25]

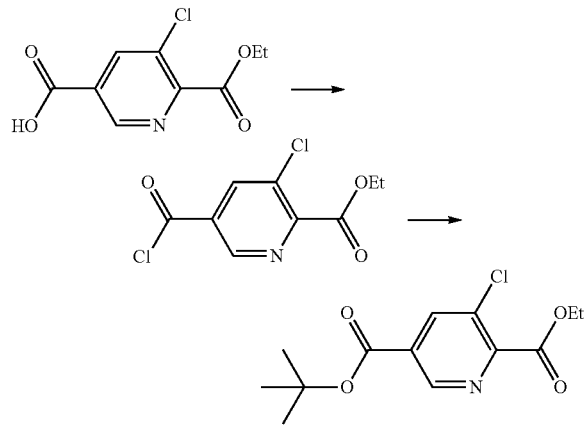

The 5-chloro-6-ethoxycarbonylpyridine-3-carboxylic acid (10.9 g, 47.6 mmol) obtained in the previous step was dissolved in toluene (30 mL), and DMF (dimethylformamide) (4 mL) was added to the solution. Next, thionyl chloride (11 g, 2 Eq) was added, and the mixture was heated at 90° C. with stirring for 3 hours. The reaction mixture was allowed to come to room temperature and then concentrated. In another vessel, a mixture of t-butyl alcohol (35 mL, 10 Eq), THF (tetrahydrofuran) (100 mL), diisopropylethylamine (50 mL, 7 Eq) and DMAP (N,N-dimethyl-4-aminopyridine) (6 g, 1 Eq) was prepared, and to this, the concentrated residue was slowly added under ice cooling. The reaction mixture was heated under reflux for 3 hours and then allowed to cool down to room temperature. To this, water and ethyl acetate were added, and extraction was performed several times. The organic layer was dried over sodium sulfate and then concentrated. The residue was subjected to column chromatography (hexane-AcOEt (acetic acid ethyl ester)=5:1 (v/v)) to give the desired compound, i.e., 5-chloro-6-ethoxycarbonylpyridine-3-carboxylic acid t-butyl ester (8.43 g).

Yield: 62%

Physical property: $^1$H-NMR ($CDCl_3$) δ 9.05 (d, 1H), 8.30 (d, 1H), 4.50 (dd, 2H), 1.61 (s, 9H), 1.44 (t, 3H)

Intermediate Production Example 3

Production Method of 5-ethylthio-6-ethoxycarbonylpyridine-3-carboxylic acid t-butyl ester

[Chem. 26]

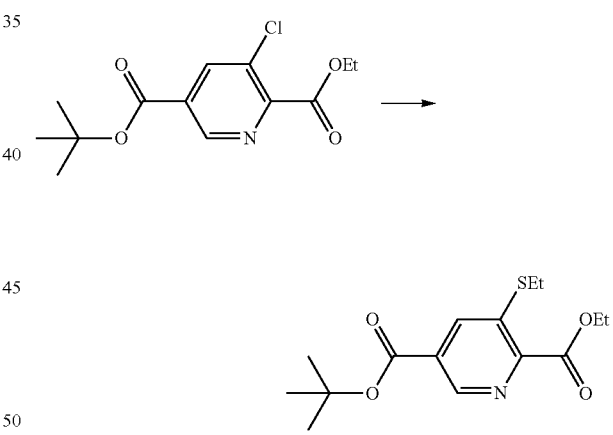

5-Chloro-6-ethoxycarbonylpyridine-3-carboxylic acid t-butyl ester (8.43 g, 21.65 mmol) was dissolved in DMF (100 mL). Sodium ethanethiolate (2.27 g, 1 Eq) was slowly added to the solution under ice cooling, and the mixture was stirred for 5 minutes. To this, water and 0.5 N hydrochloric acid were successively added. After ethyl acetate extraction was performed several times, the organic layer was dried over sodium sulfate and then concentrated. The residue was subjected to column chromatography (hexane-AcOEt=5:1 (v/v)) to give the desired compound, i.e., 5-ethylthio-6-ethoxycarbonylpyridine-3-carboxylic acid t-butyl ester (6.17 g).

Yield: 92%

Physical property: $^1$H-NMR (CDCl$_3$) δ 8.91 (d, 1H), 8.22 (d, 1H), 4.49 (dd, 2H), 2.99 (dd, 2H), 1.61 (s, 9H), 1.45 (t, 3H), 1.40 (t, 3H)

Intermediate Production Example 4

Production Method of 3-ethylthio-5-t-butoxycarbonylaminopyridine-2-carboxylic acid ethyl ester

[Chem. 27]

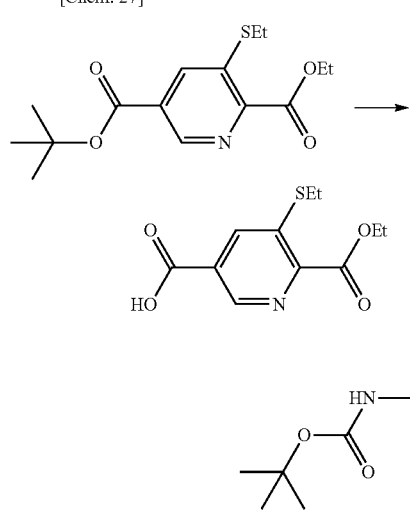

5-Ethylthio-6-ethoxycarbonylpyridine-3-carboxylic acid t-butoxy ester (6.17 g, 19.9 mmol) was dissolved in trifluoroacetic acid (30 mL), and the solution was heated under reflux for 30 minutes. The reaction mixture was concentrated, toluene and ethyl acetate were added to the residue, and the mixture was concentrated again. To the residue, t-butyl alcohol (100 mL), triethylamine (6.5 g, 3 Eq) and DPPA (diphenylphosphoryl azide) (11.74 g, 2 Eq) were added, and the mixture was stirred at room temperature for 1 hour and then refluxed for 4 hours. The reaction mixture was concentrated, and the residue was subjected to column chromatography (hexane-ethyl acetate=2:1 (v/v)) to give the desired compound, i.e., 3-ethylthio-5-t-butoxycarbonylaminopyridine-2-carboxylic acid ethyl ester (3.63 g).

Yield: 56%

Physical property: $^1$H-NMR (CDCl$_3$) δ 8.25 (d, 1H), 8.09 (d, 1H), 6.74 (s, 1H), 4.46 (dd, 2H), 2.97 (dd, 2H), 1.53 (s, 9H), 1.44 (t, 3H), 1.41 (t, 3H)

Intermediate Production Example 5

Production Method of 5-amino-3-ethylthiopyridine-2-carboxylic acid ethyl ester

[Chem. 28]

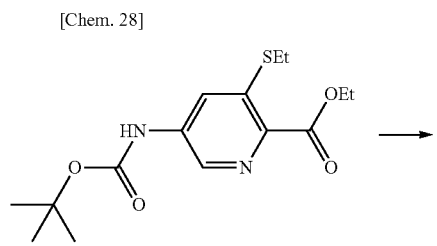

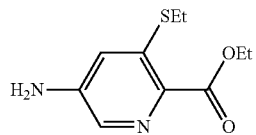

3-Ethylthio-5-t-butoxycarbonylaminopyridine-2-carboxylic acid ethyl ester (670 mg, 2.06 mmol) was dissolved in trifluoroacetic acid (30 mL), and the solution was stirred at room temperature for 30 minutes. The reaction mixture was concentrated, and water, ethyl acetate and potassium carbonate were added to the residue. After ethyl acetate extraction was performed several times, the organic layer was dried over sodium sulfate and then concentrated. The residue was subjected to column chromatography (hexane-AcOEt=1:3 (v/v)) to give the desired compound, i.e., 5-amino-3-ethylthiopyridine-2-carboxylic acid ethyl ester (358 mg).

Yield: 77%

Physical property: $^1$H-NMR (CDCl$_3$) δ 7.89 (d, 1H), 6.80 (s, 1H), 4.43 (dd, 2H), 4.08 (s, 2H), 2.88 (dd, 2H), 1.56 (s, 9H), 1.42 (t, 3H), 1.40 (t, 3H)

Intermediate Production Example 6

Production Method of 3-ethylthio-5-iodopyridine-2-carboxylic acid ethyl ester

[Chem. 29]

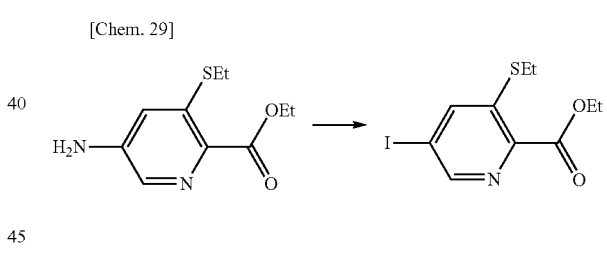

5-Amino-3-ethylthiopyridine-2-carboxylic acid ethyl ester (1 g, 4.44 mmol) was dissolved in acetonitrile (10 mL). To the solution, trifluoroacetic acid (500 mg, 1 Eq) and p-toluenesulfonic acid (2.6 g, 3 Eq) were added, and the mixture was cooled in a water bath at about 5° C. To the reaction mixture, an aqueous solution (10 mL) of potassium iodide (2.25 g, 3 Eq) and sodium nitrite (612 mg, 2 Eq) prepared in another vessel was slowly added. The mixture was stirred for 30 minutes and further stirred at room temperature for 30 minutes. To the reaction mixture, an aqueous "hypo" (sodium hyposulfite) solution was added. After ethyl acetate extraction was performed several times, the organic layer was dried and then concentrated. The residue was subjected to column chromatography to give the desired compound, i.e., 3-ethylthio-5-iodopyridine-2-carboxylic acid ethyl ester (761 mg).

Yield: 51%

Physical property: $^1$H-NMR (CDCl$_3$) δ 8.61 (s, 1H), 7.95 (s, 1H), 4.45 (dd, 2H), 2.91 (dd, 2H), 1.43 (t, 3H), 1.39 (t, 3H)

Intermediate Production Example 7

Production Method of 5-ethylthio-6-ethoxycarbonylpyridine-3-carboxylic acid

[Chem. 30]

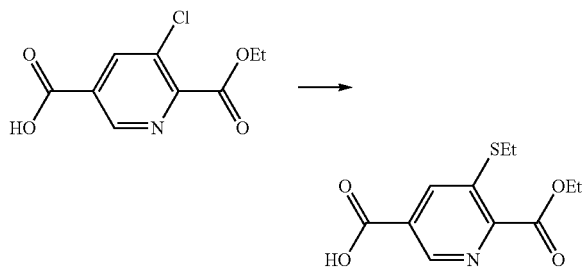

To a DMF solution (210 mL) of the 5-chloro-6-ethoxycarbonylpyridine-3-carboxylic acid (9.7 g) synthesized according to the production method of Intermediate Production Method 1 above, sodium hydride (5.1 g) and ethylmercaptan (3.2 mL) were added at 0° C., and the mixture was stirred at room temperature for 2 hours. After the completion of the reaction, the reaction mixture was slowly added to a 1 M hydrochloric acid solution (300 mL) at 0° C. until the pH reached 3. Ethyl acetate extraction was performed, and the organic layer was washed with a saturated aqueous sodium chloride solution. The washed organic layer was dried over anhydrous magnesium sulfate and then dried in vacuo. MTBE (methyl tert-butyl ether) was added to the residue, and the resulting solid was collected by filtration. Thus, the title compound (8.1 g) was obtained.
Yield: 75%

Intermediate Production Example 8

Production Method of 3-ethylthio-5-hydroxymethylpyridine-2-carboxylic acid ethyl ester

[Chem. 31]

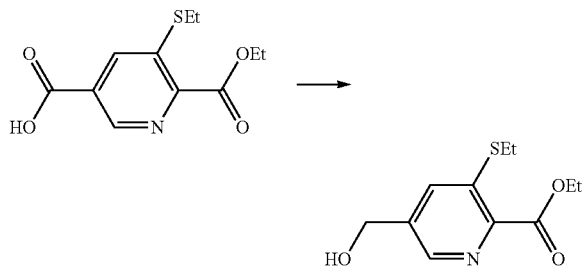

To a THF solution (100 mL) of 5-ethylthio-6-ethoxycarbonylpyridine-3-carboxylic acid (10 g), CDI (carbonyldiimidazole) (10 g) was added, and the mixture was stirred at room temperature for 2 hours. This THF solution was slowly added to 100 mL of an aqueous solution of NaBH$_4$ (5.5 g) at 0° C., and the mixture was stirred at room temperature for 1 hour. After the completion of the reaction, a 4 M hydrochloric acid solution was added to adjust the pH to 2, and ethyl acetate extraction was performed. The organic layer was washed with a saturated aqueous sodium chloride solution, dried over anhydrous magnesium sulfate, and concentrated in vacuo. The residue was purified by silica gel chromatography to give 3-ethylthio-5-hydroxymethylpyridine-2-carboxylic acid ethyl ester (6.4 g).
Yield: 62%

Intermediate Production Example 9

Production Method of 3-ethylthio-5-methoxymethoxymethylpyridine-2-carboxylic acid ethyl ester

[Chem. 32]

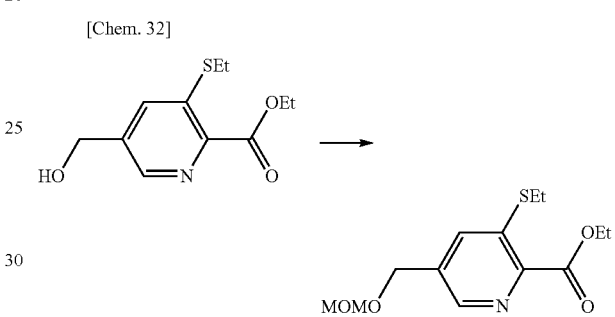

To a CHCl$_3$ solution (50 mL) of 3-ethylthio-5-hydroxymethylpyridine-2-carboxylic acid ethyl ester (6.4 g), DIPEA (N,N-diisopropylethylamine) (13.6 mL) and methoxymethyl chloride (MOMCl) (6.0 mL) were added, and the mixture was stirred at room temperature for 1 hour. After the completion of the reaction, an aqueous ammonium chloride solution was added, and ethyl acetate extraction was performed. The organic layer was washed with a saturated aqueous sodium chloride solution, dried over anhydrous magnesium sulfate, and concentrated in vacuo to give 3-ethylthio-5-methoxymethoxymethylpyridine-2-carboxylic acid ethyl ester (7.1 g).
Yield: 94%

Intermediate Production Example 10

Production Method of 1-ethyl-1-(2,2,2-trifluoroethyl)hydrazine

[Chem. 33]

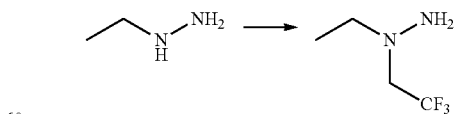

To a diethyl ether solution (6 mL) of ethylhydrazine (0.5 mL), triethylamine (0.99 mL) and 2,2,2-trifluoroethyl trifluoromethanesulfonate (0.97 mL) were added, and the mixture was stirred at room temperature for 1 hour. After the completion of the reaction, water was added, and diethyl ether extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.32 g).

Yield: 33%

Intermediate Production Example 11

Production Method of
1-ethyl-1-(methoxycarbonyl)hydrazine

[Chem. 34]

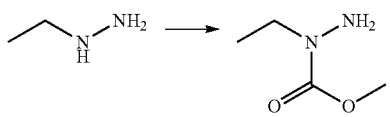

To a THF solution (6 mL) of ethylhydrazine (0.5 mL), triethylamine (0.99 mL) and methyl chloroformate (0.52 mL) were added under ice cooling, and the mixture was stirred at 0° C. for 1 hour. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give the title compound (0.37 g).

Yield: 42%

Intermediate Production Example 12

Production Method of
1-ethyl-1-(ethoxythiocarbonyl)hydrazine

[Chem. 35]

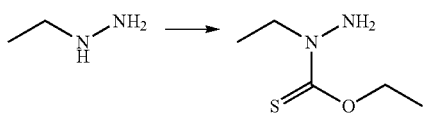

To a methanol solution (20 mL) of potassium ethylxanthogenate (2.0 g), ethylhydrazine (3.7 mL) was added, and the mixture was stirred at room temperature for 1 hour. After the completion of the reaction, the reaction mixture was dried in vacuo. The residue was purified by silica gel chromatography to give the title compound (1.2 g).

Yield: 65%

Intermediate Production Example 13

Production Method of
1-ethyl-1-(dimethylaminothiocarbonyl)hydrazine

[Chem. 36]

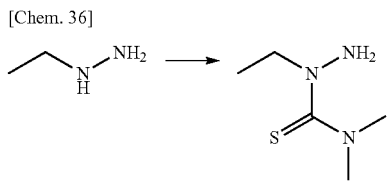

To a methanol solution (20 mL) of potassium dimethyldithiocarbamate (2.0 g), ethylhydrazine (3.3 mL) was added, and the mixture was stirred at room temperature for 1 hour. After the completion of the reaction, the reaction mixture was dried in vacuo. The residue was purified by silica gel chromatography to give the title compound (0.8 g).

Yield: 50%

Intermediate Production Example 14

Production Method of
1-ethyl-1-(ethylaminothiocarbonyl)hydrazine

[Chem. 37]

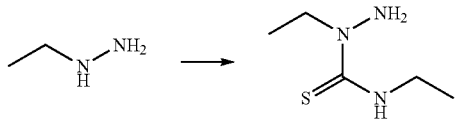

To an ethanol solution (20 mL) of ethylhydrazine (1.1 mL), ethyl isothiocyanate (1.1 mL) was added, and the mixture was stirred at room temperature for 5 hours. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. MTBE and hexane were added to the residue, and the resulting solid was collected by filtration. Thus, the title compound (0.86 g) was obtained.

Yield: 39%

Reference Example 1

Production Method of 2-(3-ethylthio-5-iodopyridin-2-yl)-3-methyl-6-trifluoromethyl-3H-imidazo[4,5-b]pyridine

[Chem. 38]

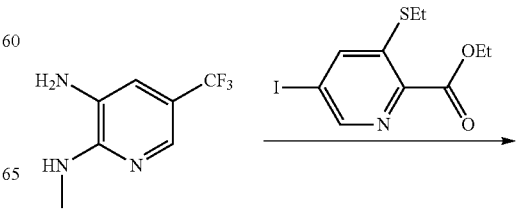

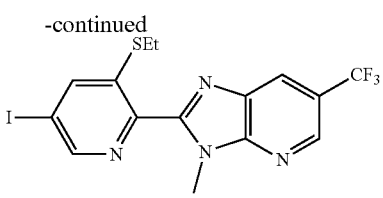

To a THF solution (15 mL) of 3-amino-2-methylamino-5-trifluoromethyl pyridine (0.71 g), a THF solution (5 mL) of sodium hydride (0.18 g) and 3-ethylthio-5-iodo-2-pyridinecarboxylic acid ethyl ester (1.25 g) was added under ice cooling. The mixture was allowed to come to room temperature and then stirred for 2 hours. After the completion of the reaction, a 1 M hydrochloric acid solution was added, and ethyl acetate extraction was performed. The organic layer was washed with a saturated aqueous sodium chloride solution. The washed organic layer was dried over anhydrous magnesium sulfate, and the solvent was evaporated off. To the residue, NMP (20 mL) and p-toluenesulfonic acid monohydrate (1.9 g) were added, and the mixture was stirred at 150° C. for 3 hours. After the completion of the reaction, a saturated aqueous sodium hydrogen carbonate solution was added, and ethyl acetate extraction was performed. The organic layer was washed with a saturated aqueous sodium chloride solution. The washed organic layer was dried over anhydrous magnesium sulfate, and the solvent was evaporated off. The residue was purified by silica gel chromatography to give 2-(3-ethylthio-5-iodopyridin-2-yl)-3-methyl-6-trifluoromethyl-3H-imidazo[4,5-b]pyridine (1.52 g).

Yield: 89%

Reference Example 2

Production Method of 2-(3-ethylthio-5-vinylpyridin-2-yl)-3-methyl-6-trifluoromethyl-3H-imidazo[4,5-b]pyridine

[Chem. 39]

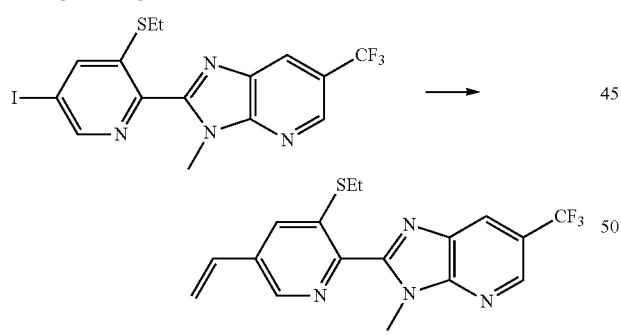

To a DME/H$_2$O (4:1 (v/v)) solution (20 mL) of the 2-(3-ethylthio-5-iodopyridin-2-yl)-3-methyl-6-trifluoromethyl-3H-imidazo[4,5-b]pyridine (1.52 g) produced in the production method described above, potassium vinyltrifluoroborate (0.44 g), PdCl$_2$ (dppf)·acetone (0.13 g) and cesium carbonate (2.1 g) were added, and the mixture was heated under reflux for 2 hours. After the completion of the reaction, the reaction mixture was dried in vacuo. The residue was purified by silica gel chromatography to give 2-(3-ethylthio-5-vinylpyridin-2-yl)-3-methyl-6-trifluoromethyl-3H-imidazo[4,5-b]pyridine (0.85 g).

Yield: 71%

The abbreviation dppf stands for 1,1'-bis(diphenylphosphino)ferrocene.

Reference Example 3

Production Method of 2-(3-ethylsulfonyl-5-formylpyridin-2-yl)-3-methyl-6-trifluoromethyl-3H-imidazo[4,5-b]pyridine

[Chem. 40]

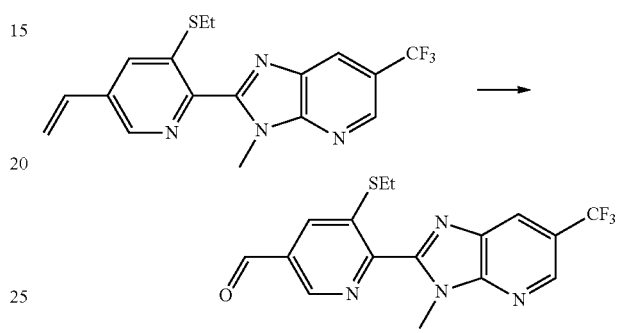

To a THF/aqueous pH 7 buffer (2:1 (v/v)) solution (20 mL) of 2-(3-ethylthio-5-vinylpyridin-2-yl)-3-methyl-6-trifluoromethyl-3H-imidazo[4,5-b]pyridine (0.85 g), NMO (N-methylmorpholine N-oxide) (1.64 g, 50% in H$_2$O) and osmium tetroxide (6.0 mL, 0.039 M in t-BuOH) were added, and the mixture was stirred at room temperature overnight. To this, sodium periodate (1.5 g) was added, and the mixture was stirred at room temperature for 2 hours. After the completion of the reaction, a saturated sodium thiosulfate solution was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give 2-(3-ethylsulfonyl-5-formylpyridin-2-yl)-3-methyl-6-trifluoromethyl-3H-imidazo[4,5-b]pyridine (0.54 g).

Yield: 86%

Reference Example 4

Production Method of N-(2-hydroxy-5-(trifluoromethylthio)phenyl)-3-ethylthio-5-(methoxymethoxymethyl)-2-pyridinecarboxylic acid amide

[Chem. 41]

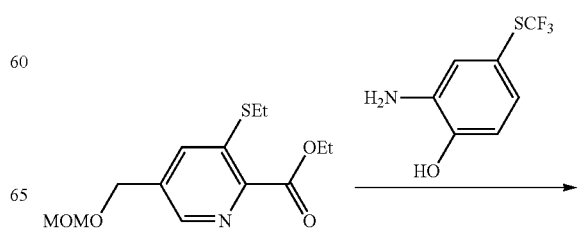

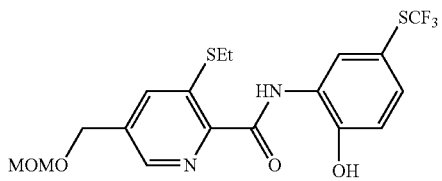

To a THF solution (10 mL) of 3-ethylthio-5-(methoxymethoxymethyl)-2-pyridinecarboxylic acid ethyl ester (0.64 g), sodium hydride (0.36 g) and a THF solution (2 mL) of 2-amino-4-(trifluoromethylthio)phenol (0.4 g) were added at 0° C., and the mixture was stirred at 50° C. for 2 hours. After the completion of the reaction, a saturated aqueous ammonium chloride solution was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give N-(2-hydroxy-5-(trifluoromethylthio)phenyl)-3-ethylthio-5-(methoxymethoxymethyl)-2-pyridinecarboxylic acid amide (0.73 g).

Yield: 60%

Reference Example 5

Production Method of 2-(3-ethylthio-5-(methoxymethoxymethyl)pyridin-2-yl)-5-(trifluoromethylthio)benzo[d]oxazole

[Chem. 42]

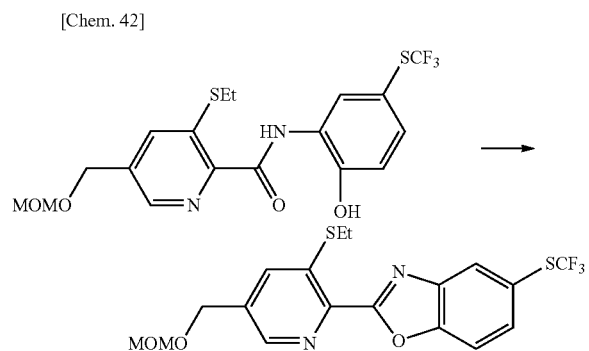

To a THF solution (5 mL) of N-(2-hydroxy-5-(trifluoromethylthio)phenyl)-3-ethylthio-5-(methoxymethoxymethyl)-2-pyridinecarboxylic acid amide (0.73 g), triphenylphosphine (1.04 g) and bis(2-methoxyethyl) azodicarboxylate (0.93 g) were added, and the mixture was stirred at 60° C. for 1 hour. After the completion of the reaction, water was added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give 2-(3-ethylthio-5-(methoxymethoxymethyl)pyridin-2-yl)-5-(trifluoromethylthio)benzo[d]oxazole (0.70 g).

Yield: quantitative

Reference Example 6

Production Method of 2-(3-ethylsulfonyl-5-(methoxymethoxymethyl)pyridin-2-yl)-5-(trifluoromethylthio) benzo [d]oxazole

[Chem. 43]

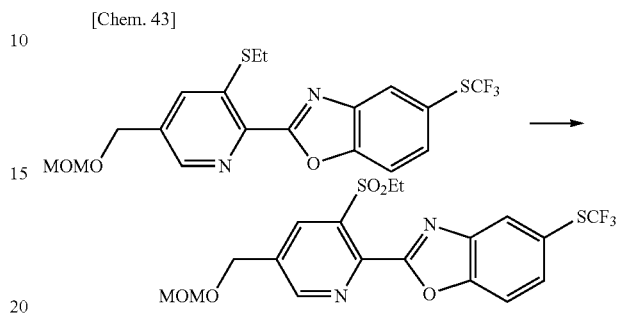

To an ethyl acetate solution (15 mL) of 2-(3-ethylthio-5-(methoxymethoxymethyl)pyridin-2-yl)-5-(trifluoromethylthio)benzo[d]oxazole (0.68 g), m-chloroperoxybenzoic acid (0.74 g) was added at room temperature, and the mixture was stirred for 2 hours. After the completion of the reaction, a saturated aqueous sodium hydrogen carbonate solution and a saturated aqueous sodium thiosulfate solution were added, and ethyl acetate extraction was performed. The organic layer was washed with a saturated aqueous sodium chloride solution. The washed organic layer was dried over anhydrous magnesium sulfate and then dried in vacuo. The residue was purified by silica gel chromatography to give 2-(3-ethylsulfonyl-5-(methoxymethoxymethyl)pyridin-2-yl)-5-(trifluoromethylthio)benzo[d]oxazole (0.40 g).

Yield: 60%

Reference Example 7

Production Method of 2-(3-ethylsulfonyl-5-(hydroxymethyl)pyridin-2-yl)-5-(trifluoromethylthio) benzo[d]oxazole

[Chem. 44]

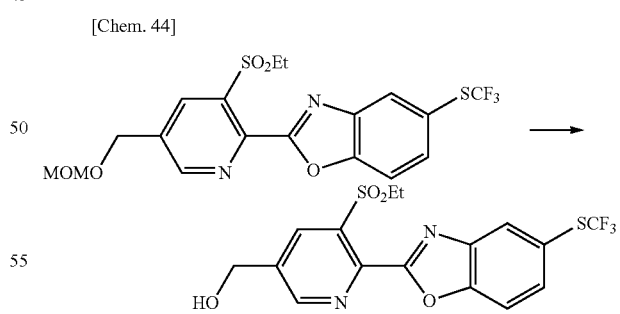

To a methanol solution (7 mL) of 2-(3-ethylsulfonyl-5-(methoxymethoxymethyl)pyridin-2-yl)-5-(trifluoromethylthio)benzo[d]oxazole (0.55 g), concentrated hydrochloric acid (2 mL) was added, and the mixture was stirred at room temperature overnight. After the completion of the reaction, the reaction mixture was dried in vacuo. A saturated aqueous sodium hydrogen carbonate solution was added to the residue, and ethyl acetate extraction was performed. The organic layer was washed with a saturated aqueous sodium chloride solution, dried over anhydrous magnesium sulfate, and concentrated in vacuo. The residue was purified by silica gel chromatography to give 2-(3-ethylsulfonyl-5-(hydroxymethyl)pyridin-2-yl)-5-(trifluoromethylthio)benzo[d]oxazole (0.34 g).

Yield: 70%

Reference Example 8

Production Method of 5-ethylsulfonyl-6-{5-(trifluoromethylthio)benzo[d]oxazol-2-yl}nicotinaldehyde

[Chem. 45]

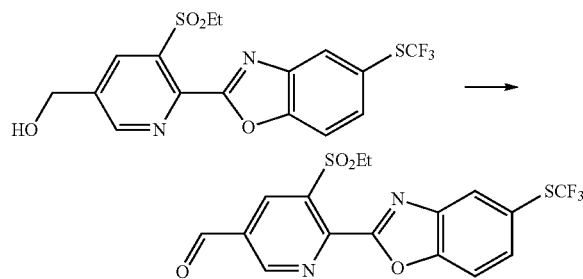

To a chloroform solution (7 mL) of 2-(3-ethylsulfonyl-5-(hydroxymethyl)pyridin-2-yl)-5-(trifluoromethylthio)benzo[d]oxazole (0.34 g), BAIB ([bis(acetoxy)iodo]benzene) (0.32 g) and TEMPO (2,2,6,6-tetramethylpiperidine 1-oxyl free radical) (0.028 g) were added, and the mixture was stirred at room temperature overnight. After the completion of the reaction, a saturated aqueous sodium thiosulfate solution was added, and ethyl acetate extraction was performed. The organic layer was washed with a saturated aqueous sodium chloride solution, dried over anhydrous magnesium sulfate, and concentrated in vacuo. The residue was purified by silica gel chromatography to give 5-ethylsulfonyl-6-(trifluoromethylthio)benzo[d]oxazol-2-yl)nicotinaldehyde (0.26 g).

Yield: 75%

Reference Example 9

Production Method of N-{2-methylamino-5-(trifluoromethyl)pyridin-3-yl}-3,6-dichloro-2-pyridinecarboxylic acid amide

[Chem. 46]

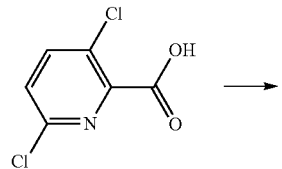

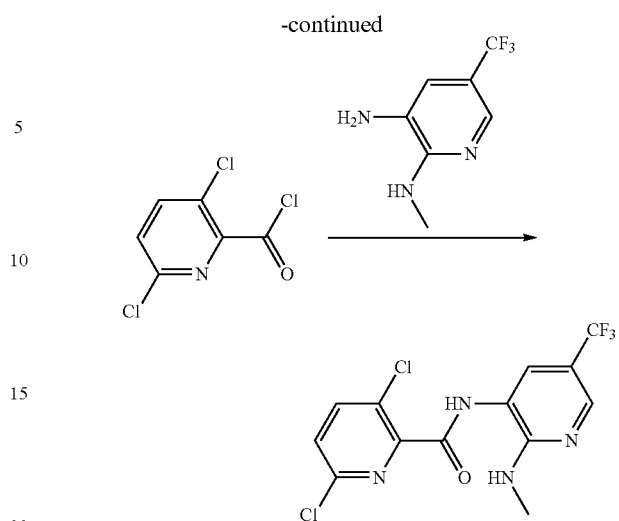

To a toluene solution (1.3 mL) of 3,6-dichloropyridine-2-carboxylic acid (0.50 g), DMF (10 μL) and thionyl chloride (490 μL) were added at room temperature, and the mixture was heated under reflux for 5 hours. After the completion of the reaction, the reaction mixture was concentrated in vacuo to give an acid chloride.

To a THF solution of 3-amino-2-methylamino-5-trifluoromethyl pyridine (0.50 g), a THF solution of the obtained acid chloride was added dropwise at 0° C. The mixture was stirred at room temperature for 5 hours, and to this, hexane was added. The precipitate was collected by filtration and then added to a saturated aqueous sodium carbonate solution, and ethyl acetate extraction was performed. The organic layer was dried over anhydrous sodium sulfate and then concentrated in vacuo to give the title compound (0.93 g).

Yield: quantitative

Reference Example 10

Production Method of 2-(3,6-dichloropyridin-2-yl)-3-methyl-6-trifluoromethyl-3H-imidazo[4,5-b]pyridine

[Chem. 47]

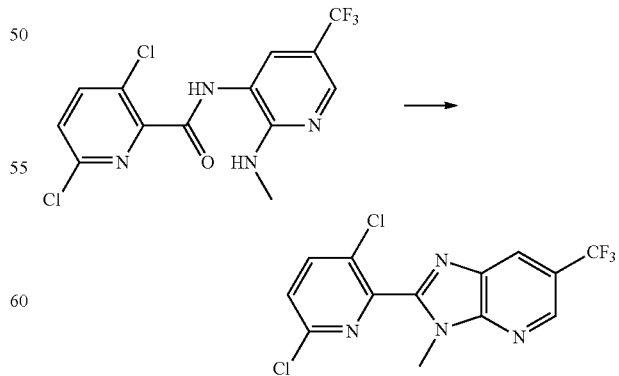

An acetic acid solution (2.6 mL) of N-{2-methylamino-5-(trifluoromethyl)pyridin-3-yl}-3,6-dichloro-2-pyridinecarboxylic acid amide (0.93 g) was stirred and heated under reflux for 4 hours. After the completion of the reaction, the reaction mixture was allowed to cool to room temperature, and water was added thereto. The precipitate was collected by filtration and dried in vacuo to give the title compound (0.75 g).

Yield: 89%

Reference Example 11

Production Method of 2-(3-ethylthio-6-chloropyridin-2-yl)-3-methyl-6-trifluoromethyl-3H-imidazo[4,5-b]pyridine

[Chem. 48]

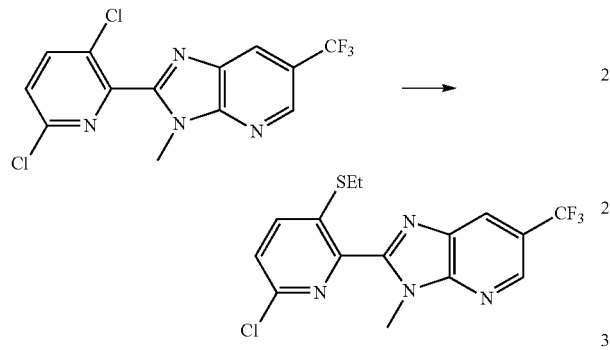

2-(3,6-Dichloropyridin-2-yl)-3-methyl-6-trifluoromethyl-3H-imidazo[4,5-b]pyridine (0.93 g) was reacted according to the production method described in Intermediate Production Example 7 above to give the title compound (0.55 g).

Yield: 63%

Reference Example 12

Production Method of 2-(3-ethylsulfonyl-6-chloropyridin-2-yl)-3-methyl-6-trifluoromethyl-3H-imidazo[4,5-b]pyridine

[Chem. 49]

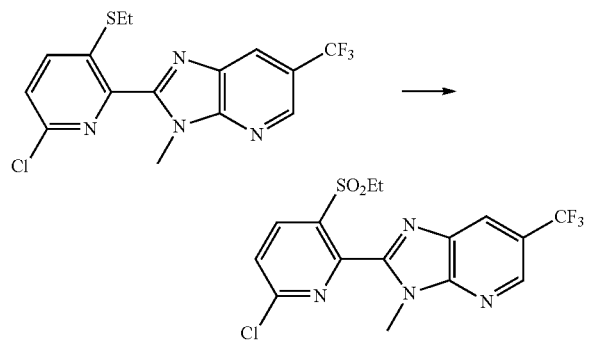

2-(3-Ethylthio-6-chloropyridin-2-yl)-3-methyl-6-trifluoromethyl-3H-imidazo[4,5-b]pyridine (0.52 g) was reacted according to the production method described in Reference Example 6 above to give the title compound (0.54 g).

Yield: 95%

Reference Example 13

Production Method of 2-(3-ethylsulfonyl-6-vinylpyridin-2-yl)-3-methyl-6-trifluoromethyl-3H-imidazo[4,5-b]pyridine

[Chem. 50]

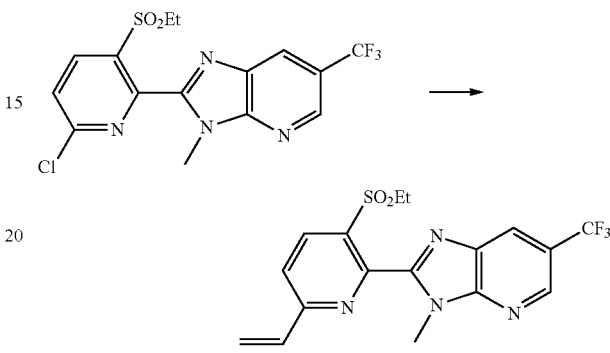

2-(3-Ethylsulfonyl-6-chloropyridin-2-yl)-3-methyl-6-trifluoromethyl-3H-imidazo[4,5-b]pyridine (0.8 g) was reacted according to the production method described in Reference Example 2 above to give the title compound (0.69 g).

Yield: 88%

Reference Example 14

Production Method of 2-(3-ethylsulfonyl-6-formylpyridin-2-yl)-3-methyl-6-trifluoromethyl-3H-imidazo[4,5-b]pyridine

[Chem. 51]

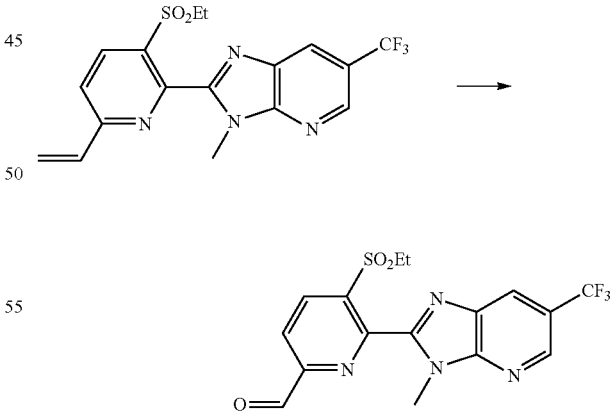

2-(3-Ethylsulfonyl-6-vinylpyridin-2-yl)-3-methyl-6-trifluoromethyl-3H-imidazo[4,5-b]pyridine (0.62 g) was reacted according to the production method described in Reference Example 3 above to give the title compound (0.55 g).

Yield: 89%

Reference Example 15

Production Method of 2-(3,6-dichloropyridin-2-yl)-5-(trifluoromethylthio)benzo[d]oxazole

[Chem. 52]

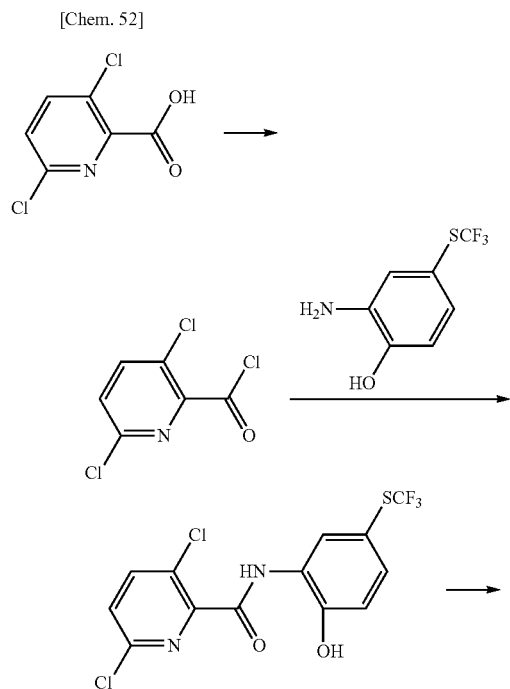

To a THF solution (20 mL) of 3,6-dichloropyridine-2-carboxylic acid (3.0 g), DMF (0.12 mL) and oxalyl chloride (1.6 mL) were added at room temperature, and the mixture was stirred for 1 hour. After the completion of the reaction, the reaction mixture was concentrated in vacuo to give an acid chloride.

To a THF solution (20 mL) of 2-amino-4-(trifluoromethylthio)phenol (3.3 g), a THF solution (20 mL) of the obtained acid chloride was added dropwise at 0° C. After the mixture was stirred at room temperature for 1 hour, a saturated sodium hydrogen carbonate solution was added, and ethyl acetate extraction was performed. The organic layer was dried over anhydrous sodium sulfate and then concentrated in vacuo. To a xylene solution (50 mL) of the residue, p-toluenesulfonic acid monohydrate (8.9 g) was added, and the mixture was stirred at 150° C. for 6 hours. After the completion of the reaction, the reaction mixture was dried in vacuo. The residue was purified by silica gel chromatography to give the title compound (2.9 g).

Yield: 51%

Reference Example 16

Production Method of 2-(3-ethylthio-6-chloropyridin-2-yl)-5-(trifluoromethylthio)benzo[d]oxazole

[Chem. 53]

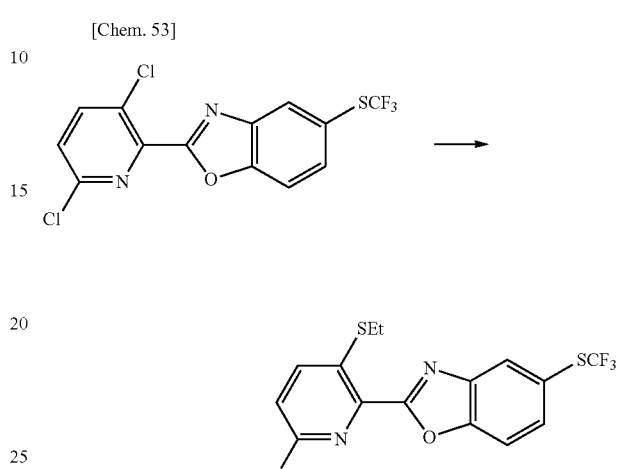

2-(3,6-Dichloropyridin-2-yl)-5-(trifluoromethylthio)benzo[d]oxazole (2.9 g) was reacted according to the production method described in Intermediate Production Example 7 above to give the title compound (3.1 g).

Yield: quantitative

Reference Example 17

Production Method of 2-(3-ethylsulfonyl-6-chloropyridin-2-yl)-5-(trifluoromethylthio)benzo[d]oxazole

[Chem. 54]

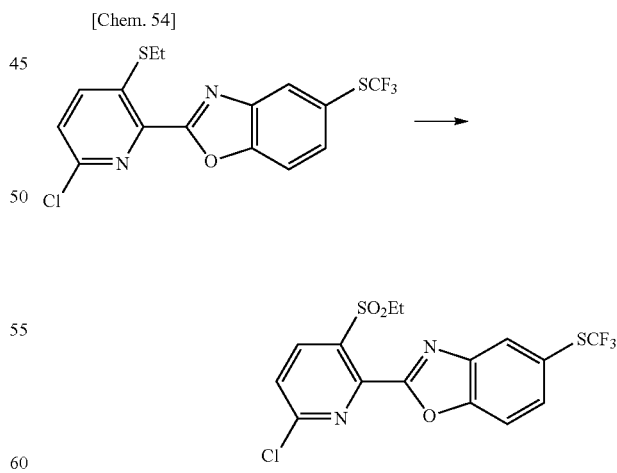

2-(3-Ethylthio-6-chloropyridin-2-yl)-5-(trifluoromethylthio)benzo[d]oxazole (0.52 g) was reacted according to the production method described in Reference Example 6 above to give the title compound (0.54 g).

Yield: 95%

Reference Example 18

Production Method of 2-(3-ethylsulfonyl-6-vinylpyridin-2-yl)-5-(trifluoromethylthio)benzo[d]oxazole

[Chem. 55]

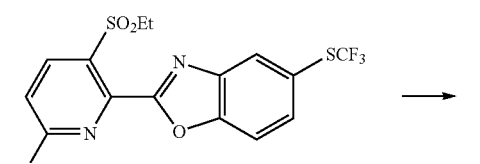

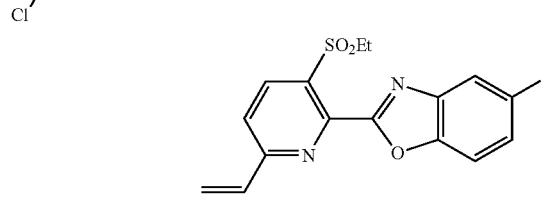

2-(3-Ethylsulfonyl-6-chloropyridin-2-yl)-5-(trifluoromethylthio)benzo[d]oxazole (1.5 g) was reacted according to the production method described in Reference Example 2 above to give the title compound (1.5 g).

Yield: 96%

Reference Example 19

Production Method of 2-(3-ethylsulfonyl-6-formylpyridin-2-yl)-5-(trifluoromethylthio)benzo[d]oxazole

[Chem. 56]

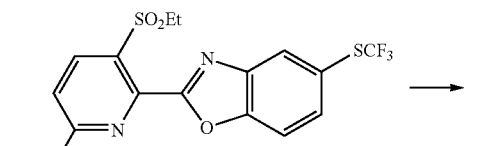

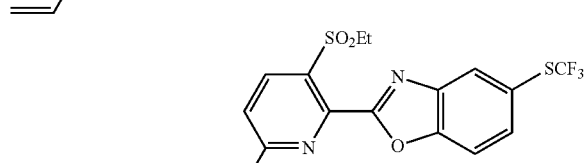

2-(3-Ethylsulfonyl-6-vinylpyridin-2-yl)-5-(trifluoromethylthio)benzo[d]oxazole (1.5 g) was reacted according to the production method described in Reference Example 3 above to give the title compound (1.3 g).

Yield: 88%

Hereinafter, formulation examples are shown, but the present invention is not limited thereto. In the formulation examples, "part" means part by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate (weight ratio of 1:1) | 10 parts |

The above ingredients are uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust formulation.

Formulation Example 3

| | |
|---|---|
| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| | |
|---|---|
| Compound of the present invention | 20 parts |
| Kaolin and synthetic high-dispersion silicic acid | 75 parts |
| Mixture of polyoxyethylene nonylphenyl ether and calcium alkylbenzene sulfonate (weight ratio of 1:1) | 5 parts |

The above ingredients are uniformly mixed and then pulverized to give a wettable powder formulation.

Hereinafter, test examples in connection with the present invention are shown, but the present invention is not limited thereto.

Test Example 1

Test for Control Efficacy on *Myzus persicae*

Chinese cabbage plants were planted in plastic pots (diameter: 8 cm, height: 8 cm), Green peach aphids (*Myzus persicae*) were propagated on the plants, and the number of surviving Green peach aphids in each pot was counted. The compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

Control rate=100−{(T×Ca)/(Ta×C)}×100  [Math. 1]

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-9, 1-41, 1-42, 1-50, 1-86, 1-89, 1-116, 1-118, 1-124, 1-154, 1-156, 1-308, 1-346, 1-384, 2-1, 2-40, 2-41, 2-42, 2-50, 2-86, 2-118, 2-156, 2-308, 2-346, 2-384, 2-420, 3-116, 3-118, 3-154, 3-306 and 4-611 of the present invention showed the activity level evaluated as A.

Test Example 2

Insecticidal Test on *Laodelphax striatellus*

The compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatellus*, and then the glass test tubes were capped with cotton plugs. At 8 days after the inoculation, the numbers of surviving larvae and dead larvae were counted, the corrected mortality rate was calculated according to the formula shown below, and the insecticidal efficacy was evaluated according to the criteria shown below.

Corrected mortality rate(%)=100×(Survival rate in a non-treatment plot−Survival rate in a treatment plot)/Survival rate in a non-treatment plot  [Math. 2]

Criteria
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-9, 1-40, 1-41, 1-42, 1-50, 1-86, 1-89, 1-116, 1-118, 1-154, 1-156, 1-308, 1-346, 1-384, 2-40, 2-41, 2-42, 2-50, 2-116, 2-154, 2-308, 2-346, 3-116, 3-118, 3-154, 3-306, 4-573 and 4-611 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical formulations diluted to 500 ppm, each of which contained a different compound represented by the general formula (1) of the present invention as an active ingredient. After air-dried, the seedlings were kept in a thermostatic chamber at 25° C. At 6 days after the dip treatment, the number of hatched larvae per plot was counted, the corrected mortality rate was calculated according to the formula shown below, and the insecticidal efficacy was evaluated according to the criteria of Test Example 2. This test was conducted in triplicate using 10 adults of *Plutella xylostella* per plot.

Corrected mortality rate(%)=100×(Number of hatched larvae in a non-treatment plot−Number of hatched larvae in a treatment plot)/Number of hatched larvae in a non-treatment plot  [Math. 3]

As a result, the compounds 1-3, 1-9, 1-40, 1-41, 1-42, 1-50, 1-86, 1-89, 1-116, 1-118, 1-124, 1-154, 1-156, 1-308, 1-346, 1-384, 2-1, 2-3, 2-9, 2-40, 2-41, 2-42, 2-50, 2-86, 2-89, 2-116, 2-118, 2-124, 2-154, 2-156, 2-230, 2-306, 2-308, 2-346, 2-384, 3-3, 3-9, 3-116, 3-118, 3-154, 3-306, 4-1, 4-9, 4-460, 4-466, 4-573, 4-575 and 4-611 of the present invention showed the activity level evaluated as A.

INDUSTRIAL APPLICABILITY

The compound of the present invention is highly effective for the control of a wide range of agricultural and horticultural pests and thus is useful.

The invention claimed is:
1. A compound represented by the general formula (1):

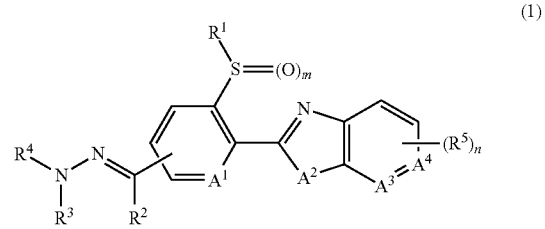

{wherein
R$^1$ represents:
(a1) a (C$_1$-C$_6$) alkyl group;
(a2) a (C$_3$-C$_6$) cycloalkyl group;
(a3) a (C$_2$-C$_6$) alkenyl group; or
(a4) a (C$_2$-C$_6$) alkynyl group,
R$^2$ represents:
(b1) a hydrogen atom;
(b2) a (C$_1$-C$_6$) alkyl group;
(b3) a (C$_3$-C$_6$) cycloalkyl group; or
(b4) a halo (C$_1$-C$_6$) alkyl group,
R$^3$ and R$^4$ independently represents:
(c1) a hydrogen atom;
(c2) a (C$_1$-C$_6$) alkyl group;
(c3) a (C$_2$-C$_6$) alkenyl group;
(c4) a (C$_2$-C$_6$) alkynyl group;
(c5) a (C$_3$-C$_6$) cycloalkyl group;
(c6) a (C$_3$-C$_6$) cycloalkyl (C$_1$-C$_6$) alkyl group;
(c7) a (C$_1$-C$_6$) alkoxy (C$_1$-C$_6$) alkyl group;
(c8) a halo (C$_1$-C$_6$) alkyl group;
(c9) a halo (C$_2$-C$_6$) alkenyl group;
(c10) a halo (C$_2$-C$_6$) alkynyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a (C$_1$-C$_6$) alkyl group, (f) a halo (C$_1$-C$_6$) alkyl group, (g) a (C$_1$-C$_6$)

alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;

(c13) a phenyl ($C_1$-$C_6$) alkyl group;

(c14) a phenyl ($C_1$-$C_6$) alkyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;

(c15) a ($C_1$-$C_6$) alkylcarbonyl group;
(c16) a ($C_3$-$C_6$) cycloalkylcarbonyl group;
(c17) a ($C_1$-$C_6$) alkoxycarbonyl group;
(c18) a halo ($C_1$-$C_6$) alkylcarbonyl group;
(c19) a ($C_1$-$C_6$) alkylthiocarbonyl group;
(c20) a ($C_3$-$C_6$) cycloalkylthiocarbonyl group;
(c21) a ($C_1$-$C_6$) alkoxythiocarbonyl group;
(c22) a halo ($C_1$-$C_6$) alkylthiocarbonyl group;
(c23) a mono-($C_1$-$C_6$) alkylaminothiocarbonyl group;
(c24) a di-($C_1$-$C_6$) alkylaminothiocarbonyl group;
(c25) a ($C_1$-$C_6$) alkylthio group;
(c26) a ($C_1$-$C_6$) alkylsulfinyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group, $R^5$ represents:
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group, $A^1$, $A^3$ and $A^4$ each represent CH or a nitrogen atom,
$A^2$ represents an oxygen atom; a sulfur atom; or N—$R^6$ (wherein $R^6$ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0; 1; or 2, and
n represents 0; 1; or 2}, or
a salt thereof.

2. The compound or the salt according to claim 1, represented by the general formula (1A):

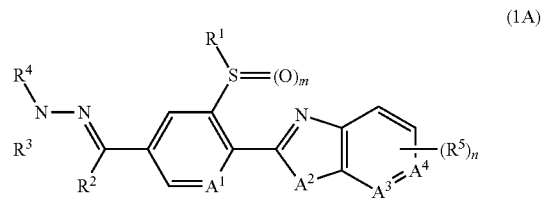

(1A)

{wherein
$R^1$ represents:
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group, $R^2$ represents:
(b1) a hydrogen atom;
(b2) a ($C_1$-$C_6$) alkyl group;
(b3) a ($C_3$-$C_6$) cycloalkyl group; or
(b4) a halo ($C_1$-$C_6$) alkyl group, $R^3$ and $R^4$ independently represents:
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;

(c13) a phenyl ($C_1$-$C_6$) alkyl group;
(c14) a phenyl ($C_1$-$C_6$) alkyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;

(c15) a ($C_1$-$C_6$) alkylcarbonyl group;
(c16) a ($C_3$-$C_6$) cycloalkylcarbonyl group;
(c17) a ($C_1$-$C_6$) alkoxycarbonyl group;
(c18) a halo ($C_1$-$C_6$) alkylcarbonyl group;
(c19) a ($C_1$-$C_6$) alkylthiocarbonyl group;
(c20) a ($C_3$-$C_6$) cycloalkylthiocarbonyl group;
(c21) a ($C_1$-$C_6$) alkoxythiocarbonyl group;
(c22) a halo ($C_1$-$C_6$) alkylthiocarbonyl group;
(c23) a mono-($C_1$-$C_6$) alkylaminothiocarbonyl group;
(c24) a di-($C_1$-$C_6$) alkylaminothiocarbonyl group;
(c25) a ($C_1$-$C_6$) alkylthio group;

(c26) a $(C_1-C_6)$ alkylsulfinyl group;
(c27) a $(C_1-C_6)$ alkylsulfonyl group;
(c28) a $(C_1-C_6)$ alkylthio $(C_1-C_6)$ alkyl group;
(c29) a $(C_1-C_6)$ alkylsulfinyl $(C_1-C_6)$ alkyl group;
(c30) a $(C_1-C_6)$ alkylsulfonyl $(C_1-C_6)$ alkyl group;
(c31) a halo $(C_1-C_6)$ alkylthio $(C_1-C_6)$ alkyl group;
(c32) a halo $(C_1-C_6)$ alkylsulfinyl $(C_1-C_6)$ alkyl group;
(c33) a halo $(C_1-C_6)$ alkylsulfonyl $(C_1-C_6)$ alkyl group; or
(c34) a cyano $(C_1-C_6)$ alkyl group,
  $R^5$ represents:
(d1) a halogen atom;
(d2) a cyano group;
(d3) a nitro group;
(d4) a $(C_1-C_6)$ alkyl group;
(d5) a $(C_1-C_6)$ alkoxy group;
(d6) a $(C_2-C_6)$ alkenyloxy group;
(d7) a $(C_2-C_6)$ alkynyloxy group;
(d8) a halo $(C_1-C_6)$ alkyl group;
(d9) a halo $(C_1-C_6)$ alkoxy group;
(d10) a halo $(C_2-C_6)$ alkenyloxy group;
(d11) a halo $(C_2-C_6)$ alkynyloxy group;
(d12) a $(C_1-C_6)$ alkylthio group;
(d13) a $(C_1-C_6)$ alkylsulfinyl group;
(d14) a $(C_1-C_6)$ alkylsulfonyl group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
  $A^1$, $A^3$ and $A^4$ each represent CH or a nitrogen atom,
  $A^2$ represents an oxygen atom; a sulfur atom; or $N-R^6$ (wherein $R^6$ represents (e1) a $(C_1-C_6)$ alkyl group; (e2) a $(C_3-C_6)$ cycloalkyl group; (e3) a $(C_2-C_6)$ alkenyl group; or (e4) a $(C_2-C_6)$ alkynyl group),
  m represents 0; 1; or 2, and
  n represents 0; 1; or 2}.

3. The compound or the salt according to claim 2, wherein:
  $R^1$ is (a1) a $(C_1-C_6)$ alkyl group,
  $R^2$ is (b1) a hydrogen atom,
  $R^3$ and $R^4$ are independently
(c1) a hydrogen atom;
(c2) a $(C_1-C_6)$ alkyl group;
(c3) a $(C_2-C_6)$ alkenyl group;
(c4) a $(C_2-C_6)$ alkynyl group;
(c5) a $(C_3-C_6)$ cycloalkyl group;
(c7) a $(C_1-C_6)$ alkoxy $(C_1-C_6)$ alkyl group;
(c8) a halo $(C_1-C_6)$ alkyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group;
(c15) a $(C_1-C_6)$ alkylcarbonyl group;
(c17) a $(C_1-C_6)$ alkoxycarbonyl group;
(c18) a halo $(C_1-C_6)$ alkylcarbonyl group;
(c21) a $(C_1-C_6)$ alkoxythiocarbonyl group;
(c23) a mono-$(C_1-C_6)$ alkylaminothiocarbonyl group;
(c24) a di-$(C_1-C_6)$ alkylaminothiocarbonyl group;
(c27) a $(C_1-C_6)$ alkylsulfonyl group;
(c28) a $(C_1-C_6)$ alkylthio $(C_1-C_6)$ alkyl group;
(c29) a $(C_1-C_6)$ alkylsulfinyl $(C_1-C_6)$ alkyl group;
(c30) a $(C_1-C_6)$ alkylsulfonyl $(C_1-C_6)$ alkyl group;
(c31) a halo $(C_1-C_6)$ alkylthio $(C_1-C_6)$ alkyl group;
(c32) a halo $(C_1-C_6)$ alkylsulfinyl $(C_1-C_6)$ alkyl group;
(c33) a halo $(C_1-C_6)$ alkylsulfonyl $(C_1-C_6)$ alkyl group; or
(c34) a cyano $(C_1-C_6)$ alkyl group,
  $R^5$ is:
(d8) a halo $(C_1-C_6)$ alkyl group;
(d15) a halo $(C_1-C_6)$ alkylthio group; or
(d17) a halo $(C_1-C_6)$ alkylsulfonyl group,
  $A^1$ is a nitrogen atom,
  $A^3$ is CH or a nitrogen atom,
  $A^4$ is CH,
  $A^2$ is an oxygen atom or $N-R^6$ (wherein $R^6$ is (e1) a $(C_1-C_6)$ alkyl group),
  m is 2, and
  n is 1.

4. The compound or the salt according to claim 2, wherein:
  $R^3$ and $R^4$ are independently:
(c1) a hydrogen atom;
(c2) a $(C_1-C_6)$ alkyl group;
(c7) a $(C_1-C_6)$ alkoxy $(C_1-C_6)$ alkyl group;
(c8) a halo $(C_1-C_6)$ alkyl group;
(c12) a phenyl group having, on the ring, 1 to 5 substituting groups independently selected from the group consisting of (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c15) a $(C_1-C_6)$ alkylcarbonyl group;
(c17) a $(C_1-C_6)$ alkoxycarbonyl group;
(c21) a $(C_1-C_6)$ alkoxythiocarbonyl group;
(c23) a mono-$(C_1-C_6)$ alkylaminothiocarbonyl group;
(c24) a di-$(C_1-C_6)$ alkylaminothiocarbonyl group;
(c27) a $(C_1-C_6)$ alkylsulfonyl group; or
(c33) a halo $(C_1-C_6)$ alkylsulfonyl $(C_1-C_6)$ alkyl group.

5. The compound or the salt according to claim 1, represented by the general formula (1B):

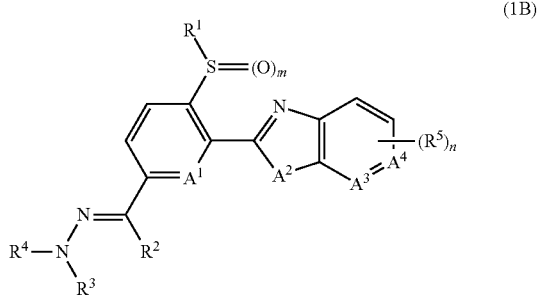

{wherein
  $R^1$ represents:
(a1) a $(C_1-C_6)$ alkyl group;
(a2) a $(C_3-C_6)$ cycloalkyl group;
(a3) a $(C_2-C_6)$ alkenyl group; or
(a4) a $(C_2-C_6)$ alkynyl group, R² represents:
(b1) a hydrogen atom;
(b2) a ($C_1$-$C_6$) alkyl group;
(b3) a ($C_3$-$C_6$) cycloalkyl group; or
(b4) a halo ($C_1$-$C_6$) alkyl group,
R³ and R⁴ independently represents:
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c14) a phenyl ($C_1$-$C_6$) alkyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group;
(c16) a ($C_3$-$C_6$) cycloalkylcarbonyl group;
(c17) a ($C_1$-$C_6$) alkoxycarbonyl group;
(c18) a halo ($C_1$-$C_6$) alkylcarbonyl group;
(c19) a ($C_1$-$C_6$) alkylthiocarbonyl group;
(c20) a ($C_3$-$C_6$) cycloalkylthiocarbonyl group;
(c21) a ($C_1$-$C_6$) alkoxythiocarbonyl group;
(c22) a halo ($C_1$-$C_6$) alkylthiocarbonyl group;
(c23) a mono-($C_1$-$C_6$) alkylaminothiocarbonyl group;
(c24) a di-($C_1$-$C_6$) alkylaminothiocarbonyl group;
(c25) a ($C_1$-$C_6$) alkylthio group;
(c26) a ($C_1$-$C_6$) alkylsulfinyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group,
R⁵ represents:
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
  $A^1$, $A^3$ and $A^4$ each represent CH or a nitrogen atom,
  $A^2$ represents an oxygen atom; a sulfur atom; or N—R⁶ (wherein R⁶ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
  m represents 0; 1; or 2, and
  n represents 0; 1; or 2}.

6. The compound or the salt according to claim 5, wherein:
R¹ is (a1) a ($C_1$-$C_6$) alkyl group,
R² is (b1) a hydrogen atom,
R³ and R⁴ are independently:
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c7) a ($C_1$-$C_6$) alkoxy ($C_1$-$C_6$) alkyl group;
(c8) a halo ($C_1$-$C_6$) alkyl group;
(c11) a phenyl group;
(c12) a phenyl group having, on the ring, 1 to 5 substituting groups independently selected from the group consisting of (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c15) a ($C_1$-$C_6$) alkylcarbonyl group;
(c17) a ($C_1$-$C_6$) alkoxycarbonyl group;
(c18) a halo ($C_1$-$C_6$) alkylcarbonyl group;
(c21) a ($C_1$-$C_6$) alkoxythiocarbonyl group;
(c23) a mono-($C_1$-$C_6$) alkylaminothiocarbonyl group;
(c24) a di-($C_1$-$C_6$) alkylaminothiocarbonyl group;
(c27) a ($C_1$-$C_6$) alkylsulfonyl group;
(c28) a ($C_1$-$C_6$) alkylthio ($C_1$-$C_6$) alkyl group;
(c29) a ($C_1$-$C_6$) alkylsulfinyl ($C_1$-$C_6$) alkyl group;
(c30) a ($C_1$-$C_6$) alkylsulfonyl ($C_1$-$C_6$) alkyl group;
(c31) a halo ($C_1$-$C_6$) alkylthio ($C_1$-$C_6$) alkyl group;
(c32) a halo ($C_1$-$C_6$) alkylsulfinyl ($C_1$-$C_6$) alkyl group;
(c33) a halo ($C_1$-$C_6$) alkylsulfonyl ($C_1$-$C_6$) alkyl group; or
(c34) a cyano ($C_1$-$C_6$) alkyl group,
R⁵ is:
(d8) a halo ($C_1$-$C_6$) alkyl group;
(d15) a halo ($C_1$-$C_6$) alkylthio group; or
(d17) a halo ($C_1$-$C_6$) alkylsulfonyl group,
$A^1$ is a nitrogen atom,
$A^3$ is CH or a nitrogen atom,
$A^4$ is CH,
$A^2$ is an oxygen atom or N—R⁶ (wherein R⁶ is (e1) a ($C_1$-$C_6$) alkyl group),
m is 2, and
n is 1.

7. The compound or the salt according to claim 5, wherein $R^3$ and $R^4$ are independently:

(c1) a hydrogen atom;
(c2) a $(C_1-C_6)$ alkyl group;
(c7) a $(C_1-C_6)$ alkoxy $(C_1-C_6)$ alkyl group;
(c8) a halo $(C_1-C_6)$ alkyl group;
(c15) a $(C_1-C_6)$ alkylcarbonyl group;
(c17) a $(C_1-C_6)$ alkoxycarbonyl group;
(c18) a halo $(C_1-C_6)$ alkylcarbonyl group;
(c21) a $(C_1-C_6)$ alkoxythiocarbonyl group; or
(c33) a halo $(C_1-C_6)$ alkylsulfonyl $(C_1-C_6)$ alkyl group.

8. An agricultural and horticultural insecticide comprising the compound or the salt according to claim 1 as an active ingredient.

9. A method for an agricultural and horticultural insecticide, comprising treating plants or soil with an effective amount of the agricultural and horticultural insecticide according to claim 8.

10. An animal ectoparasite control agent comprising an effective amount of the compound or the salt according to claim 1 as an active ingredient.

* * * * *

UNITED STATES PATENT AND TRADEMARK OFFICE
CERTIFICATE OF CORRECTION

PATENT NO. : 10,377,754 B2
APPLICATION NO. : 16/327236
DATED : August 13, 2019
INVENTOR(S) : Sano et al.

It is certified that error appears in the above-identified patent and that said Letters Patent is hereby corrected as shown below:

On the Title Page

Column 2, item (57), abstract, Line 20 approx., delete "C-H," and insert --CH,--, therefor.

In the Specification

Column 10, Line 40, after "$(C_1\text{-}C_6$" insert --)--.

Column 17, Line 1, delete "amine" and insert --ammine--, therefor.

Column 23, Lines 57-60 (approx.), delete "(1a′-2))" and insert --(1a′-2)--, therefor.

Column 25, Lines 16-18 (approx.), delete "[Chem. 27]" and insert --[Chem. 7]--, therefor.

Column 67, Line 54, delete "ringoneella," and insert --ringoniella,--, therefor.

Column 68, Line 15, delete "Eupoecillia" and insert --Eupoecilia--, therefor.

Column 68, Line 45, delete "Rhopalosophum" and insert --Rhopalosiphum--, therefor.

Column 68, Line 56, delete "longispinis," and insert --longispinus,--, therefor.

Column 68, Line 64, delete "oratorios," and insert --oratorius,--, therefor.

Column 68, Line 64, delete "Uroeucon" and insert --Uroleucon--, therefor.

Column 69, Line 2, delete "spinolai," and insert --spinolae,--, therefor.

Column 69, Line 9, delete "Rhopalosophum" and insert --Rhopalosiphum--, therefor.

Signed and Sealed this
Seventh Day of April, 2020

Andrei Iancu
*Director of the United States Patent and Trademark Office*

Column 69, Line 11, delete "Speusotettix" and insert --Speudotettix--, therefor.

Column 69, Line 14, delete "trigones," and insert --trigonus,--, therefor.

Column 69, Line 18, delete "vitifolii," and insert --vitifoliae,--, therefor.

Column 69, Line 19, delete "aceta," and insert --acuta,--, therefor.

Column 69, Lines 35-36, delete "Aphidonuguis" and insert --Aphidophagous--, therefor.

Column 69, Line 36, delete "ishidai," and insert --ishidae,--, therefor.

Column 69, Line 52, delete "Meatus" and insert --Neatus--, therefor.

Column 70, Line 6, delete "Chlorqps" and insert --Chlorops--, therefor.

Column 70, Line 25, delete "infumata infumata," and insert --infumata,--, therefor.

Column 70, Line 43, delete "Franklinella" and insert --Frankliniella--, therefor.

Column 70, Line 54, delete "sylvairum," and insert --sylviarum,--, therefor.

Column 70, Line 55, delete "chibaensis," and insert --chinensis,--, therefor.

Column 70, Line 58, delete "moorei," and insert --mite,--, therefor.

Column 70, Line 58, delete "Octodectes" and insert --Otodectes--, therefor.

Column 70, Line 59, delete "ptrenyssnus," and insert --pteronyssinus,--, therefor.

Column 70, Line 62, delete "Rhyzoglyphus" and insert --Rhizoglyphus--, therefor.

Column 71, Line 15 approx., delete "Tylenchus" and insert --Tylenchulus--, therefor.

Column 71, Line 19, delete "Lehmannina valentiana," and insert --Lehmannia valentina,--, therefor.

Column 71, Line 32 approx., delete "taiwanesis;" and insert --taiwanensis;--, therefor.

Column 71, Line 38 approx., delete "cosa," and insert --tosa,--, therefor.

Column 71, Line 40, delete "miyagawai;" and insert --miyagawa;--, therefor.

Column 71, Line 41, delete "parasitivorax" and insert --parasitovorax--, therefor.

Column 80, Line 20, delete "benzensulfonate" and insert --benzenesulfonate--, therefor.

Column 81, Line 15, delete "imazamethapyr," and insert --imazethapyr,--, therefor.

Column 82, Line 23, delete "flumezin," and insert --fluomizin,--, therefor.

Column 82, Line 62, delete "radiobactor," and insert --radiobacter,--, therefor.

Column 98, Lines 20-25 (approx.), delete "SEt" and insert --SO$_2$Et--, therefor.

Column 102, Lines 50-55 (approx.), delete "O HN" and insert --OHN--, therefor.

In the Claims

Column 113, Line 39, Claim 3, after "independently" insert --:--.